US012774340B2

(12) United States Patent
Zhai et al.

(10) Patent No.: US 12,774,340 B2
(45) Date of Patent: Oct. 27, 2026

(54) ANTI-4-1BB SINGLE-DOMAIN ANTIBODIES, NANOBODIES, FUSION PROTEINS THEREOF AND METHODS OF USE THEREOF FOR TREATMENT

(71) Applicant: BIOTHEUS INC., Zhuhai (CN)

(72) Inventors: Tianhang Zhai, Zhuhai (CN); Xiaoniu Miao, Zhuhai (CN); Yifeng Xu, Zhuhai (CN); Chao Wang, Zhuhai (CN); Andy Tsun, Zhuhai (CN)

(73) Assignee: BIOTHEUS INC., Zhuhai (CN)

( * ) Notice: Subject to any disclaimer, the term of this patent is extended or adjusted under 35 U.S.C. 154(b) by 612 days.

(21) Appl. No.: 18/245,691

(22) PCT Filed: Sep. 17, 2021

(86) PCT No.: PCT/CN2021/118955
§ 371 (c)(1),
(2) Date: Mar. 16, 2023

(87) PCT Pub. No.: WO2022/057875
PCT Pub. Date: Mar. 24, 2022

(65) Prior Publication Data

US 2023/0357422 A1 Nov. 9, 2023

(30) Foreign Application Priority Data

Sep. 17, 2020 (CN) ......................... 202010981835.5
Sep. 25, 2020 (CN) ......................... 202011025265.9

(51) Int. Cl.
*C07K 16/28* (2006.01)
*A61K 39/00* (2006.01)

(52) U.S. Cl.
CPC .......... *C07K 16/2875* (2013.01); *A61K 39/00* (2013.01); *C07K 2317/24* (2013.01); *C07K 2317/33* (2013.01); *C07K 2317/565* (2013.01); *C07K 2317/567* (2013.01); *C07K 2317/569* (2013.01); *C07K 2317/92* (2013.01)

(58) Field of Classification Search
CPC ............ C07K 16/2875; C07K 2317/24; C07K 2317/33; C07K 2317/565; C07K 2317/567; C07K 2317/569; C07K 2317/92; C07K 2317/22; C07K 2317/34; C07K 2317/70; C07K 2317/75; C07K 2317/76; C07K 14/70578; C07K 16/2878; C07K 2319/30; A61K 39/00; A61K 47/64; A61K 47/6801; A61K 47/6803; A61K 2039/505; A61P 35/00; G01N 33/6872; G01N 33/531; G01N 33/575; G01N 2333/70578
See application file for complete search history.

(56) References Cited

U.S. PATENT DOCUMENTS

| | | | |
|---|---|---|---|
| 8,337,850 B2 | 12/2012 | Ahrens et al. |
| 2018/0258177 A1 | 9/2018 | Kwon et al. |
| 2019/0062445 A1 | 2/2019 | Jure-Kunkel et al. |
| 2020/0048350 A1 | 2/2020 | Eckelman et al. |
| 2021/0363266 A1 | 11/2021 | Huang et al. |

FOREIGN PATENT DOCUMENTS

| | | |
|---|---|---|
| CA | 3089260 A1 | 7/2019 |
| CN | 105481983 A | 4/2016 |
| CN | 109970865 A | 7/2019 |
| CN | 110627906 A | 12/2019 |
| CN | 111065652 A | 4/2020 |
| CN | 111542342 A | 8/2020 |
| WO | 2005/035584 A1 | 4/2005 |
| WO | 2012/032433 A1 | 3/2012 |
| WO | 2017/123650 A2 | 7/2017 |
| WO | 2019/092452 A1 | 5/2019 |
| WO | 2019/113039 A1 | 6/2019 |

OTHER PUBLICATIONS

International Search Report and Written Opinion mailed Dec. 14, 2021, directed to International Application No. PCT/CN2021/118955.

Bagheri, S. et al., "Selection of single chain antibody fragments binding to the extracellular domain of 4-1BB receptor by phage display technology.", Tumor Biology.,vol. 39, No. 3, Mar. 31, 2017 (Mar. 31, 2017), 1-34; pp. 1-13.

Chen, Zhehao et al. "Characteristics and Clinical Development Status of Therapeutic Single Domain Antibody", Chinese Journal of New Drugs),vol. 28, No. 21, Dec. 31, 2019 (Dec. 31, 2019), 1-34, pp. 2581-2587.

Segal, N. H. et al., "Results from an Integrated Safety Analysis of Urelumab, an Agonist Anti-CD137 Monoclonal Antibody.", Clin Cancer Res.,vol. 23, No. 8, Oct. 18, 2016 (Oct. 18, 2016), pp. 1929-1936.

Bagheri, S. et al., "Targeting the 4-1BB costimulatory molecule through single chain antibodies promotes the human T-cell response.", Cellular & Molecular Biology Letters., vol. 25, Apr. 22, 2020 (Apr. 22, 2020), vol. 28, pp. 1-13.

(Continued)

*Primary Examiner* — Robert S Landsman

(74) *Attorney, Agent, or Firm* — Michele V. Frank; Keith G. Haddaway; Venable LLP

(57) ABSTRACT

Related is a single-domain antibody targeting 4-1BB, a fusion protein thereof, a pharmaceutical composition and a use thereof. Specifically, the related single-domain antibody comprises one heavy chain variable region, and the amino acid sequences of CDR1-CDR3 contained in the heavy chain variable region are as shown in any item in table B, respectively. The single-domain antibody can bind to human 4-1BB and at the same time cross-bind to cynomolgus 4-1BB; in addition, with the help of external cross-linking, T cells are activated, which have excellent anti-tumor activity and safety.

23 Claims, 9 Drawing Sheets

Specification includes a Sequence Listing.

(56) References Cited

OTHER PUBLICATIONS

Etxeberria I, et al. New emerging targets in cancer immunotherapy: CD137/4-1BB costimulatory axis., ESMO Open 2020;4:e000733. doi:10.1136/esmoopen-2020-000733. pp 1-7.
First Office Action from Chinese Patent Application No. 202011025265.9 dated Apr. 4, 2024.
First Examination Report from Chinese Patent Application No. 202011025265.9 dated Apr. 4, 2024.
Zhou, et al. "Preparation of anti-human 4-1BB monoclonal antibody and characterization of its biological activities," (Chin J Cell Mol Immunol) 2011, 27( 9).
Chester, et al. "Immunotherapy targeting 4-1BB: mechanistic rationale, clinical results, and future strategies," The American Society of Hematology, Jan. 4, 2018, vol. 131 (1), pp. 49-57.
Supplementary European Search Report from EP Patent Application No. 21868697.0 dated Sep. 4, 2024.
Extended European Search Report from EP Patent Application No. 21868697.0 dated Nov. 4, 2024.
Notice of Reasons for Rejection from JP Patent Application No. 2023-517935 dated Nov. 4, 2025.

SEQUENCE LISTING

```
<160> NUMBER OF SEQ ID NOS: 174

<210> SEQ ID NO 1
<211> LENGTH: 116
<212> TYPE: PRT
<213> ORGANISM: Artificial Sequence
<220> FEATURE:
<223> OTHER INFORMATION: single-domain antibody

<400> SEQUENCE: 1

Gln Val Gln Leu Val Glu Ser Gly Gly Gly Leu Val Pro Pro Gly Glu
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gln Arg Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ala Arg Asn Thr Val Ser Leu
65                  70                  75                  80

Gln Met Asn Ser Leu Lys Pro Glu Asp Thr Ala Ile Tyr Tyr Cys His
                85                  90                  95

Ile Gly Pro Glu Pro Arg Tyr Gly Tyr Trp Gly Gln Gly Thr Gln Val
            100                 105                 110

Thr Val Ser Ser
        115
```

<210> SEQ ID NO 2
<211> LENGTH: 116
<212> TYPE: PRT
<213> ORGANISM: Artificial Sequence
<220> FEATURE:
<223> OTHER INFORMATION: single-domain antibody

<400> SEQUENCE: 2

```
Gln Val Gln Leu Val Glu Ser Gly Gly Gly Leu Val Pro Pro Gly Glu
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gln Arg Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ala Glu Asn Thr Val Ser Leu
65                  70                  75                  80

Gln Met Asn Ser Leu Lys Pro Glu Asp Thr Ala Ile Tyr Tyr Cys His
                85                  90                  95

Ile Gly Pro Glu Pro Arg Tyr Gly Tyr Trp Gly Gln Gly Thr Gln Val
            100                 105                 110

Thr Val Ser Ser
        115
```

<210> SEQ ID NO 3
<211> LENGTH: 116
<212> TYPE: PRT
<213> ORGANISM: Artificial Sequence
<220> FEATURE:
<223> OTHER INFORMATION: single-domain antibody

<400> SEQUENCE: 3

```
Gln Val Gln Leu Val Glu Ser Gly Gly Gly Leu Val Pro Pro Gly Glu
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gln Arg Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ala Lys Asn Thr Val Tyr Leu
65                  70                  75                  80

Gln Met Asn Ser Leu Lys Pro Glu Asp Thr Ala Ile Tyr Tyr Cys His
                85                  90                  95

Ile Gly Pro Glu Pro Arg Tyr Gly Tyr Trp Gly Gln Gly Thr Gln Val
            100                 105                 110

Thr Val Ser Ser
        115
```

<210> SEQ ID NO 4
<211> LENGTH: 121
<212> TYPE: PRT
<213> ORGANISM: Artificial Sequence
<220> FEATURE:
<223> OTHER INFORMATION: single-domain antibody

<400> SEQUENCE: 4

```
Gln Val Gln Leu Gln Glu Ser Gly Gly Gly Leu Val Gln Val Gly Gly
1               5                   10                  15
```

-continued

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Leu Tyr Thr Gly Asp Asp Tyr Trp Gly
            100                 105                 110

Gln Gly Thr Gln Val Thr Val Ser Ser
        115                 120

<210> SEQ ID NO 5
<211> LENGTH: 127
<212> TYPE: PRT
<213> ORGANISM: Artificial Sequence
<220> FEATURE:
<223> OTHER INFORMATION: single-domain antibody

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Glu Thr Thr Tyr Tyr Ser Asp Ser Val
    50                  55                  60

Lys Gly Arg Phe Thr Ile Ser Arg Asp Asn Ala Lys Asn Lys Val Tyr
65                  70                  75                  80

Leu Gln Met Asn Ser Leu Lys Pro Glu Asp Thr Ala Val Tyr Tyr Cys
                85                  90                  95

Gly Ala Glu Leu Leu Gly Ser Gly Glu Gly Cys Tyr Val Trp Ser Arg
            100                 105                 110

Asp Gly Ser Tyr Trp Gly Gln Gly Thr Gln Val Thr Val Ser Ser
        115                 120                 125

<210> SEQ ID NO 6
<211> LENGTH: 116
<212> TYPE: PRT
<213> ORGANISM: Artificial Sequence
<220> FEATURE:
<223> OTHER INFORMATION: single-domain antibody

<400> SEQUENCE: 6

Gln Val Gln Leu Gln Glu Ser Gly Gly Gly Leu Val Pro Pro Gly Glu
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gln Arg Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ala Lys Asn Thr Val Ser Leu

```
65                  70                  75                  80

Gln Met Asn Ser Leu Lys Pro Glu Asp Thr Ala Ile Tyr Tyr Cys His
                85                  90                  95

Ile Gly Pro Glu Pro Arg Tyr Gly Tyr Trp Gly Gln Gly Thr Gln Val
            100                 105                 110

Thr Val Ser Ser
        115


<210> SEQ ID NO 7
<211> LENGTH: 121
<212> TYPE: PRT
<213> ORGANISM: Artificial Sequence
<220> FEATURE:
<223> OTHER INFORMATION: single-domain antibody

<400> SEQUENCE: 7

Gln Val Gln Leu Gln Glu Ser Gly Gly Gly Leu Val Gln Val Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Arg Tyr Ser Ser Asp Asp Tyr Trp Gly
            100                 105                 110

Gln Gly Thr Gln Val Thr Val Ser Ser
        115                 120


<210> SEQ ID NO 8
<211> LENGTH: 121
<212> TYPE: PRT
<213> ORGANISM: Artificial Sequence
<220> FEATURE:
<223> OTHER INFORMATION: single-domain antibody

<400> SEQUENCE: 8

Gln Val Gln Leu Gln Glu Ser Gly Gly Gly Leu Val Glu Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Arg Tyr Ser Ser Asp Asp Tyr Trp Gly
            100                 105                 110

Pro Gly Thr Gln Val Thr Val Ser Ser
        115                 120
```

<210> SEQ ID NO 9
<211> LENGTH: 121
<212> TYPE: PRT
<213> ORGANISM: Artificial Sequence
<220> FEATURE:
<223> OTHER INFORMATION: single-domain antibody

<400> SEQUENCE: 9

Glu Val Gln Leu Gln Glu Ser Gly Gly Gly Leu Val Gln Ala Gly Gly
1 5 10 15

Ser Leu Arg Leu Ser Cys Ala Ala Ser Gly Phe Thr Phe Asp Asp Tyr
20 25 30

Ala Ile Gly Trp Phe Arg Gln Ala Pro Gly Lys Glu Arg Glu Gly Val
35 40 45

Leu Cys Ile Ser Ser Ser Gly Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Thr Asn Leu Lys Pro Glu Asp Thr Ala Val Tyr Leu Cys
85 90 95

Gly Ala Pro Arg Asp Cys Ser Tyr Tyr Thr Gly Asp Asp Tyr Trp Gly
100 105 110

Gln Gly Thr Gln Val Thr Val Ser Ser
115 120

<210> SEQ ID NO 10
<211> LENGTH: 122
<212> TYPE: PRT
<213> ORGANISM: Artificial Sequence
<220> FEATURE:
<223> OTHER INFORMATION: single-domain antibody

<400> SEQUENCE: 10

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Ser Leu Gly Leu Tyr
20 25 30

Ala Ile Gly Trp Phe Arg Gln Ala Pro Gly Lys Glu Arg Glu Trp Val
35 40 45

Ser Cys Ile Met Ser Ser Asp Ser Ser Ala Tyr Tyr Ala Asp Ser Val
50 55 60

Lys Gly Arg Phe Thr Val Ser Arg Asp Asn Ala Lys Asn Thr Val Tyr
65 70 75 80

Leu Gln Met Asn Arg Leu Lys Pro Glu Asp Thr Ala Val Tyr Tyr Cys
85 90 95

Ala Ala Pro Gln Ser Asp Cys Phe His Tyr Ser Glu Asn Asp Tyr Trp
100 105 110

Gly Gln Gly Thr Gln Val Thr Val Ser Ser
115 120

<210> SEQ ID NO 11
<211> LENGTH: 121
<212> TYPE: PRT
<213> ORGANISM: Artificial Sequence
<220> FEATURE:
<223> OTHER INFORMATION: single-domain antibody

<400> SEQUENCE: 11

Gln Val Gln Leu Gln Glu Ser Gly Gly Gly Leu Val Gln Pro Gly Gly

```
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Arg Tyr Ser Ser Asp Asp Tyr Trp Gly
            100                 105                 110

Gln Gly Thr Gln Val Thr Val Ser Ser
        115                 120


<210> SEQ ID NO 12
<211> LENGTH: 121
<212> TYPE: PRT
<213> ORGANISM: Artificial Sequence
<220> FEATURE:
<223> OTHER INFORMATION: single-domain antibody

<400> SEQUENCE: 12

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Arg Tyr Ser Ser Asp Asp Tyr Trp Gly
            100                 105                 110

Gln Gly Thr Gln Val Thr Val Ser Ser
        115                 120


<210> SEQ ID NO 13
<211> LENGTH: 122
<212> TYPE: PRT
<213> ORGANISM: Artificial Sequence
<220> FEATURE:
<223> OTHER INFORMATION: single-domain antibody

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Leu Gly Leu Tyr
            20                  25                  30

Ala Ile Gly Trp Phe Arg Gln Ala Pro Gly Lys Glu Arg Glu Trp Val
        35                  40                  45

Ser Cys Ile Met Ser Ser Asp Ser Ser Ala Tyr Tyr Ala Asp Ser Val
    50                  55                  60
```

Lys Gly Arg Phe Thr Val Ser Arg Asp Asn Ala Lys Asn Thr Val Tyr
65 70 75 80

Leu Gln Met Asn Arg Leu Lys Pro Glu Asp Thr Ala Val Tyr Tyr Cys
85 90 95

Ala Ala Pro Gln Ser Asp Cys Phe His Tyr Ser Glu Asn Asp Tyr Trp
100 105 110

Gly Gln Gly Thr Gln Val Thr Val Ser Ser
115 120

<210> SEQ ID NO 14
<211> LENGTH: 122
<212> TYPE: PRT
<213> ORGANISM: Artificial Sequence
<220> FEATURE:
<223> OTHER INFORMATION: single-domain antibody

<400> SEQUENCE: 14

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Ser Leu Asp Tyr Tyr
20 25 30

Ala Ile Gly Trp Phe Arg Gln Ala Pro Gly Lys Glu Arg Glu Trp Val
35 40 45

Ser Cys Ile Met Ser Ser Asp Ser Ser Ala Tyr Tyr Ala Asp Ser Val
50 55 60

Lys Gly Arg Phe Thr Ile Ser Arg Asp Asn Ala Lys Asn Leu Val Tyr
65 70 75 80

Leu Arg Met Asn Ser Leu Lys Pro Glu Asp Thr Ala Val Tyr Tyr Cys
85 90 95

Thr Ala Pro Arg Ser Asp Cys Phe His Tyr Gly Glu Asn Asp Tyr Trp
100 105 110

Gly Gln Gly Thr Gln Val Thr Val Ser Ser
115 120

<210> SEQ ID NO 15
<211> LENGTH: 122
<212> TYPE: PRT
<213> ORGANISM: Artificial Sequence
<220> FEATURE:
<223> OTHER INFORMATION: single-domain antibody

<400> SEQUENCE: 15

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Leu Asp Tyr Tyr
20 25 30

Ala Ile Gly Trp Phe Arg Gln Ala Pro Gly Lys Glu Arg Glu Trp Val
35 40 45

Ser Cys Ile Thr Ala Ser Asp Ser Ser Ala Tyr Tyr Ala Asp Ser Val
50 55 60

Lys Gly Arg Phe Thr Ile Ser Arg Asp Asn Ala Lys Asn Thr Val Tyr
65 70 75 80

Leu Arg Met Asn Ser Leu Lys Pro Glu Asp Thr Ala Val Tyr Tyr Cys
85 90 95

Ala Ala Pro Arg Ser Asp Cys Phe His Tyr Gly Glu Asn Asp Tyr Trp
100 105 110

Gly Gln Gly Thr Gln Val Thr Val Ser Ser
115 120

<210> SEQ ID NO 16
<211> LENGTH: 122
<212> TYPE: PRT
<213> ORGANISM: Artificial Sequence
<220> FEATURE:
<223> OTHER INFORMATION: single-domain antibody

<400> SEQUENCE: 16

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Gly Leu Tyr
            20                  25                  30

Ala Ile Ala Trp Phe Arg Gln Ala Pro Gly Lys Glu Arg Glu Trp Val
        35                  40                  45

Ser Cys Ile Glu Lys Ser Asp Ser Ser Ala Tyr Tyr Ala Asp Ser Val
    50                  55                  60

Lys Gly Arg Phe Thr Val Ser Arg Asp Asn Ala Lys Asn Thr Val Asp
65                  70                  75                  80

Leu Gln Met Asn Arg Leu Ser Pro Glu Asp Thr Ala Val Tyr Tyr Cys
                85                  90                  95

Ala Ala Pro Gln Ser Asp Cys Phe His Tyr Lys Glu Asn Asp Tyr Trp
            100                 105                 110

Gly Gln Gly Thr Gln Val Thr Val Ser Ser
        115                 120
```

<210> SEQ ID NO 17
<211> LENGTH: 121
<212> TYPE: PRT
<213> ORGANISM: Artificial Sequence
<220> FEATURE:
<223> OTHER INFORMATION: single-domain antibody

<400> SEQUENCE: 17

```
Gln Val Gln Leu Gln Glu Ser Gly Gly Gly Leu Val Gln Val Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Leu
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Leu Tyr Thr Gly Asp Asp Tyr Trp Gly
            100                 105                 110

Gln Gly Thr Gln Val Thr Val Ser Ser
        115                 120
```

<210> SEQ ID NO 18
<211> LENGTH: 121
<212> TYPE: PRT
<213> ORGANISM: Artificial Sequence
<220> FEATURE:
<223> OTHER INFORMATION: single-domain antibody

<400> SEQUENCE: 18

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Ser Leu Gly Leu Tyr
20 25 30

Ala Ile Gly Trp Phe Arg Gln Ala Pro Gly Lys Glu Arg Glu Trp Val
35 40 45

Ser Cys Ile Met Ser Ser Asp Ser Ser Ala Tyr Tyr Ala Asp Ser Val
50 55 60

Lys Gly Arg Phe Thr Val Ser Arg Asp Asn Ala Lys Asn Thr Val Tyr
65 70 75 80

Leu Gln Met Thr Asn Leu Lys Pro Glu Asp Thr Ala Val Tyr Leu Cys
85 90 95

Gly Ala Pro Arg Asp Cys Ser Arg Tyr Ser Ser Asp Asp Tyr Trp Gly
100 105 110

Gln Gly Thr Gln Val Thr Val Ser Ser
115 120

<210> SEQ ID NO 19
<211> LENGTH: 121
<212> TYPE: PRT
<213> ORGANISM: Artificial Sequence
<220> FEATURE:
<223> OTHER INFORMATION: single-domain antibody

<400> SEQUENCE: 19

Gln Val Gln Leu Gln Glu Ser Gly Gly Ala Leu Val Gln Ala Gly Gly
1 5 10 15

Ser Leu Arg Leu Ser Cys Ala Ala Ser Gly Phe Thr Phe Asp Asp Tyr
20 25 30

Ala Ile Gly Trp Phe Arg Gln Ala Pro Gly Lys Glu Arg Glu Gly Val
35 40 45

Leu Cys Ile Ser Ser Ser Gly Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Thr Asn Leu Lys Pro Glu Asp Thr Ala Val Tyr Leu Cys
85 90 95

Gly Ala Pro Arg Asp Cys Ser Arg Tyr Ser Ser Asp Asp Tyr Trp Gly
100 105 110

Gln Gly Thr Gln Val Thr Val Ser Ser
115 120

<210> SEQ ID NO 20
<211> LENGTH: 121
<212> TYPE: PRT
<213> ORGANISM: Artificial Sequence
<220> FEATURE:
<223> OTHER INFORMATION: single-domain antibody

<400> SEQUENCE: 20

Gln Val Gln Leu Gln Glu Ser Gly Gly Gly Leu Val Gln Val Gly Gly
1 5 10 15

Ser Leu Arg Leu Ser Cys Ala Ala Ser Gly Phe Thr Phe Asp Asp Tyr
20 25 30

Ala Ile Gly Trp Phe Arg Gln Ala Pro Gly Lys Glu Arg Glu Gly Val
35 40 45

Leu Cys Ile Ser Ser Ser Gly Gly Ser Thr Tyr Tyr Ala Asp Ser Val
50 55 60

```
Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Leu Tyr Thr Gly Asp Asp Tyr Trp Gly
            100                 105                 110

Pro Gly Thr Gln Val Thr Val Ser Ser
        115                 120


<210> SEQ ID NO 21
<211> LENGTH: 121
<212> TYPE: PRT
<213> ORGANISM: Artificial Sequence
<220> FEATURE:
<223> OTHER INFORMATION: single-domain antibody

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Tyr Tyr Thr Ser Asp Asp Tyr Trp Gly
            100                 105                 110

Gln Gly Thr Gln Val Thr Val Ser Ser
        115                 120


<210> SEQ ID NO 22
<211> LENGTH: 121
<212> TYPE: PRT
<213> ORGANISM: Artificial Sequence
<220> FEATURE:
<223> OTHER INFORMATION: single-domain antibody

<400> SEQUENCE: 22

Gln Val Gln Leu Gln Glu Ser Gly Gly Ala Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Leu Cys Ile Ser Ser Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Asn Leu Lys Pro Glu Asp Thr Ala Val Tyr Leu Cys
                85                  90                  95

Gly Ala Pro Arg Asp Cys Ser Arg Tyr Ser Ser Asp Asp Tyr Trp Gly
            100                 105                 110

Gln Gly Thr Gln Val Thr Val Ser Ser
```

115 120

<210> SEQ ID NO 23
<211> LENGTH: 114
<212> TYPE: PRT
<213> ORGANISM: Artificial Sequence
<220> FEATURE:
<223> OTHER INFORMATION: single-domain antibody

<400> SEQUENCE: 23

Gln Val Gln Leu Gln Glu Ser Gly Gly Gly Leu Val Gln Ala Gly Gly
1 5 10 15

Ser Leu Arg Leu Ser Cys Ala Ala Ser Gly Ser Phe Asn Ala Met Gly
20 25 30

Trp Trp Arg Gln Ala Pro Gly Lys Gln Arg Glu Phe Val Ala Ile Ile
35 40 45

Thr Arg Asp Gly Ser Thr Asn Leu Ala Asp Ser Val Lys Gly Arg Phe
50 55 60

Thr Ile Ser Ser Asp Asn Ala Lys Asn Thr Trp Phe Leu Gln Met Asn
65 70 75 80

Ser Leu Lys Pro Glu Asp Thr Ala Val Tyr Tyr Cys Ser Ala Ser Asp
85 90 95

Tyr Gly Ser Ser Leu Tyr Tyr Trp Gly Gln Gly Thr Gln Val Thr Val
100 105 110

Ser Ser

<210> SEQ ID NO 24
<211> LENGTH: 125
<212> TYPE: PRT
<213> ORGANISM: Artificial Sequence
<220> FEATURE:
<223> OTHER INFORMATION: single-domain antibody

<400> SEQUENCE: 24

Gln Val Gln Leu Gln Glu Ser Gly Gly Gly Leu Val Gln Ala Gly Gly
1 5 10 15

Ser Leu Arg Leu Ser Cys Ala Ala Ser Gly Gly Thr Phe Ser Ile Thr
20 25 30

Ala Met Gly Trp Tyr Arg Gln Ala Pro Gly Gln Gln Arg Glu Leu Val
35 40 45

Ala Ala Ile Ala Ser Gly Asp Gly Ala Thr Asn Tyr Ala Asp Phe Val
50 55 60

Lys Gly Arg Phe Thr Ile Ser Arg Asp Asn Ala Lys Asn Thr Met Phe
65 70 75 80

Leu Gln Met Asn Ser Leu Lys Pro Glu Asp Ser Ala Val Tyr Tyr Cys
85 90 95

Tyr Ala Arg Thr Gly Tyr Gly Ser Ser Trp Pro Met Gly His Glu Tyr
100 105 110

Asp Tyr Trp Gly Gln Gly Thr Gln Val Thr Val Ser Ser
115 120 125

<210> SEQ ID NO 25
<211> LENGTH: 115
<212> TYPE: PRT
<213> ORGANISM: Artificial Sequence
<220> FEATURE:
<223> OTHER INFORMATION: single-domain antibody

<400> SEQUENCE: 25

Gln Val Gln Leu Gln Glu Ser Gly Gly Gly Leu Val Gln Pro Gly Glu
1               5                   10                  15

Ser Leu Arg Leu Ser Cys Asp Ser Gly Arg Ile Phe Ser Tyr Asn Phe
            20                  25                  30

Met Gly Trp Tyr Arg Gln Ala Pro Gly Lys Gln Arg Glu Leu Val Ala
        35                  40                  45

Ser Ile Thr Trp Gly Gly Thr Ile Lys Tyr Ala Asp Ser Val Lys Gly
    50                  55                  60

Arg Phe Thr Ile Ser Arg His Asp Ala Glu Asn Thr Val Tyr Leu Gln
65                  70                  75                  80

Met Asn Ser Leu Lys Ser Glu Asp Thr Ala Val Tyr Tyr Cys His Ala
                85                  90                  95

Ala Thr Asp Thr Gly Val Ile Tyr Trp Gly Gln Gly Thr Gln Val Thr
            100                 105                 110

Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: single-domain antibody

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Leu Ser Gly Tyr
            20                  25                  30

Val Met Gly Trp Phe Arg Gln Ala Ser Gly Lys Glu Arg Glu Leu Val
        35                  40                  45

Ala Ala Ile Ser Ser Gly Gly Ser Thr Tyr Tyr Glu Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Ala
                85                  90                  95

Ala Asp Pro Arg Arg Leu Thr Gly Leu Tyr Asp Tyr Trp Gly Gln Gly
            100                 105                 110

Thr Gln Val Thr Val Ser Ser
        115

<210> SEQ ID NO 27
<211> LENGTH: 117
<212> TYPE: PRT
<213> ORGANISM: Artificial Sequence
<220> FEATURE:
<223> OTHER INFORMATION: single-domain antibody

<400> SEQUENCE: 27

Gln Val Gln Leu Gln Glu Ser Gly Gly Gly Leu Val Glu Ala Gly Gly
1               5                   10                  15

Ser Leu Arg Leu Ser Cys Ala Ala Ser Gly Ser Ile Phe Ser Ile Asn
            20                  25                  30

Val Met Gly Trp Tyr Arg Gln Ala Pro Gly Lys Gln Arg Glu Leu Val
        35                  40                  45

Ala Val Ile Thr Ser Asp Tyr Ser Thr Asn Tyr Ala Asp Ser Val Lys
    50                  55                  60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr His Cys Ala
85 90 95

Ala Thr Gly Tyr Gly Ser Ser Pro Trp Tyr Trp Gly Gln Gly Thr Gln
100 105 110

Val Thr Val Ser Ser
115

<210> SEQ ID NO 28
<211> LENGTH: 125
<212> TYPE: PRT
<213> ORGANISM: Artificial Sequence
<220> FEATURE:
<223> OTHER INFORMATION: single-domain antibody

<400> SEQUENCE: 28

Gln Val Gln Leu Gln Glu Ser Gly Gly Gly Leu Val Gln Ala Gly Asp
1 5 10 15

Ser Leu Arg Leu Ser Cys Ala Ala Ser Gly Ser Thr Phe Gly Ile Thr
20 25 30

Ala Met Gly Trp Tyr Arg Gln Pro Pro Gly Lys Gln Arg Glu Leu Val
35 40 45

Ala Ala Ile Ile Met Ser Asp Gly Asp Thr Asn Tyr Gln Asp Ser Val
50 55 60

Lys Gly Arg Phe Thr Ile Ser Arg Asp Asn Ala Lys Asn Thr Met Tyr
65 70 75 80

Leu Gln Met Asn Ser Leu Lys Leu Glu Asp Thr Ala Val Tyr Tyr Cys
85 90 95

Tyr Ala Arg Thr Gly Tyr Gly Ser Gly Arg Leu Met Gly His Glu Tyr
100 105 110

Asp Tyr Trp Gly Gln Gly Thr Gln Val Thr Val Ser Ser
115 120 125

<210> SEQ ID NO 29
<211> LENGTH: 125
<212> TYPE: PRT
<213> ORGANISM: Artificial Sequence
<220> FEATURE:
<223> OTHER INFORMATION: single-domain antibody

<400> SEQUENCE: 29

Gln Val Gln Leu Gln Glu Ser Gly Gly Gly Leu Val Gln Pro Gly Gly
1 5 10 15

Ser Leu Arg Leu Ser Cys Ala Ala Ser Gly Ser Thr Phe Ser Ile Ser
20 25 30

Ala Met Gly Trp Tyr Arg Gln Pro Pro Gly Lys Gln Arg Glu Leu Val
35 40 45

Ala Leu Ile Ile Met Ser Asp Gly Asp Thr Asn Tyr Gln Asp Ser Val
50 55 60

Lys Gly Arg Phe Thr Ile Ser Arg Asp Asn Ala Asn Asn Thr Met Tyr
65 70 75 80

Leu Gln Met Asn Ser Leu Lys Leu Glu Asp Thr Ala Val Tyr Tyr Cys
85 90 95

Tyr Ala Arg Thr Gly Tyr Gly Ser Gly Arg Leu Met Gly His Glu Tyr
100 105 110

Asp Tyr Trp Gly Gln Gly Thr Gln Val Thr Val Ser Ser 115 120 125

<210> SEQ ID NO 30
<211> LENGTH: 125
<212> TYPE: PRT
<213> ORGANISM: Artificial Sequence
<220> FEATURE:
<223> OTHER INFORMATION: single-domain antibody

<400> SEQUENCE: 30

```
Gln Val Gln Leu Gln Glu Ser Gly Gly Gly Leu Val Gln Ala Gly Gly
1               5                   10                  15

Ser Leu Lys Leu Ser Cys Ala Ala Ser Gly Ser Thr Phe Ser Ile Ser
            20                  25                  30

Ala Met Gly Trp Tyr Arg Gln Ala Pro Gly Lys Gln Arg Glu Leu Val
        35                  40                  45

Ala Ala Ile Val Ile Gly Asp Gly Asp Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Tyr Ala Arg Thr Gly Tyr Gly Ser Ser Trp Leu Met Gly His Glu Tyr
            100                 105                 110

Asp Tyr Trp Gly Gln Gly Thr Gln Val Thr Val Ser Ser
        115                 120                 125
```

<210> SEQ ID NO 31
<211> LENGTH: 125
<212> TYPE: PRT
<213> ORGANISM: Artificial Sequence
<220> FEATURE:
<223> OTHER INFORMATION: single-domain antibody

<400> SEQUENCE: 31

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Ala Met Gly Trp Tyr Arg Gln Ala Pro Gly Gln Gln Arg Glu Leu Val
        35                  40                  45

Ala Ala Ile Ala Ser Gly Asp Gly Ala Thr Asn Tyr Ala Asp Phe Val
    50                  55                  60

Lys Gly Arg Phe Thr Ile Ser Arg Asp Asn Ala Lys Asn Thr Met Phe
65                  70                  75                  80

Leu Gln Met Asn Ser Leu Lys Pro Glu Asp Ser Ala Val Tyr Tyr Cys
                85                  90                  95

Tyr Ala Arg Thr Gly Tyr Gly Ser Ser Trp Leu Met Gly His Glu Tyr
            100                 105                 110

Asp Tyr Trp Gly Gln Gly Thr Gln Val Thr Val Ser Ser
        115                 120                 125
```

<210> SEQ ID NO 32
<211> LENGTH: 125
<212> TYPE: PRT
<213> ORGANISM: Artificial Sequence
<220> FEATURE:
<223> OTHER INFORMATION: single-domain antibody

<400> SEQUENCE: 32

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Ser Thr Phe Ser Ile Thr
            20                  25                  30

Ala Met Gly Trp Tyr Arg Gln Pro Pro Gly Lys Gln Arg Glu Leu Val
        35                  40                  45

Ala Ala Ile Ile Met Ser Asp Gly Asp Thr Asn Tyr Gln Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Leu Glu Asp Thr Ala Val Tyr Tyr Cys
                85                  90                  95

Tyr Ala Arg Thr Gly Tyr Gly Ser Gly Arg Leu Met Gly His Glu Tyr
            100                 105                 110

Asp Tyr Trp Gly Gln Gly Thr Gln Val Thr Val Ser Ser
        115                 120                 125


<210> SEQ ID NO 33
<211> LENGTH: 125
<212> TYPE: PRT
<213> ORGANISM: Artificial Sequence
<220> FEATURE:
<223> OTHER INFORMATION: single-domain antibody

<400> SEQUENCE: 33

Gln Val Gln Leu Gln Glu Ser Gly Gly Gly Leu Val Gln Ala Gly Asp
1               5                   10                  15

Ser Leu Arg Leu Ser Cys Ala Ala Ser Gly Ser Thr Phe Ser Ile Thr
            20                  25                  30

Ala Met Gly Trp Tyr Arg Gln Pro Pro Gly Lys Gln Arg Glu Leu Val
        35                  40                  45

Ala Ala Ile Ile Met Ser Asp Gly Asp Thr Asn Tyr Gln Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Tyr Ala Arg Thr Gly Tyr Gly Ser Gly Trp Leu Glu Gly His Glu Tyr
            100                 105                 110

Asp Tyr Trp Gly Gln Gly Thr Gln Val Thr Val Ser Ser
        115                 120                 125


<210> SEQ ID NO 34
<211> LENGTH: 125
<212> TYPE: PRT
<213> ORGANISM: Artificial Sequence
<220> FEATURE:
<223> OTHER INFORMATION: single-domain antibody

<400> SEQUENCE: 34

Gln Val Gln Leu Gln Glu Ser Gly Gly Gly Leu Val Gln Ala Gly Asp
1               5                   10                  15

Ser Leu Arg Leu Ser Cys Ala Ala Ser Gly Ser Thr Phe Ser Ile Thr
            20                  25                  30

Ala Met Gly Trp Tyr Arg Gln Pro Pro Gly Lys Gln Arg Glu Leu Val
        35                  40                  45

Ala Ser Ile Ile Thr Gly Asp Gly Asp Thr Asn Tyr Ala Asp Ser Val
```

```
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Tyr Ala Arg Thr Gly Tyr Gly Ser Ser Trp Leu Met Gly His Glu Tyr
            100                 105                 110

Asp Tyr Trp Gly Gln Gly Thr Gln Val Thr Val Ser Ser
        115                 120                 125


<210> SEQ ID NO 35
<211> LENGTH: 125
<212> TYPE: PRT
<213> ORGANISM: Artificial Sequence
<220> FEATURE:
<223> OTHER INFORMATION: single-domain antibody

<400> SEQUENCE: 35

Gln Val Gln Leu Gln Glu Ser Gly Gly Gly Leu Val Gln Ala Gly Asp
1               5                   10                  15

Ser Leu Arg Leu Ser Cys Ala Ala Ser Gly Ser Thr Phe Ser Ile Val
            20                  25                  30

Ala Met Gly Trp Tyr Arg Gln Ala Pro Gly Lys Gln Arg Glu Leu Val
        35                  40                  45

Ala Ser Ile Ile Thr Gly Asp Gly Asp Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Tyr Ala Arg Thr Gly Tyr Gly Ser Ser Trp Leu Met Gly His Glu Tyr
            100                 105                 110

Asp Tyr Trp Gly Gln Gly Thr Gln Val Thr Val Ser Ser
        115                 120                 125


<210> SEQ ID NO 36
<211> LENGTH: 120
<212> TYPE: PRT
<213> ORGANISM: Artificial Sequence
<220> FEATURE:
<223> OTHER INFORMATION: single-domain antibody

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Ala Ala Ser Arg Ser Ile Phe Ser Ser Tyr
            20                  25                  30

Val Met Ala Trp Tyr Arg Gln Ala Pro Gly Lys Glu Arg Glu Leu Val
        35                  40                  45

Ala Leu Ile Arg Tyr Gly Gly Ser Thr Asp Tyr Ala Asp Ser Val Lys
    50                  55                  60

Gly Arg Phe Thr Ile Ser Arg Asp Asn Ser Lys Asn Thr Leu Ile Leu
65                  70                  75                  80

Gln Met Asn Ser Leu Lys Pro Glu Asp Thr Ala Met Tyr Tyr Cys Ala
                85                  90                  95

Ala Ser Lys Ser Ala Tyr Ile Phe Asp Asp Arg Asp Tyr Trp Gly Gln
            100                 105                 110
```

```
Gly Thr Gln Val Thr Val Ser Ser
        115                 120


<210> SEQ ID NO 37
<211> LENGTH: 116
<212> TYPE: PRT
<213> ORGANISM: Artificial Sequence
<220> FEATURE:
<223> OTHER INFORMATION: single-domain antibody

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gln Arg Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys His
                85                  90                  95

Ile Gly Pro Glu Pro Arg Tyr Gly Tyr Trp Gly Gln Gly Thr Leu Val
            100                 105                 110

Thr Val Ser Ser
        115


<210> SEQ ID NO 38
<211> LENGTH: 116
<212> TYPE: PRT
<213> ORGANISM: Artificial Sequence
<220> FEATURE:
<223> OTHER INFORMATION: single-domain antibody

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Ala Ile Phe Arg Ile Asn
            20                  25                  30

Thr Gly Ala Trp Tyr Arg Gln Ala Pro Gly Lys Gly Leu Glu Leu Val
        35                  40                  45

Ala Ser Leu Thr Thr Tyr Gly Lys Thr Thr Tyr Ala Asp Phe Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys His
                85                  90                  95

Ile Gly Pro Glu Pro Arg Tyr Gly Tyr Trp Gly Gln Gly Thr Leu Val
            100                 105                 110

Thr Val Ser Ser
        115


<210> SEQ ID NO 39
<211> LENGTH: 125
<212> TYPE: PRT
<213> ORGANISM: Artificial Sequence
<220> FEATURE:
<223> OTHER INFORMATION: single-domain antibody
```

<400> SEQUENCE: 39

Gln Val Gln Leu Val Glu Ser Gly Gly Gly Val Val Gln Pro Gly Arg
1 5 10 15

Ser Leu Arg Leu Ser Cys Ala Ala Ser Gly Ser Thr Phe Ser Ile Val
20 25 30

Ala Met Gly Trp Tyr Arg Gln Ala Pro Gly Lys Gln Arg Glu Leu Val
35 40 45

Ala Ser Ile Ile Thr Gly Asp Gly Asp Thr Asn Tyr Ala Asp Ser Val
50 55 60

Lys Gly Arg Phe Thr Ile Ser Arg Asp Asn Ser Lys Asn Thr Met Tyr
65 70 75 80

Leu Gln Met Asn Ser Leu Lys Pro Glu Asp Thr Ala Val Tyr Tyr Cys
85 90 95

Tyr Ala Arg Thr Gly Tyr Gly Ser Ser Trp Leu Met Gly His Glu Tyr
100 105 110

Asp Tyr Trp Gly Gln Gly Thr Gln Val Thr Val Ser Ser
115 120 125

<210> SEQ ID NO 40
<211> LENGTH: 125
<212> TYPE: PRT
<213> ORGANISM: Artificial Sequence
<220> FEATURE:
<223> OTHER INFORMATION: single-domain antibody

<400> SEQUENCE: 40

Gln Val Gln Leu Val Glu Ser Gly Gly Gly Val Val Gln Pro Gly Arg
1 5 10 15

Ser Leu Arg Leu Ser Cys Ala Ala Ser Gly Ser Thr Phe Ser Ile Val
20 25 30

Ala Met Gly Trp Tyr Arg Gln Ala Pro Gly Lys Gly Leu Glu Leu Val
35 40 45

Ala Ser Ile Ile Thr Gly Asp Gly Asp Thr Asn Tyr Ala Asp Ser Val
50 55 60

Lys Gly Arg Phe Thr Ile Ser Arg Asp Asn Ser Lys Asn Thr Met Tyr
65 70 75 80

Leu Gln Met Asn Ser Leu Arg Ala Glu Asp Thr Ala Val Tyr Tyr Cys
85 90 95

Tyr Ala Arg Thr Gly Tyr Gly Ser Ser Trp Leu Met Gly His Glu Tyr
100 105 110

Asp Tyr Trp Gly Gln Gly Thr Gln Val Thr Val Ser Ser
115 120 125

<210> SEQ ID NO 41
<211> LENGTH: 13
<212> TYPE: PRT
<213> ORGANISM: Artificial Sequence
<220> FEATURE:
<223> OTHER INFORMATION: CDR

<400> SEQUENCE: 41

Ala Ala Ser Gly Ala Ile Phe Arg Ile Asn Thr Gly Ala
1 5 10

<210> SEQ ID NO 42
<211> LENGTH: 13
<212> TYPE: PRT
<213> ORGANISM: Artificial Sequence
<220> FEATURE:

<223> OTHER INFORMATION: CDR

<400> SEQUENCE: 42

Ala Ala Ser Gly Ala Ile Phe Arg Ile Asn Thr Gly Ala
1 5 10

<210> SEQ ID NO 43
<211> LENGTH: 13
<212> TYPE: PRT
<213> ORGANISM: Artificial Sequence
<220> FEATURE:
<223> OTHER INFORMATION: CDR

<400> SEQUENCE: 43

Ala Ala Ser Gly Ala Ile Phe Arg Ile Asn Thr Gly Ala
1 5 10

<210> SEQ ID NO 44
<211> LENGTH: 13
<212> TYPE: PRT
<213> ORGANISM: Artificial Sequence
<220> FEATURE:
<223> OTHER INFORMATION: CDR

<400> SEQUENCE: 44

Ala Ala Ser Gly Phe Thr Phe Asp Asp Tyr Ala Ile Gly
1 5 10

<210> SEQ ID NO 45
<211> LENGTH: 13
<212> TYPE: PRT
<213> ORGANISM: Artificial Sequence
<220> FEATURE:
<223> OTHER INFORMATION: CDR

<400> SEQUENCE: 45

Ala Ala Ser Gly Phe Thr Leu Asp Tyr Tyr Ala Ile Gly
1 5 10

<210> SEQ ID NO 46
<211> LENGTH: 13
<212> TYPE: PRT
<213> ORGANISM: Artificial Sequence
<220> FEATURE:
<223> OTHER INFORMATION: CDR

<400> SEQUENCE: 46

Ala Ala Ser Gly Ala Ile Phe Arg Ile Asn Thr Gly Ala
1 5 10

<210> SEQ ID NO 47
<211> LENGTH: 13
<212> TYPE: PRT
<213> ORGANISM: Artificial Sequence
<220> FEATURE:
<223> OTHER INFORMATION: CDR

<400> SEQUENCE: 47

Ala Ala Ser Gly Phe Thr Phe Asp Asp Tyr Ala Ile Gly
1 5 10

<210> SEQ ID NO 48
<211> LENGTH: 13
<212> TYPE: PRT
<213> ORGANISM: Artificial Sequence
<220> FEATURE:
<223> OTHER INFORMATION: CDR

<400> SEQUENCE: 48

Ala Ala Ser Gly Phe Thr Phe Asp Asp Tyr Ala Ile Gly
1 5 10

<210> SEQ ID NO 49
<211> LENGTH: 13
<212> TYPE: PRT
<213> ORGANISM: Artificial Sequence
<220> FEATURE:
<223> OTHER INFORMATION: CDR

<400> SEQUENCE: 49

Ala Ala Ser Gly Phe Thr Phe Asp Asp Tyr Ala Ile Gly
1 5 10

<210> SEQ ID NO 50
<211> LENGTH: 13
<212> TYPE: PRT
<213> ORGANISM: Artificial Sequence
<220> FEATURE:
<223> OTHER INFORMATION: CDR

<400> SEQUENCE: 50

Ala Ala Ser Gly Phe Ser Leu Gly Leu Tyr Ala Ile Gly
1 5 10

<210> SEQ ID NO 51
<211> LENGTH: 13
<212> TYPE: PRT
<213> ORGANISM: Artificial Sequence
<220> FEATURE:
<223> OTHER INFORMATION: CDR

<400> SEQUENCE: 51

Ala Ala Ser Gly Phe Thr Phe Asp Asp Tyr Ala Ile Gly
1 5 10

<210> SEQ ID NO 52
<211> LENGTH: 13
<212> TYPE: PRT
<213> ORGANISM: Artificial Sequence
<220> FEATURE:
<223> OTHER INFORMATION: CDR

<400> SEQUENCE: 52

Ala Ala Ser Gly Phe Thr Phe Asp Asp Tyr Ala Ile Gly
1 5 10

<210> SEQ ID NO 53
<211> LENGTH: 13
<212> TYPE: PRT
<213> ORGANISM: Artificial Sequence
<220> FEATURE:
<223> OTHER INFORMATION: CDR

<400> SEQUENCE: 53

Ala Ala Ser Gly Phe Ser Leu Gly Leu Tyr Ala Ile Gly
1 5 10

<210> SEQ ID NO 54
<211> LENGTH: 13
<212> TYPE: PRT
<213> ORGANISM: Artificial Sequence
<220> FEATURE:
<223> OTHER INFORMATION: CDR

<400> SEQUENCE: 54

Ala Ala Ser Gly Phe Ser Leu Asp Tyr Tyr Ala Ile Gly
1 5 10

<210> SEQ ID NO 55
<211> LENGTH: 13
<212> TYPE: PRT
<213> ORGANISM: Artificial Sequence
<220> FEATURE:
<223> OTHER INFORMATION: CDR

<400> SEQUENCE: 55

Ala Ala Ser Gly Phe Ser Leu Asp Tyr Tyr Ala Ile Gly
1 5 10

<210> SEQ ID NO 56
<211> LENGTH: 13
<212> TYPE: PRT
<213> ORGANISM: Artificial Sequence
<220> FEATURE:
<223> OTHER INFORMATION: CDR

<400> SEQUENCE: 56

Ala Ala Ser Gly Phe Ser Leu Gly Leu Tyr Ala Ile Ala
1 5 10

<210> SEQ ID NO 57
<211> LENGTH: 13
<212> TYPE: PRT
<213> ORGANISM: Artificial Sequence
<220> FEATURE:
<223> OTHER INFORMATION: CDR

<400> SEQUENCE: 57

Ala Ala Ser Gly Phe Thr Phe Asp Asp Tyr Ala Ile Gly
1 5 10

<210> SEQ ID NO 58
<211> LENGTH: 13
<212> TYPE: PRT
<213> ORGANISM: Artificial Sequence
<220> FEATURE:
<223> OTHER INFORMATION: CDR

<400> SEQUENCE: 58

Ala Ala Ser Gly Phe Ser Leu Gly Leu Tyr Ala Ile Gly
1 5 10

<210> SEQ ID NO 59
<211> LENGTH: 13
<212> TYPE: PRT
<213> ORGANISM: Artificial Sequence
<220> FEATURE:
<223> OTHER INFORMATION: CDR

<400> SEQUENCE: 59

Ala Ala Ser Gly Phe Thr Phe Asp Asp Tyr Ala Ile Gly
1 5 10

<210> SEQ ID NO 60
<211> LENGTH: 13
<212> TYPE: PRT
<213> ORGANISM: Artificial Sequence
<220> FEATURE:
<223> OTHER INFORMATION: CDR

<400> SEQUENCE: 60

Ala Ala Ser Gly Phe Thr Phe Asp Asp Tyr Ala Ile Gly
1 5 10

<210> SEQ ID NO 61
<211> LENGTH: 13
<212> TYPE: PRT
<213> ORGANISM: Artificial Sequence
<220> FEATURE:
<223> OTHER INFORMATION: CDR

<400> SEQUENCE: 61

Ala Ala Ser Gly Phe Thr Phe Asp Asp Tyr Ala Ile Gly
1 5 10

<210> SEQ ID NO 62
<211> LENGTH: 13
<212> TYPE: PRT
<213> ORGANISM: Artificial Sequence
<220> FEATURE:
<223> OTHER INFORMATION: CDR

<400> SEQUENCE: 62

Ala Ala Ser Gly Phe Thr Phe Asp Asp Tyr Ala Ile Gly
1 5 10

<210> SEQ ID NO 63
<211> LENGTH: 10
<212> TYPE: PRT
<213> ORGANISM: Artificial Sequence
<220> FEATURE:
<223> OTHER INFORMATION: CDR

<400> SEQUENCE: 63

Ala Ala Ser Gly Ser Phe Asn Ala Met Gly
1 5 10

<210> SEQ ID NO 64
<211> LENGTH: 13
<212> TYPE: PRT
<213> ORGANISM: Artificial Sequence
<220> FEATURE:
<223> OTHER INFORMATION: CDR

<400> SEQUENCE: 64

Ala Ala Ser Gly Gly Thr Phe Ser Ile Thr Ala Met Gly
1 5 10

<210> SEQ ID NO 65
<211> LENGTH: 12
<212> TYPE: PRT
<213> ORGANISM: Artificial Sequence
<220> FEATURE:
<223> OTHER INFORMATION: CDR

<400> SEQUENCE: 65

Asp Ser Gly Arg Ile Phe Ser Tyr Asn Phe Met Gly
1 5 10

<210> SEQ ID NO 66
<211> LENGTH: 13
<212> TYPE: PRT
<213> ORGANISM: Artificial Sequence
<220> FEATURE:
<223> OTHER INFORMATION: CDR

<400> SEQUENCE: 66

Ala Ala Ser Gly Arg Thr Leu Ser Gly Tyr Val Met Gly
1 5 10

<210> SEQ ID NO 67
<211> LENGTH: 13
<212> TYPE: PRT
<213> ORGANISM: Artificial Sequence
<220> FEATURE:
<223> OTHER INFORMATION: CDR

<400> SEQUENCE: 67

Ala Ala Ser Gly Ser Ile Phe Ser Ile Asn Val Met Gly
1 5 10

<210> SEQ ID NO 68
<211> LENGTH: 13
<212> TYPE: PRT
<213> ORGANISM: Artificial Sequence
<220> FEATURE:
<223> OTHER INFORMATION: CDR

<400> SEQUENCE: 68

Ala Ala Ser Gly Ser Thr Phe Gly Ile Thr Ala Met Gly
1 5 10

<210> SEQ ID NO 69
<211> LENGTH: 13
<212> TYPE: PRT
<213> ORGANISM: Artificial Sequence
<220> FEATURE:
<223> OTHER INFORMATION: CDR

<400> SEQUENCE: 69

Ala Ala Ser Gly Ser Thr Phe Ser Ile Ser Ala Met Gly
1 5 10

<210> SEQ ID NO 70
<211> LENGTH: 13
<212> TYPE: PRT
<213> ORGANISM: Artificial Sequence
<220> FEATURE:
<223> OTHER INFORMATION: CDR

<400> SEQUENCE: 70

Ala Ala Ser Gly Ser Thr Phe Ser Ile Ser Ala Met Gly
1 5 10

<210> SEQ ID NO 71
<211> LENGTH: 13
<212> TYPE: PRT
<213> ORGANISM: Artificial Sequence
<220> FEATURE:
<223> OTHER INFORMATION: CDR

<400> SEQUENCE: 71

Ala Ala Ser Gly Ser Thr Phe Ser Ile Thr Ala Met Gly
1 5 10

<210> SEQ ID NO 72
<211> LENGTH: 13
<212> TYPE: PRT
<213> ORGANISM: Artificial Sequence
<220> FEATURE:
<223> OTHER INFORMATION: CDR

<400> SEQUENCE: 72

Ala Ala Ser Gly Ser Thr Phe Ser Ile Thr Ala Met Gly 1 5 10

<210> SEQ ID NO 73
<211> LENGTH: 13
<212> TYPE: PRT
<213> ORGANISM: Artificial Sequence
<220> FEATURE:
<223> OTHER INFORMATION: CDR

<400> SEQUENCE: 73

Ala Ala Ser Gly Ser Thr Phe Ser Ile Thr Ala Met Gly
1 5 10

<210> SEQ ID NO 74
<211> LENGTH: 13
<212> TYPE: PRT
<213> ORGANISM: Artificial Sequence
<220> FEATURE:
<223> OTHER INFORMATION: CDR

<400> SEQUENCE: 74

Ala Ala Ser Gly Ser Thr Phe Ser Ile Thr Ala Met Gly
1 5 10

<210> SEQ ID NO 75
<211> LENGTH: 13
<212> TYPE: PRT
<213> ORGANISM: Artificial Sequence
<220> FEATURE:
<223> OTHER INFORMATION: CDR

<400> SEQUENCE: 75

Ala Ala Ser Gly Ser Thr Phe Ser Ile Val Ala Met Gly
1 5 10

<210> SEQ ID NO 76
<211> LENGTH: 13
<212> TYPE: PRT
<213> ORGANISM: Artificial Sequence
<220> FEATURE:
<223> OTHER INFORMATION: CDR

<400> SEQUENCE: 76

Ala Ala Ser Arg Ser Ile Phe Ser Ser Tyr Val Met Ala
1 5 10

<210> SEQ ID NO 77
<211> LENGTH: 13
<212> TYPE: PRT
<213> ORGANISM: Artificial Sequence
<220> FEATURE:
<223> OTHER INFORMATION: CDR

<400> SEQUENCE: 77

Ala Ala Ser Gly Ala Ile Phe Arg Ile Asn Thr Gly Ala
1 5 10

<210> SEQ ID NO 78
<211> LENGTH: 13
<212> TYPE: PRT
<213> ORGANISM: Artificial Sequence
<220> FEATURE:
<223> OTHER INFORMATION: CDR

<400> SEQUENCE: 78

Ala Ala Ser Gly Ala Ile Phe Arg Ile Asn Thr Gly Ala
1 5 10

<210> SEQ ID NO 79
<211> LENGTH: 13
<212> TYPE: PRT
<213> ORGANISM: Artificial Sequence
<220> FEATURE:
<223> OTHER INFORMATION: CDR

<400> SEQUENCE: 79

```
Ala Ala Ser Gly Ser Thr Phe Ser Ile Val Ala Met Gly
1               5                   10
```

<210> SEQ ID NO 80
<211> LENGTH: 13
<212> TYPE: PRT
<213> ORGANISM: Artificial Sequence
<220> FEATURE:
<223> OTHER INFORMATION: CDR

<400> SEQUENCE: 80

```
Ala Ala Ser Gly Ser Thr Phe Ser Ile Val Ala Met Gly
1               5                   10
```

<210> SEQ ID NO 81
<211> LENGTH: 16
<212> TYPE: PRT
<213> ORGANISM: Artificial Sequence
<220> FEATURE:
<223> OTHER INFORMATION: CDR

<400> SEQUENCE: 81

```
Ser Leu Thr Thr Tyr Gly Lys Thr Thr Tyr Ala Asp Phe Val Lys Gly
1               5                   10                  15
```

<210> SEQ ID NO 82
<211> LENGTH: 16
<212> TYPE: PRT
<213> ORGANISM: Artificial Sequence
<220> FEATURE:
<223> OTHER INFORMATION: CDR

<400> SEQUENCE: 82

```
Ser Leu Thr Thr Tyr Gly Lys Thr Thr Tyr Ala Asp Phe Val Lys Gly
1               5                   10                  15
```

<210> SEQ ID NO 83
<211> LENGTH: 16
<212> TYPE: PRT
<213> ORGANISM: Artificial Sequence
<220> FEATURE:
<223> OTHER INFORMATION: CDR

<400> SEQUENCE: 83

```
Ser Leu Thr Thr Tyr Gly Lys Thr Thr Tyr Ala Asp Phe Val Lys Gly
1               5                   10                  15
```

<210> SEQ ID NO 84
<211> LENGTH: 17
<212> TYPE: PRT
<213> ORGANISM: Artificial Sequence
<220> FEATURE:
<223> OTHER INFORMATION: CDR

<400> SEQUENCE: 84

```
Cys Ile Ser Ser Ser Gly Gly Ser Thr Tyr Tyr Ala Asp Ser Val Lys
1               5                   10                  15
```

Gly

<210> SEQ ID NO 85
<211> LENGTH: 17
<212> TYPE: PRT
<213> ORGANISM: Artificial Sequence
<220> FEATURE:
<223> OTHER INFORMATION: CDR

<400> SEQUENCE: 85

Cys Ile Ser Ser Ser Gly Glu Thr Thr Tyr Tyr Ser Asp Ser Val Lys
1 5 10 15

Gly

<210> SEQ ID NO 86
<211> LENGTH: 16
<212> TYPE: PRT
<213> ORGANISM: Artificial Sequence
<220> FEATURE:
<223> OTHER INFORMATION: CDR

<400> SEQUENCE: 86

Ser Leu Thr Thr Tyr Gly Lys Thr Thr Tyr Ala Asp Phe Val Lys Gly
1 5 10 15

<210> SEQ ID NO 87
<211> LENGTH: 17
<212> TYPE: PRT
<213> ORGANISM: Artificial Sequence
<220> FEATURE:
<223> OTHER INFORMATION: CDR

<400> SEQUENCE: 87

Cys Ile Ser Ser Ser Gly Gly Ser Thr Tyr Tyr Ala Asp Ser Val Lys
1 5 10 15

Gly

<210> SEQ ID NO 88
<211> LENGTH: 17
<212> TYPE: PRT
<213> ORGANISM: Artificial Sequence
<220> FEATURE:
<223> OTHER INFORMATION: CDR

<400> SEQUENCE: 88

Cys Ile Ser Ser Ser Gly Gly Ser Thr Tyr Tyr Ala Asp Ser Val Lys
1 5 10 15

Gly

<210> SEQ ID NO 89
<211> LENGTH: 17
<212> TYPE: PRT
<213> ORGANISM: Artificial Sequence
<220> FEATURE:
<223> OTHER INFORMATION: CDR

<400> SEQUENCE: 89

Cys Ile Ser Ser Ser Gly Gly Ser Thr Tyr Tyr Ala Asp Ser Val Lys
1 5 10 15

Gly

<210> SEQ ID NO 90
<211> LENGTH: 17
<212> TYPE: PRT

<213> ORGANISM: Artificial Sequence
<220> FEATURE:
<223> OTHER INFORMATION: CDR

<400> SEQUENCE: 90

Cys Ile Met Ser Ser Asp Ser Ser Ala Tyr Tyr Ala Asp Ser Val Lys
1 5 10 15

Gly

<210> SEQ ID NO 91
<211> LENGTH: 17
<212> TYPE: PRT
<213> ORGANISM: Artificial Sequence
<220> FEATURE:
<223> OTHER INFORMATION: CDR

<400> SEQUENCE: 91

Cys Ile Ser Ser Ser Gly Gly Ser Thr Tyr Tyr Ala Asp Ser Val Lys
1 5 10 15

Gly

<210> SEQ ID NO 92
<211> LENGTH: 17
<212> TYPE: PRT
<213> ORGANISM: Artificial Sequence
<220> FEATURE:
<223> OTHER INFORMATION: CDR

<400> SEQUENCE: 92

Cys Ile Ser Ser Ser Gly Gly Ser Thr Tyr Tyr Ala Asp Ser Val Lys
1 5 10 15

Gly

<210> SEQ ID NO 93
<211> LENGTH: 17
<212> TYPE: PRT
<213> ORGANISM: Artificial Sequence
<220> FEATURE:
<223> OTHER INFORMATION: CDR

<400> SEQUENCE: 93

Cys Ile Met Ser Ser Asp Ser Ser Ala Tyr Tyr Ala Asp Ser Val Lys
1 5 10 15

Gly

<210> SEQ ID NO 94
<211> LENGTH: 17
<212> TYPE: PRT
<213> ORGANISM: Artificial Sequence
<220> FEATURE:
<223> OTHER INFORMATION: CDR

<400> SEQUENCE: 94

Cys Ile Met Ser Ser Asp Ser Ser Ala Tyr Tyr Ala Asp Ser Val Lys
1 5 10 15

Gly

<210> SEQ ID NO 95
<211> LENGTH: 17
<212> TYPE: PRT
<213> ORGANISM: Artificial Sequence
<220> FEATURE:
<223> OTHER INFORMATION: CDR

<400> SEQUENCE: 95

Cys Ile Thr Ala Ser Asp Ser Ser Ala Tyr Tyr Ala Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: CDR

<400> SEQUENCE: 96

Cys Ile Glu Lys Ser Asp Ser Ser Ala Tyr Tyr Ala Asp Ser Val Lys
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: CDR

<400> SEQUENCE: 97

Cys Ile Ser Ser Ser Gly Gly Ser Thr Tyr Tyr Ala Asp Ser Leu Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: CDR

<400> SEQUENCE: 98

Cys Ile Met Ser Ser Asp Ser Ser Ala Tyr Tyr Ala Asp Ser Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: CDR

<400> SEQUENCE: 99

Cys Ile Ser Ser Ser Gly Gly Ser Thr Tyr Tyr Ala Asp Ser Val Lys
1               5                   10                  15

Gly

<210> SEQ ID NO 100
<211> LENGTH: 17
<212> TYPE: PRT
<213> ORGANISM: Artificial Sequence
<220> FEATURE:
<223> OTHER INFORMATION: CDR

<400> SEQUENCE: 100

Cys Ile Ser Ser Ser Gly Gly Ser Thr Tyr Tyr Ala Asp Ser Val Lys
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: CDR

<400> SEQUENCE: 101

Cys Ile Ser Ser Ser Gly Gly Ser Thr Tyr Tyr Ala Asp Ser Val Lys
1 5 10 15

Gly

<210> SEQ ID NO 102
<211> LENGTH: 17
<212> TYPE: PRT
<213> ORGANISM: Artificial Sequence
<220> FEATURE:
<223> OTHER INFORMATION: CDR

<400> SEQUENCE: 102

Cys Ile Ser Ser Ser Gly Gly Ser Thr Tyr Tyr Ala Asp Ser Val Lys
1 5 10 15

Gly

<210> SEQ ID NO 103
<211> LENGTH: 16
<212> TYPE: PRT
<213> ORGANISM: Artificial Sequence
<220> FEATURE:
<223> OTHER INFORMATION: CDR

<400> SEQUENCE: 103

Ile Ile Thr Arg Asp Gly Ser Thr Asn Leu Ala Asp Ser Val Lys Gly
1 5 10 15

<210> SEQ ID NO 104
<211> LENGTH: 17
<212> TYPE: PRT
<213> ORGANISM: Artificial Sequence
<220> FEATURE:
<223> OTHER INFORMATION: CDR

<400> SEQUENCE: 104

Ala Ile Ala Ser Gly Asp Gly Ala Thr Asn Tyr Ala Asp Phe Val Lys
1 5 10 15

Gly

<210> SEQ ID NO 105
<211> LENGTH: 16
<212> TYPE: PRT
<213> ORGANISM: Artificial Sequence
<220> FEATURE:
<223> OTHER INFORMATION: CDR

<400> SEQUENCE: 105

Ser Ile Thr Trp Gly Gly Thr Ile Lys Tyr Ala Asp Ser Val Lys Gly
1 5 10 15

<210> SEQ ID NO 106
<211> LENGTH: 16
<212> TYPE: PRT
<213> ORGANISM: Artificial Sequence

<220> FEATURE:
<223> OTHER INFORMATION: CDR

<400> SEQUENCE: 106

Ala Ile Ser Ser Gly Gly Ser Thr Tyr Tyr Glu Asp Ser Val Lys Gly
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: CDR

<400> SEQUENCE: 107

Val Ile Thr Ser Asp Tyr Ser Thr Asn Tyr Ala Asp Ser Val Lys Gly
1               5                   10                  15

<210> SEQ ID NO 108
<211> LENGTH: 17
<212> TYPE: PRT
<213> ORGANISM: Artificial Sequence
<220> FEATURE:
<223> OTHER INFORMATION: CDR

<400> SEQUENCE: 108

Ala Ile Ile Met Ser Asp Gly Asp Thr Asn Tyr Gln Asp Ser Val Lys
1               5                   10                  15

Gly

<210> SEQ ID NO 109
<211> LENGTH: 17
<212> TYPE: PRT
<213> ORGANISM: Artificial Sequence
<220> FEATURE:
<223> OTHER INFORMATION: CDR

<400> SEQUENCE: 109

Leu Ile Ile Met Ser Asp Gly Asp Thr Asn Tyr Gln Asp Ser Val Lys
1               5                   10                  15

Gly

<210> SEQ ID NO 110
<211> LENGTH: 17
<212> TYPE: PRT
<213> ORGANISM: Artificial Sequence
<220> FEATURE:
<223> OTHER INFORMATION: CDR

<400> SEQUENCE: 110

Ala Ile Val Ile Gly Asp Gly Asp Thr Asn Tyr Ala Asp Ser Val Lys
1               5                   10                  15

Gly

<210> SEQ ID NO 111
<211> LENGTH: 17
<212> TYPE: PRT
<213> ORGANISM: Artificial Sequence
<220> FEATURE:
<223> OTHER INFORMATION: CDR

<400> SEQUENCE: 111

Ala Ile Ala Ser Gly Asp Gly Ala Thr Asn Tyr Ala Asp Phe Val Lys
1               5                   10                  15

Gly

<210> SEQ ID NO 112
<211> LENGTH: 17
<212> TYPE: PRT
<213> ORGANISM: Artificial Sequence
<220> FEATURE:
<223> OTHER INFORMATION: CDR

<400> SEQUENCE: 112

Ala Ile Ile Met Ser Asp Gly Asp Thr Asn Tyr Gln Asp Ser Val Lys
1 5 10 15

Gly

<210> SEQ ID NO 113
<211> LENGTH: 17
<212> TYPE: PRT
<213> ORGANISM: Artificial Sequence
<220> FEATURE:
<223> OTHER INFORMATION: CDR

<400> SEQUENCE: 113

Ala Ile Ile Met Ser Asp Gly Asp Thr Asn Tyr Gln Asp Ser Val Lys
1 5 10 15

Gly

<210> SEQ ID NO 114
<211> LENGTH: 17
<212> TYPE: PRT
<213> ORGANISM: Artificial Sequence
<220> FEATURE:
<223> OTHER INFORMATION: CDR

<400> SEQUENCE: 114

Ser Ile Ile Thr Gly Asp Gly Asp Thr Asn Tyr Ala Asp Ser Val Lys
1 5 10 15

Gly

<210> SEQ ID NO 115
<211> LENGTH: 17
<212> TYPE: PRT
<213> ORGANISM: Artificial Sequence
<220> FEATURE:
<223> OTHER INFORMATION: CDR

<400> SEQUENCE: 115

Ser Ile Ile Thr Gly Asp Gly Asp Thr Asn Tyr Ala Asp Ser Val Lys
1 5 10 15

Gly

<210> SEQ ID NO 116
<211> LENGTH: 16
<212> TYPE: PRT
<213> ORGANISM: Artificial Sequence
<220> FEATURE:
<223> OTHER INFORMATION: CDR

<400> SEQUENCE: 116

Leu Ile Arg Tyr Gly Gly Ser Thr Asp Tyr Ala Asp Ser Val Lys Gly
1 5 10 15

<210> SEQ ID NO 117
<211> LENGTH: 16
<212> TYPE: PRT

<213> ORGANISM: Artificial Sequence
<220> FEATURE:
<223> OTHER INFORMATION: CDR

<400> SEQUENCE: 117

Ser Leu Thr Thr Tyr Gly Lys Thr Thr Tyr Ala Asp Phe Val Lys Gly
1 5 10 15

<210> SEQ ID NO 118
<211> LENGTH: 16
<212> TYPE: PRT
<213> ORGANISM: Artificial Sequence
<220> FEATURE:
<223> OTHER INFORMATION: CDR

<400> SEQUENCE: 118

Ser Leu Thr Thr Tyr Gly Lys Thr Thr Tyr Ala Asp Phe Val Lys Gly
1 5 10 15

<210> SEQ ID NO 119
<211> LENGTH: 17
<212> TYPE: PRT
<213> ORGANISM: Artificial Sequence
<220> FEATURE:
<223> OTHER INFORMATION: CDR

<400> SEQUENCE: 119

Ser Ile Ile Thr Gly Asp Gly Asp Thr Asn Tyr Ala Asp Ser Val Lys
1 5 10 15

Gly

<210> SEQ ID NO 120
<211> LENGTH: 17
<212> TYPE: PRT
<213> ORGANISM: Artificial Sequence
<220> FEATURE:
<223> OTHER INFORMATION: CDR

<400> SEQUENCE: 120

Ser Ile Ile Thr Gly Asp Gly Asp Thr Asn Tyr Ala Asp Ser Val Lys
1 5 10 15

Gly

<210> SEQ ID NO 121
<211> LENGTH: 10
<212> TYPE: PRT
<213> ORGANISM: Artificial Sequence
<220> FEATURE:
<223> OTHER INFORMATION: CDR

<400> SEQUENCE: 121

His Ile Gly Pro Glu Pro Arg Tyr Gly Tyr
1 5 10

<210> SEQ ID NO 122
<211> LENGTH: 10
<212> TYPE: PRT
<213> ORGANISM: Artificial Sequence
<220> FEATURE:
<223> OTHER INFORMATION: CDR

<400> SEQUENCE: 122

His Ile Gly Pro Glu Pro Arg Tyr Gly Tyr
1 5 10

<210> SEQ ID NO 123
<211> LENGTH: 10
<212> TYPE: PRT
<213> ORGANISM: Artificial Sequence
<220> FEATURE:
<223> OTHER INFORMATION: CDR

<400> SEQUENCE: 123

His Ile Gly Pro Glu Pro Arg Tyr Gly Tyr
1               5                   10

<210> SEQ ID NO 124
<211> LENGTH: 14
<212> TYPE: PRT
<213> ORGANISM: Artificial Sequence
<220> FEATURE:
<223> OTHER INFORMATION: CDR

<400> SEQUENCE: 124

Gly Ala Pro Arg Asp Cys Ser Leu Tyr Thr Gly Asp Asp Tyr
1               5                   10

<210> SEQ ID NO 125
<211> LENGTH: 20
<212> TYPE: PRT
<213> ORGANISM: Artificial Sequence
<220> FEATURE:
<223> OTHER INFORMATION: CDR

<400> SEQUENCE: 125

Gly Ala Glu Leu Leu Gly Ser Gly Glu Gly Cys Tyr Val Trp Ser Arg
1               5                   10                  15

Asp Gly Ser Tyr
            20

<210> SEQ ID NO 126
<211> LENGTH: 10
<212> TYPE: PRT
<213> ORGANISM: Artificial Sequence
<220> FEATURE:
<223> OTHER INFORMATION: CDR

<400> SEQUENCE: 126

His Ile Gly Pro Glu Pro Arg Tyr Gly Tyr
1               5                   10

<210> SEQ ID NO 127
<211> LENGTH: 14
<212> TYPE: PRT
<213> ORGANISM: Artificial Sequence
<220> FEATURE:
<223> OTHER INFORMATION: CDR

<400> SEQUENCE: 127

Gly Ala Pro Arg Asp Cys Ser Arg Tyr Ser Ser Asp Asp Tyr
1               5                   10

<210> SEQ ID NO 128
<211> LENGTH: 14
<212> TYPE: PRT
<213> ORGANISM: Artificial Sequence
<220> FEATURE:
<223> OTHER INFORMATION: CDR

<400> SEQUENCE: 128

Gly Ala Pro Arg Asp Cys Ser Arg Tyr Ser Ser Asp Asp Tyr
1               5                   10

<210> SEQ ID NO 129
<211> LENGTH: 14
<212> TYPE: PRT
<213> ORGANISM: Artificial Sequence
<220> FEATURE:
<223> OTHER INFORMATION: CDR

<400> SEQUENCE: 129

Gly Ala Pro Arg Asp Cys Ser Tyr Tyr Thr Gly Asp Asp Tyr
1 5 10

<210> SEQ ID NO 130
<211> LENGTH: 15
<212> TYPE: PRT
<213> ORGANISM: Artificial Sequence
<220> FEATURE:
<223> OTHER INFORMATION: CDR

<400> SEQUENCE: 130

Ala Ala Pro Gln Ser Asp Cys Phe His Tyr Ser Glu Asn Asp Tyr
1 5 10 15

<210> SEQ ID NO 131
<211> LENGTH: 14
<212> TYPE: PRT
<213> ORGANISM: Artificial Sequence
<220> FEATURE:
<223> OTHER INFORMATION: CDR

<400> SEQUENCE: 131

Gly Ala Pro Arg Asp Cys Ser Arg Tyr Ser Ser Asp Asp Tyr
1 5 10

<210> SEQ ID NO 132
<211> LENGTH: 14
<212> TYPE: PRT
<213> ORGANISM: Artificial Sequence
<220> FEATURE:
<223> OTHER INFORMATION: CDR

<400> SEQUENCE: 132

Gly Ala Pro Arg Asp Cys Ser Arg Tyr Ser Ser Asp Asp Tyr
1 5 10

<210> SEQ ID NO 133
<211> LENGTH: 15
<212> TYPE: PRT
<213> ORGANISM: Artificial Sequence
<220> FEATURE:
<223> OTHER INFORMATION: CDR

<400> SEQUENCE: 133

Ala Ala Pro Gln Ser Asp Cys Phe His Tyr Ser Glu Asn Asp Tyr
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: CDR

<400> SEQUENCE: 134

Thr Ala Pro Arg Ser Asp Cys Phe His Tyr Gly Glu Asn Asp Tyr
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: CDR

<400> SEQUENCE: 135

Ala Ala Pro Arg Ser Asp Cys Phe His Tyr Gly Glu Asn Asp Tyr
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: CDR

<400> SEQUENCE: 136

Ala Ala Pro Gln Ser Asp Cys Phe His Tyr Lys Glu Asn Asp Tyr
1 5 10 15

<210> SEQ ID NO 137
<211> LENGTH: 14
<212> TYPE: PRT
<213> ORGANISM: Artificial Sequence
<220> FEATURE:
<223> OTHER INFORMATION: CDR

<400> SEQUENCE: 137

Gly Ala Pro Arg Asp Cys Ser Leu Tyr Thr Gly Asp Asp Tyr
1 5 10

<210> SEQ ID NO 138
<211> LENGTH: 14
<212> TYPE: PRT
<213> ORGANISM: Artificial Sequence
<220> FEATURE:
<223> OTHER INFORMATION: CDR

<400> SEQUENCE: 138

Gly Ala Pro Arg Asp Cys Ser Arg Tyr Ser Ser Asp Asp Tyr
1 5 10

<210> SEQ ID NO 139
<211> LENGTH: 14
<212> TYPE: PRT
<213> ORGANISM: Artificial Sequence
<220> FEATURE:
<223> OTHER INFORMATION: CDR

<400> SEQUENCE: 139

Gly Ala Pro Arg Asp Cys Ser Arg Tyr Ser Ser Asp Asp Tyr
1 5 10

<210> SEQ ID NO 140
<211> LENGTH: 14
<212> TYPE: PRT
<213> ORGANISM: Artificial Sequence
<220> FEATURE:
<223> OTHER INFORMATION: CDR

<400> SEQUENCE: 140

Gly Ala Pro Arg Asp Cys Ser Leu Tyr Thr Gly Asp Asp Tyr
1 5 10

<210> SEQ ID NO 141
<211> LENGTH: 14
<212> TYPE: PRT
<213> ORGANISM: Artificial Sequence
<220> FEATURE:
<223> OTHER INFORMATION: CDR

<400> SEQUENCE: 141

Gly Ala Pro Arg Asp Cys Ser Tyr Tyr Thr Ser Asp Asp Tyr
1               5                   10

<210> SEQ ID NO 142
<211> LENGTH: 14
<212> TYPE: PRT
<213> ORGANISM: Artificial Sequence
<220> FEATURE:
<223> OTHER INFORMATION: CDR

<400> SEQUENCE: 142

Gly Ala Pro Arg Asp Cys Ser Arg Tyr Ser Ser Asp Asp Tyr
1               5                   10

<210> SEQ ID NO 143
<211> LENGTH: 11
<212> TYPE: PRT
<213> ORGANISM: Artificial Sequence
<220> FEATURE:
<223> OTHER INFORMATION: CDR

<400> SEQUENCE: 143

Ser Ala Ser Asp Tyr Gly Ser Ser Leu Tyr Tyr
1               5                   10

<210> SEQ ID NO 144
<211> LENGTH: 18
<212> TYPE: PRT
<213> ORGANISM: Artificial Sequence
<220> FEATURE:
<223> OTHER INFORMATION: CDR

<400> SEQUENCE: 144

Tyr Ala Arg Thr Gly Tyr Gly Ser Ser Trp Pro Met Gly His Glu Tyr
1               5                   10                  15

Asp Tyr

<210> SEQ ID NO 145
<211> LENGTH: 10
<212> TYPE: PRT
<213> ORGANISM: Artificial Sequence
<220> FEATURE:
<223> OTHER INFORMATION: CDR

<400> SEQUENCE: 145

His Ala Ala Thr Asp Thr Gly Val Ile Tyr
1               5                   10

<210> SEQ ID NO 146
<211> LENGTH: 13
<212> TYPE: PRT
<213> ORGANISM: Artificial Sequence
<220> FEATURE:
<223> OTHER INFORMATION: CDR

<400> SEQUENCE: 146

Ala Ala Asp Pro Arg Arg Leu Thr Gly Leu Tyr Asp Tyr
1               5                   10

<210> SEQ ID NO 147
<211> LENGTH: 11
<212> TYPE: PRT
<213> ORGANISM: Artificial Sequence
<220> FEATURE:
<223> OTHER INFORMATION: CDR

<400> SEQUENCE: 147

Ala Ala Thr Gly Tyr Gly Ser Ser Pro Trp Tyr
1 5 10

<210> SEQ ID NO 148
<211> LENGTH: 18
<212> TYPE: PRT
<213> ORGANISM: Artificial Sequence
<220> FEATURE:
<223> OTHER INFORMATION: CDR

<400> SEQUENCE: 148

Tyr Ala Arg Thr Gly Tyr Gly Ser Gly Arg Leu Met Gly His Glu Tyr
1 5 10 15

Asp Tyr

<210> SEQ ID NO 149
<211> LENGTH: 18
<212> TYPE: PRT
<213> ORGANISM: Artificial Sequence
<220> FEATURE:
<223> OTHER INFORMATION: CDR

<400> SEQUENCE: 149

Tyr Ala Arg Thr Gly Tyr Gly Ser Gly Arg Leu Met Gly His Glu Tyr
1 5 10 15

Asp Tyr

<210> SEQ ID NO 150
<211> LENGTH: 18
<212> TYPE: PRT
<213> ORGANISM: Artificial Sequence
<220> FEATURE:
<223> OTHER INFORMATION: CDR

<400> SEQUENCE: 150

Tyr Ala Arg Thr Gly Tyr Gly Ser Ser Trp Leu Met Gly His Glu Tyr
1 5 10 15

Asp Tyr

<210> SEQ ID NO 151
<211> LENGTH: 18
<212> TYPE: PRT
<213> ORGANISM: Artificial Sequence
<220> FEATURE:
<223> OTHER INFORMATION: CDR

<400> SEQUENCE: 151

Tyr Ala Arg Thr Gly Tyr Gly Ser Ser Trp Leu Met Gly His Glu Tyr
1 5 10 15

Asp Tyr

<210> SEQ ID NO 152
<211> LENGTH: 18
<212> TYPE: PRT
<213> ORGANISM: Artificial Sequence
<220> FEATURE:

<223> OTHER INFORMATION: CDR

<400> SEQUENCE: 152

Tyr Ala Arg Thr Gly Tyr Gly Ser Gly Arg Leu Met Gly His Glu Tyr
1 5 10 15

Asp Tyr

<210> SEQ ID NO 153
<211> LENGTH: 18
<212> TYPE: PRT
<213> ORGANISM: Artificial Sequence
<220> FEATURE:
<223> OTHER INFORMATION: CDR

<400> SEQUENCE: 153

Tyr Ala Arg Thr Gly Tyr Gly Ser Gly Trp Leu Glu Gly His Glu Tyr
1 5 10 15

Asp Tyr

<210> SEQ ID NO 154
<211> LENGTH: 18
<212> TYPE: PRT
<213> ORGANISM: Artificial Sequence
<220> FEATURE:
<223> OTHER INFORMATION: CDR

<400> SEQUENCE: 154

Tyr Ala Arg Thr Gly Tyr Gly Ser Ser Trp Leu Met Gly His Glu Tyr
1 5 10 15

Asp Tyr

<210> SEQ ID NO 155
<211> LENGTH: 18
<212> TYPE: PRT
<213> ORGANISM: Artificial Sequence
<220> FEATURE:
<223> OTHER INFORMATION: CDR

<400> SEQUENCE: 155

Tyr Ala Arg Thr Gly Tyr Gly Ser Ser Trp Leu Met Gly His Glu Tyr
1 5 10 15

Asp Tyr

<210> SEQ ID NO 156
<211> LENGTH: 14
<212> TYPE: PRT
<213> ORGANISM: Artificial Sequence
<220> FEATURE:
<223> OTHER INFORMATION: CDR

<400> SEQUENCE: 156

Ala Ala Ser Lys Ser Ala Tyr Ile Phe Asp Asp Arg Asp Tyr
1 5 10

<210> SEQ ID NO 157
<211> LENGTH: 10
<212> TYPE: PRT
<213> ORGANISM: Artificial Sequence
<220> FEATURE:
<223> OTHER INFORMATION: CDR

<400> SEQUENCE: 157

His Ile Gly Pro Glu Pro Arg Tyr Gly Tyr
1 5 10

<210> SEQ ID NO 158
<211> LENGTH: 10
<212> TYPE: PRT
<213> ORGANISM: Artificial Sequence
<220> FEATURE:
<223> OTHER INFORMATION: CDR

<400> SEQUENCE: 158

His Ile Gly Pro Glu Pro Arg Tyr Gly Tyr
1 5 10

<210> SEQ ID NO 159
<211> LENGTH: 18
<212> TYPE: PRT
<213> ORGANISM: Artificial Sequence
<220> FEATURE:
<223> OTHER INFORMATION: CDR

<400> SEQUENCE: 159

Tyr Ala Arg Thr Gly Tyr Gly Ser Ser Trp Leu Met Gly His Glu Tyr
1 5 10 15

Asp Tyr

<210> SEQ ID NO 160
<211> LENGTH: 18
<212> TYPE: PRT
<213> ORGANISM: Artificial Sequence
<220> FEATURE:
<223> OTHER INFORMATION: CDR

<400> SEQUENCE: 160

Tyr Ala Arg Thr Gly Tyr Gly Ser Ser Trp Leu Met Gly His Glu Tyr
1 5 10 15

Asp Tyr

<210> SEQ ID NO 161
<211> LENGTH: 23
<212> TYPE: DNA
<213> ORGANISM: Artificial Sequence
<220> FEATURE:
<223> OTHER INFORMATION: primer

<400> SEQUENCE: 161
gtcctggctg ctcttctaca agg 23

<210> SEQ ID NO 162
<211> LENGTH: 23
<212> TYPE: DNA
<213> ORGANISM: Artificial Sequence
<220> FEATURE:
<223> OTHER INFORMATION: primer

<400> SEQUENCE: 162
ggtacgtgct gttgaactgt tcc 23

<210> SEQ ID NO 163
<211> LENGTH: 33
<212> TYPE: DNA
<213> ORGANISM: Artificial Sequence
<220> FEATURE:
<223> OTHER INFORMATION: primer

<400> SEQUENCE: 163
ctagtgcggc cgcctggaga cggtgacctg ggt 33

<210> SEQ ID NO 164
<211> LENGTH: 38
<212> TYPE: DNA
<213> ORGANISM: Artificial Sequence
<220> FEATURE:
<223> OTHER INFORMATION: primer

<400> SEQUENCE: 164
cgcggatccc aggtgcagct gcaggagtct ggrggagg 38

<210> SEQ ID NO 165
<211> LENGTH: 89
<212> TYPE: DNA
<213> ORGANISM: Artificial Sequence
<220> FEATURE:
<223> OTHER INFORMATION: primer

<400> SEQUENCE: 165
atttttactg ctgttttatt cgcagcatcc tccgcattag ctaaaagaga ggctgaagca 60
caggtgcagc tgcaggagtc tggrggagg 89

<210> SEQ ID NO 166
<211> LENGTH: 81
<212> TYPE: DNA
<213> ORGANISM: Artificial Sequence
<220> FEATURE:
<223> OTHER INFORMATION: primer

<400> SEQUENCE: 166
agttgtcagt tcctgtgccc cccctcctcc cgcgccacct ccgcccgcac ctccgccacc 60
actggagacg gtgacctggg t 81

<210> SEQ ID NO 167
<211> LENGTH: 224
<212> TYPE: PRT
<213> ORGANISM: Artificial Sequence
<220> FEATURE:
<223> OTHER INFORMATION: Fc of human IgG1

<400> SEQUENCE: 167

Thr His Thr Cys Pro Pro Cys Pro Ala Pro Glu Ala Ala Gly Gly Pro
1 5 10 15

Ser Val Phe Leu Phe Pro Pro Lys Pro Lys Asp Thr Leu Met Ile Ser
20 25 30

Arg Thr Pro Glu Val Thr Cys Val Val Val Asp Val Ser His Glu Asp
35 40 45

Pro Glu Val Lys Phe Asn Trp Tyr Val Asp Gly Val Glu Val His Asn
50 55 60

Ala Lys Thr Lys Pro Arg Glu Glu Gln Tyr Asn Ser Thr Tyr Arg Val
65 70 75 80

Val Ser Val Leu Thr Val Leu His Gln Asp Trp Leu Asn Gly Lys Glu
85 90 95

Tyr Lys Cys Lys Val Ser Asn Lys Ala Leu Pro Ala Pro Ile Glu Lys
100 105 110

Thr Ile Ser Lys Ala Lys Gly Gln Pro Arg Glu Pro Gln Val Tyr Thr
115 120 125

Leu Pro Pro Ser Arg Glu Glu Met Thr Lys Asn Gln Val Ser Leu Thr
130 135 140

Cys Leu Val Lys Gly Phe Tyr Pro Ser Asp Ile Ala Val Glu Trp Glu

```
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220


<210> SEQ ID NO 168
<211> LENGTH: 140
<212> TYPE: PRT
<213> ORGANISM: Artificial Sequence
<220> FEATURE:
<223> OTHER INFORMATION: human 4-1BB protein

<400> SEQUENCE: 168

Gln Asp Pro Cys Ser Asn Cys Pro Ala Gly Thr Phe Cys Asp Asn Asn
1               5                   10                  15

Arg Asn Gln Ile Cys Ser Pro Cys Pro Pro Asn Ser Phe Ser Ser Ala
            20                  25                  30

Gly Gly Gln Arg Thr Cys Asp Ile Cys Arg Gln Cys Lys Gly Val Phe
        35                  40                  45

Arg Thr Arg Lys Glu Cys Ser Ser Thr Ser Asn Ala Glu Cys Asp Cys
    50                  55                  60

Thr Pro Gly Phe His Cys Leu Gly Ala Gly Cys Ser Met Cys Glu Gln
65                  70                  75                  80

Asp Cys Lys Gln Gly Gln Glu Leu Thr Lys Lys Gly Cys Lys Asp Cys
                85                  90                  95

Cys Phe Gly Thr Phe Asn Asp Gln Lys Arg Gly Ile Cys Arg Pro Trp
            100                 105                 110

Thr Asn Cys Ser Leu Asp Gly Lys Ser Val Leu Val Asn Gly Thr Lys
        115                 120                 125

Glu Arg Asp Val Val Cys Gly Pro Ser Pro Leu Gly
    130                 135                 140


<210> SEQ ID NO 169
<211> LENGTH: 127
<212> TYPE: PRT
<213> ORGANISM: Artificial Sequence
<220> FEATURE:
<223> OTHER INFORMATION: amino sequence of anti 4-1BB antibody in
      crystalline complex

<400> SEQUENCE: 169

Gln Val Gln Leu Val Glu Ser Gly Gly Gly Val Val Gln Pro Gly Arg
1               5                   10                  15

Ser Leu Arg Leu Ser Cys Ala Ala Ser Gly Ser Thr Phe Ser Ile Val
            20                  25                  30

Ala Met Gly Trp Tyr Arg Gln Ala Pro Gly Lys Gln Arg Glu Leu Val
        35                  40                  45

Ala Ser Ile Ile Thr Gly Asp Gly Asp Thr Asn Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Lys Pro Glu Asp Thr Ala Val Tyr Tyr Cys
                85                  90                  95
```

```
Tyr Ala Arg Thr Gly Tyr Gly Ser Ser Trp Leu Met Gly His Glu Tyr
            100                 105                 110

Asp Tyr Trp Gly Gln Gly Thr Gln Val Thr Val Ser Ser Leu Gly
        115                 120                 125


<210> SEQ ID NO 170
<211> LENGTH: 22
<212> TYPE: PRT
<213> ORGANISM: Artificial Sequence
<220> FEATURE:
<223> OTHER INFORMATION: framwork 1

<400> SEQUENCE: 170

Glu Val Gln Leu Val Glu Ser Gly Gly Gly Leu Val Lys Pro Gly Gly
1               5                   10                  15

Ser Leu Arg Leu Ser Cys
            20


<210> SEQ ID NO 171
<211> LENGTH: 14
<212> TYPE: PRT
<213> ORGANISM: Artificial Sequence
<220> FEATURE:
<223> OTHER INFORMATION: framwork 2

<400> SEQUENCE: 171

Trp Tyr Arg Gln Ala Pro Gly Lys Gln Arg Glu Leu Val Ala
1               5                   10


<210> SEQ ID NO 172
<211> LENGTH: 14
<212> TYPE: PRT
<213> ORGANISM: Artificial Sequence
<220> FEATURE:
<223> OTHER INFORMATION: framwork 2

<400> SEQUENCE: 172

Trp Tyr Arg Gln Ala Pro Gly Lys Gly Leu Glu Leu Val Ala
1               5                   10


<210> SEQ ID NO 173
<211> LENGTH: 30
<212> TYPE: PRT
<213> ORGANISM: Artificial Sequence
<220> FEATURE:
<223> OTHER INFORMATION: framwork 3

<400> SEQUENCE: 173

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys
            20                  25                  30


<210> SEQ ID NO 174
<211> LENGTH: 11
<212> TYPE: PRT
<213> ORGANISM: Artificial Sequence
<220> FEATURE:
<223> OTHER INFORMATION: framwork 4

<400> SEQUENCE: 174

Trp Gly Gln Gly Thr Leu Val Thr Val Ser Ser
1               5                   10
```

ANTI-4-1BB SINGLE-DOMAIN ANTIBODIES, NANOBODIES, FUSION PROTEINS THEREOF AND METHODS OF USE THEREOF FOR TREATMENT

This application is a National Stage Application under 35 U.S.C. § 371 PCT/CN2021/118955 filed on Sep. 17, 2021, which claims priority benefit from Chinese Patent Application No. 202010981835.5, filed on Sep. 17, 2020, and Chinese Patent Application No. 202011025265.9, filed on Sep. 25, 2020, the entire content of each of which is incorporated herein by reference.

The instant application contains a Sequence Listing TXT which has been submitted electronically and is hereby incorporated by reference in its entirety. Said TXT copy, created on Mar. 16, 2023, is named SequenceListing1412709_577047 and is 80,813 bytes in size.

TECHNICAL FIELD the present invention belongs to the field of biomedicine, and relates to a single-domain antibody targeting 4-1BB, fusion protein thereof, pharmaceutical composition and use thereof.

BACKGROUND ART

Tumor necrosis factor receptor superfamily member 4-1BB, also known as CD137 or TNFRF9, is a member of the TNF receptor family. 4-1BB is a type I transmembrane protein with 255 amino acids (NCBI: NP 001552), which consists of an N-terminal signal peptide containing 17 amino acids, an extracellular region of 169 amino acids, a transmembrane region of 27 amino acids, and a C-terminal intracellular region of 42 amino acids. 4-1BB is mainly expressed in activated T cells, NK cells, regulatory T cells, dendritic cells, monocytes, neutrophils and eosinophils, and endothelial cells of tumor vessels have also been reported to express 4-1BB.

During the activation process of T cells, 4-1BB molecule can provide costimulatory signals for them. When the T cell receptor contacts the antigen, it will increase the expression of 4-1BB, and the binding of 4-1BB to the ligand will cause the activation of the NF-κB signaling pathway, resulting in the activation and proliferation of T cells, and 4-1BB can also inhibit the apoptosis of activated cells. Animal models and in vitro experiments have confirmed that anti-4-1BB monoclonal antibody has anti-tumor activity. It can selectively induce the proliferation of CD8+ T cells, upregulate the expression of pro-inflammatory cytokine such as IFN-γ, and enhance the killing effect of antigen-specific effector T cells, thereby promoting tumor clearance. Anti-4-1BB monoclonal antibody can also cause the expansion of NK cells, and can increase the cytotoxic activity of CD8+ T cells through it. Anti-4-1BB antibody can also induce endothelial cells of blood vessels of tumor cells to up-regulate the expression of adhesion molecules, and promote the infiltration of activated T lymphocytes into tumor tissues. In addition, anti-4-1BB antagonist antibody can also alleviate autoimmune diseases such as autoimmune encephalomyelitis, lupus-like syndrome and collagen-induced arthritis in animal models.

Therefore, in the treatment of tumors and some autoimmune diseases, 4-1BB is an important potential target. Specifically, in preclinical animal models such as colorectal cancer, lung cancer, breast cancer, and melanoma, agonist molecules targeting 4-1BB have shown significant anti-tumor activity as single drug or in combination with anti-PD-1, anti-PD-L1, anti-CTLA-4, anti-HER-2 and other antibodies (Etxeberria I, et al. ESMO Open 2020; 4:e000733). At present, two 4-1BB antibodies are in clinical trials: Urelumab (BMS-663513, developed by Bristol-Myers Squibb) and Utomilumab (PF-05082566, developed by Pfizer). Studies have shown that Urelumab is a potent super agonist, but it also has adverse sides such as liver toxicity and fatigue; while Utomilumab has advantages in safety, but compared with Urelumab, it has limited agonist activity.

Therefore, there is an urgent need in the field to develop a more efficient antibody targeting 4-1BB and related drug thereof.

CONTENTS OF THE PRESENT INVENTION

The present inventors have developed an anti-human 4-1BB nanobody through intensive research and creative work. Specifically, the inventors used a human-derived 4-1BB antigen protein to immunize Llama to obtain a high-quality immune nanobody gene library. Among them, the inventors screened in the immune nanobody gene library to obtain two strains of anti-4-1BB nanobodies that can simultaneously bind to human and cynomolgus monkey 4-1BB, and require external cross-linking to exert activation. Then the two nanobodies are subjected to sequence optimization, the genetically engineered mutants are expressed and purified, and further screening is performed in the aspects of antibody affinity, cross-binding with cynomolgus monkey 4-1BB, and ability of activating T cells, thus a kind of nanobody strain that can be highly expressed in vitro and has high specificity is obtained. Experimental results show that the anti-4-1BB nanobody and fusion protein of the present invention have small molecular weight, can cross with cynomolgus monkey 4-1BB, do not block the natural interaction of 4-1BB ligand and 4-1BB, have strong T cell activation, and good safety. Accordingly, the following invention is provided.

One aspect of the present invention relates to an anti-4-1BB single-domain antibody, which comprises a heavy chain variable region, the heavy chain variable region comprises CDR1 to CDR3, wherein CDR1 has an amino acid sequence selected from SEQ ID NOs: 41-80, CDR2 has an amino acid sequence selected from SEQ ID NOs: 81-120, and CDR3 has an amino acid sequence of selected from SEQ ID NOs: 121-160.

One aspect of the present invention relates to an anti-4-1BB single-domain antibody, which comprises a heavy chain variable region, and the heavy chain variable region comprises CDR1 to CDR3 respectively having one of any amino acid sequences as shown in the following items 1-40:

| Item No. | CDR1's SEQ ID NO: | CDR2's SEQ ID NO: | CDR3's SEQ ID NO: |
|---|---|---|---|
| 1 | 41 | 81 | 121 |
| 2 | 42 | 82 | 122 |
| 3 | 43 | 83 | 123 |
| 4 | 44 | 84 | 124 |
| 5 | 45 | 85 | 125 |
| 6 | 46 | 86 | 126 |
| 7 | 47 | 87 | 127 |
| 8 | 48 | 88 | 128 |
| 9 | 49 | 89 | 129 |
| 10 | 50 | 90 | 130 |
| 11 | 51 | 91 | 131 |
| 12 | 52 | 92 | 132 |
| 13 | 53 | 93 | 133 |

-continued

| Item No. | CDR1's SEQ ID NO: | CDR2's SEQ ID NO: | CDR3's SEQ ID NO: |
|---|---|---|---|
| 14 | 54 | 94 | 134 |
| 15 | 55 | 95 | 135 |
| 16 | 56 | 96 | 136 |
| 17 | 57 | 97 | 137 |
| 18 | 58 | 98 | 138 |
| 19 | 59 | 99 | 139 |
| 20 | 60 | 100 | 140 |
| 21 | 61 | 101 | 141 |
| 22 | 62 | 102 | 142 |
| 23 | 63 | 103 | 143 |
| 24 | 64 | 104 | 144 |
| 25 | 65 | 105 | 145 |
| 26 | 66 | 106 | 146 |
| 27 | 67 | 107 | 147 |
| 28 | 68 | 108 | 148 |
| 29 | 69 | 109 | 149 |
| 30 | 70 | 110 | 150 |
| 31 | 71 | 111 | 151 |
| 32 | 72 | 112 | 152 |
| 33 | 73 | 113 | 153 |
| 34 | 74 | 114 | 154 |
| 35 | 75 | 115 | 155 |
| 36 | 76 | 116 | 156 |
| 37 | 77 | 117 | 157 |
| 38 | 78 | 118 | 158 |
| 39 | 79 | 119 | 159 |
| 40 | 80 | 120 | 160 |

In the present invention, the CDRs of the anti-4-1BB single-domain antibody are defined by the IMGT numbering system, please refer to Ehrenmann F, Kaas Q, Lefranc M P. IMGT/3Dstructure-DB and IMGT/DomainGapAlign: a database and a tool for immunoglobulins or antibodies, T cell receptors, MHC, IgSF and MhcSF[J]. Nucleic acids research, 2009; 38 (suppl_1):D301-D307.

In the present invention, the 4-1BB refers to human 4-1BB unless otherwise specified. In some embodiments of the present invention, the 4-1BB has an amino acid sequence as set forth in SEQ ID NO: 168.

In some embodiments of the present invention, in the anti-4-1BB single-domain antibody, any one, two, three or all four of the four framework regions thereof are humanized;

preferably, the second framework region is humanized; optionally, the first, third or fourth framework region is also modified;

preferably, the anti-4-1BB single-domain antibody has an identity of greater than or equal to 75%, greater than or equal to 76%, greater than or equal to 77%, greater than or equal to 78%, greater than or equal to 79%, or greater than or equal to 80% to that of human;

preferably, in the anti-4-1BB single-domain antibody, the framework region 1 has an amino acid sequence as set forth in SEQ ID NO: 170, the framework region 2 has an amino acid sequence as set forth in SEQ ID NO: 171 or SEQ ID NO: 172, the framework region 3 has an amino acid sequence as set forth in SEQ ID NO: 173, and the framework region 4 has an amino acid sequence as set forth in SEQ ID NO: 174.

In some embodiments of the present invention, the anti-4-1BB single-domain antibody has a $K_D$ with 4-1BB that is less than E-07, less than 5E-08, less than 4E-08, less than 3E-08, or less than 2E-08; preferably, the $K_D$ is measured by ForteBio.

In some embodiments of the present invention, the anti-4-1BB single-domain antibody has a different binding site to the 4-1BB antigen in comparison with Urelumbab and Utomilumab.

In some embodiments of the present invention, the anti-4-1BB single-domain antibody specifically binds to human 4-1BB and cross-binds to cynomolgus monkey 4-1BB.

In some embodiments of the present invention, the anti-4-1BB single-domain antibody does not block the binding of 4-1BB ligand to 4-1BB in a natural state (e.g., in a mammal, especially in a human body).

In some embodiments of the present invention, the anti-4-1BB single-domain antibody has an amino acid sequence as set forth in any one of SEQ ID NOs: 1-40.

Another aspect of the present invention relates to a fusion protein, which comprises the anti-4-1BB single-domain antibody described in any one of the items of the present invention, and an Fc fragment of human IgG or a constant region of human IgG.

In some embodiments of the present invention, the fusion protein consists of the anti-4-1BB single-domain antibody described in any one of the items of the present invention, and an Fc fragment of human IgG or a constant region of human IgG.

In some embodiments of the present invention, the fusion protein consists of the anti-4-1BB single-domain antibody described in any one of the items of the present invention, a linker, and an Fc fragment of human IgG or a constant region of human IgG.

In some embodiments of the present invention, in the fusion protein, according to the EU numbering system, the Fc fragment of human IgG or the heavy chain constant region of human IgG comprises a L234A mutation and a L235A mutation; or, the Fc fragment of IgG further comprises a G237A mutation.

In some embodiments of the present invention, the fusion protein is an anti-4-1BB heavy chain antibody. The heavy chain antibody refers to an antibody without a light chain, and is currently a common name for VHH-Fc antibody.

In some embodiments of the present invention, in the fusion protein, the Fc fragment of human IgG is an Fc fragment of human IgG1;

the heavy chain constant region of human IgG is a heavy chain constant region of human IgG1.

In some embodiments of the present invention, in the fusion protein, the Fc fragment of human IgG is an Fc fragment of human IgG1 comprising a L234A mutation and a L235A mutation; optionally, the Fc fragment of human IgG1 further comprises a G237A mutation;

preferably, the Fc fragment of human IgG1 has an amino acid sequence as set forth in SEQ ID NO: 167.

In some embodiments of the present invention, in the fusion protein, the Fc fragment of human IgG or the constant region of human IgG is ligated directly or through a linker to the C-terminus of the anti-4-1BB single-domain antibody.

In some embodiments of the present invention, in the fusion protein, the Fc fragment of human IgG1 or the constant region of human IgG1 is ligated directly or through a linker to the C-terminus of the anti-4-1BB single-domain antibody.

Another aspect of the present invention relates to an isolated nucleic acid molecule, which encodes the anti-4-1BB single-domain antibody according to any one of the items of the present invention or the fusion protein according to any one of the items of the present invention.

The present invention also relates to a vector, which comprises the isolated nucleic acid molecule of the present invention.

The present invention also relates to a host cell, which comprises the isolated nucleic acid molecule of the present invention, or the vector of the present invention.

Another aspect of the present invention relates to a method for preparing the anti-4-1BB single-domain antibody described in any one of the items of the present invention or the fusion protein described in any one of the items of the present invention, which comprises steps of culturing the host cell of the present invention under suitable conditions, and recovering the anti-4-1BB single-domain antibody or fusion protein from a cell culture.

Another aspect of the present invention relates to a conjugate, which comprises an antibody moiety and a coupling moiety, wherein the antibody moiety is the anti-4-1BB single-domain antibody described in any one of the items of the present invention or the fusion protein described in any one of the items of the present invention, the coupling moiety is a detectable label; preferably, the coupling moiety is a radioactive isotope, a fluorescent substance, a luminescent substance, a colored substance or an enzyme.

Another aspect of the present invention relates to a kit, which comprises the anti-4-1BB single-domain antibody described in any one of the items of the present invention or the fusion protein described in any one of the items of the present invention, or comprises the conjugate of the present invention;

preferably, the kit further comprises a second antibody capable of specifically binding to the single-domain antibody or fusion protein; optionally, the second antibody further comprises a detectable label, such as a radioactive isotope, a fluorescent substance, a luminescent substance, a colored substance or an enzyme.

Another aspect of the present invention relates to a use of the anti-4-1BB single-domain antibody according to any one of the items of the present invention or the fusion protein according to any one of the items of the present invention in the manufacture of a kit for detecting the presence or level of 4-1BB in a sample.

Another aspect of the present invention relates to a pharmaceutical composition, which comprises the anti-4-1BB single-domain antibody described in any one of the items of the present invention or the fusion protein described in any one of the items of the present invention or comprises the conjugate of the present invention; optionally, the pharmaceutical composition also comprises a pharmaceutically acceptable excipient.

Another aspect of the present invention relates to a use of the anti-4-1BB single-domain antibody described in any one of the items of the present invention or the fusion protein described in any one of the items of the present invention or the conjugate of the present invention in the manufacture of a medicament for the prevention and/or treatment of a malignant tumor or an autoimmune disease;

preferably, the malignant tumor is selected from a group consisting of rectal cancer, colon cancer, lung cancer, breast cancer, melanoma, liver cancer, gastric cancer, renal cell carcinoma, ovarian cancer, esophageal cancer and head and neck cancer;

preferably, the autoimmune disease is selected from a group consisting of autoimmune encephalomyelitis, lupus-like syndrome and collagen-induced arthritis.

Another aspect of the present invention relates to a method for treating and/or preventing a malignant tumor or autoimmune disease, comprising a step of administering an effective amount of the anti-4-1BB single-domain antibody described in any one of the items of the present invention or the fusion protein described in any one of the items of the present invention or the conjugate of the present invention to a subject in need thereof;

preferably, the malignant tumor is selected from a group consisting of rectal cancer, colon cancer, lung cancer, breast cancer, melanoma, liver cancer, gastric cancer, renal cell carcinoma, ovarian cancer, esophageal cancer and head and neck cancer;

preferably, the autoimmune disease is selected from a group consisting of autoimmune encephalomyelitis, lupus-like syndrome and collagen-induced arthritis.

In some embodiments of the present invention, in the method, the step of administering an effective amount of the single-domain antibody or fusion protein according to any one of the items of the present invention to the subject in need thereof is performed before or after surgical treatment, and/or before or after radiation therapy.

In some embodiments of the present invention, in the method,

- the single-domain antibody or fusion protein of the present invention has a single dose of 0.1-100 mg, preferably 4.8-24 mg or 1-10 mg, per kilogram of body weight; or, the single-domain antibody or fusion protein of the present invention has a single dose of 10-1000 mg, preferably 50-500 mg, 100-400 mg, 150-300 mg, 150-250 mg or 200 mg, per subject;
- preferably, the administration is performed once every 3 days, 4 days, 5 days, 6 days, 10 days, 1 week, 2 weeks or 3 weeks;
- preferably, the administration is performed in a manner of intravenous drip or intravenous injection.

The anti-4-1BB single-domain antibody according to any one of the items of the present invention or the fusion protein according to any one of the items of the present invention or the conjugate of the present invention, which is used for treating and/or preventing a malignant tumor or autoimmunity disease;

- preferably, the malignant tumor is selected from a group consisting of rectal cancer, colon cancer, lung cancer, breast cancer, melanoma, liver cancer, gastric cancer, renal cell carcinoma, ovarian cancer, esophageal cancer and head and neck cancer;
- preferably, the autoimmune disease is selected from a group consisting of autoimmune encephalomyelitis, lupus-like syndrome and collagen-induced arthritis.

As used herein, the term "antibody" refers to an immunoglobulin molecule generally composed of two pairs of polypeptide chains, each pair having one "light" (L) chain and one "heavy" (H) chain. Antibody light chains can be classified as κ and λ light chains. Heavy chains can be classified as μ, δ, γ, α, or ε, and the isotypes of antibody are defined as IgM, IgD, IgG, IgA, and IgE, respectively. Within the light chain and heavy chain, variable and constant regions are linked by a "J" region of about 12 or more amino acids, and the heavy chain further comprising a "D" region of about 3 or more amino acids. Each heavy chain is composed of a heavy chain variable region (VH) and a heavy chain constant region (CH). The heavy chain constant region consists of 3 domains (CH1, CH2 and CH3). Each light chain is composed of a light chain variable region (VL) and a light chain constant region (CL). The light chain constant region consists of one domain, CL. The antibody constant regions mediate the binding of immunoglobulin to a host tissue or factor, including various cells (e.g., effector cells) of the immune system and first component (Clq) of the classical complement system. VH and VL regions can also be subdivided into regions with high variability (which are called as complementarity determining regions (CDRs)), among which more conserved regions called framework regions (FRs) are interspersed. Each VH and VL consists of 3 CDRs and 4 FRs arranged in the following order: FR1, CDR1, FR2, CDR2, FR3, CDR3, and FR4, from amino-terminal to carboxy-terminal. The variable regions (VH and VL) of each heavy chain/light chain pair form an antibody binding site, respectively. Assignment of amino acids to the regions or domains follows the definition of Bethesda M.d., Kabat Sequences of Proteins of Immunological Interest (National Institutes of Health, (1987 and 1991)), or Chothia & Lesk J. Mol. Biol. 1987; 196:901-917; Chothia et al. Nature 1989; 342:878-883, or the IMGT numbering system, see the definitions of Ehrenmann F, Kaas Q, Lefranc M P. IMGT/3Dstructure-DB and IMGT/DomainGapAlign: a database and a tool for immunoglobulins or antibodies, T cell receptors, MHC, IgSF and MhcSF[J]. Nucleic acids research, 2009; 38 (suppl_1):D301-D307.

The term "antibody" is not limited to any particular antibody production method. For example, it includes recombinant antibody, monoclonal antibody and polyclonal antibody. The antibody can be an antibody of different isotype, for example, IgG (e.g., IgG1, IgG2, IgG3, or IgG4 subtype), IgA1, IgA2, IgD, IgE, or IgM antibody.

As used herein, the terms "mAb" and "monoclonal antibody" refer to an antibody or a fragment of antibody derived from a group of highly homologous antibody molecules, that is, except for natural mutations that may occur spontaneously, a group of identical antibody molecules. The mAb is highly specific for a single epitope on an antigen. Compared with monoclonal antibody, a polyclonal antibody usually contains at least two or more different antibodies, and these different antibodies usually recognize different epitopes on an antigen. Monoclonal antibodies can usually be obtained using hybridoma technology that was first reported by Kohler et al. (Köhler G, Milstein C. Continuous cultures of fused cells secreting antibody of predefined specificity [J]. nature, 1975; 256(5517):495), and can also be obtained using recombinant DNA techniques (see, for example, U.S. Pat. No. 4,816,567).

As used herein, the term "humanized antibody" refers to an antibody or an antibody fragment obtained by replacing all or part of the CDR regions of a human immunoglobulin (recipient antibody) with the CDR regions of a non-human antibody (donor antibody), wherein the donor antibody can be a non-human (e.g., mouse, rat, or rabbit) antibody with the desired specificity, affinity, or reactivity. In addition, some amino acid residues in the framework region (FR) of the recipient antibody can also be replaced by the corresponding amino acid residues of a non-human antibody, or by the amino acid residues of other antibodies, so as to further improve or optimize the performance of antibody. For more details on humanized antibodies, see, for example, Jones et al., Nature 1986; 321:522 525; Reichmann et al., Nature, 1988; 332:323329; Presta, Curr. Op. Struct. Biol. 1992; 2:593-596; and Clark, Immunol. Today 2000; 21: 397-402. In some cases, the antigen-binding fragment of antibody is a diabody, in which the $V_H$ and $V_L$ domains are expressed on a single polypeptide chain, but the linker used is too short to allow the pairing between two domains of the same chain, thereby forcing the domain to pair with a complementary domain of another chain and creating two antigen-binding sites (see, for example, Holliger P. et al., Proc. Natl. Acad. Sci. USA 1993; 90:6444 6448 and Poljak R. J. et al., Structure 1994; 2:1121 1123).

The fusion protein as described herein is a protein product co-expressed by two genes through DNA recombination. Methods for producing and purifying antibodies and antigen-binding fragments are well known in the art (e.g., Cold Spring Harbor's Antibody Laboratory Technique Guide, Chapters 5-8 and Chapter 15).

As used herein, the term "isolation" or "isolated" means acquisition from a natural state by an artificial means. If an "isolated" substance or component occurs in nature, the natural environment in which it exists has been altered, or the substance has been isolated from the natural environment, or both have occurred. For example, for an unisolated polynucleotide or polypeptide naturally existing in a living animal, the same polynucleotide or polypeptide with high purity isolated from this natural state is called isolated. The term "isolation" or "isolated" does not exclude the admixture of an artificial or synthetic substance, nor the presence of other impurities which do not affect the substance activity.

As used herein, the term "vector" refers to a nucleic acid delivery vehicle into which a polynucleotide can be inserted. When the vector is capable of achieving the expression of a protein encoded by the inserted polynucleotide, the vector is called an expression vector. A vector can be introduced into a host cell by transformation, transduction or transfection, so that a genetic material element it carries can be expressed in the host cell. Vectors are well known to those skilled in the art, including but not limited to: plasmid; phagemid; cosmid; artificial chromosome, such as yeast artificial chromosome (YAC), bacterial artificial chromosome (BAC) or P1-derived artificial chromosome (PAC); phage such as λ phage or M13 phage, and animal viruses. The animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including but not limited to, promoter sequence, transcription initiation sequence, enhancer sequence, selection element, and reporter gene. In addition, the vector may also contain a replication origin.

As used herein, the term "host cell" refers to a cell that can be used to introduce a vector, including but not limited to, prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, GS cell, COS cell, NSO cell, HeLa cell, BHK cell, HEK293 cell or human cell.

As used herein, the term "pharmaceutically acceptable excipient" refers to a carrier and/or excipient that is pharmacologically and/or physiologically compatible with the subject and the active ingredient, which are well known in the art (see, for example, Remington's Pharmaceutical Sciences. Edited by Gennaro A R, 19th ed. Pennsylvania: Mack Publishing Company, 1995), and include but are not limited to: pH adjuster, surfactant, adjuvant, ionic strength enhancer. For example, the pH regulator includes but is not limited to phosphate buffer; the surfactant includes but is not limited to cationic, anionic or nonionic surfactant, such as Tween-80; the ionic strength enhancer includes but is not limited to sodium chloride.

As used herein, the term "effective amount" refers to an amount sufficient to achieve, or at least partially achieve, the desired effect. For example, an effective amount for preventing a disease (e.g., a tumor) refers to an amount sufficient to prevent, arrest, or delay the occurrence of a disease (e.g., a tumor); an effective amount for treating a disease refers to an amount sufficient to cure or at least partially prevent a disease and complication thereof in a patient with the disease. Determining such an effective amount is well within the capability of those skilled in the art. For example, an effective amount for therapeutic use will depend on the severity of the disease to be treated, the general state of the patient's own immune system, the general condition of the patient such as age, weight and sex, the mode of administration of drug, other therapies administered concomitantly, and so on.

The present invention also relates to any one of the following items 1 to 11:

1. An anti-4-1BB nanobody, characterized in that, the anti-4-1BB nanobody has a VHH chain with an amino acid sequence as set forth in any one of SEQ ID NOs: 1-40;

or, with an amino acid sequence which is a derived sequence of anyone of the above amino acid sequence and is subjected to an addition, deletion, modification and/or substitution of 1-8 (preferably 1-5, more preferably 1-3) amino acid residues, and is capable of retaining the 4-1BB binding affinity of the 4-1BB nanobody.

2. A fusion protein, characterized in that, the fusion protein has a structure shown in Formula I from the N-terminal to the C-terminal:

Z1-L-Z2 (Formula I)

in the Formula,

Z1 represents one or more (preferably 1-2, more preferably 1) of the VHH chain of the anti-4-1BB nanobody as described in item 1;

Z2 represents an Fc fragment of immunoglobulin;

L represents an optional linker sequence.

3. A polynucleotide, characterized in that, the polynucleotide encodes the anti-4-1BB nanobody as described in item 1 or the fusion protein as described in item 2.

4. An expression vector, characterized in that, the expression vector comprises the polynucleotide as described in item 3.

5. A host cell, characterized in that, the host cell comprises the expression vector as described in item 4, or the polynucleotide as described in item 3 is integrated into its genome.

6. A method for producing an anti-4-1BB nanobody or fusion protein, characterized by, comprising steps:

(a) cultivating the host cell as described in item 5 under conditions suitable for the production of the anti-4-1BB nanobody or fusion protein, thereby obtaining a culture containing the anti-4-1BB nanobody or fusion protein; and (b) isolating or recovering the anti-4-1BB nanobody or fusion protein from the culture.

7. An immunoconjugate, characterized in that, the immunoconjugate comprises:

(a) the anti-4-1BB nanobody as described in item 1, or the fusion protein as described in item 2; and (b) a coupling moiety selected from a group consisting of detectable label, drug, toxin, cytokine, radionuclide, or enzyme.

8. Use of the anti-4-1BB nanobody as described in item 1 or the fusion protein as described in item 2, in the manufacture of (a) a reagent for detecting 4-1BB molecule; or (b) a medicament for treating a tumor.

9. A pharmaceutical composition, characterized by, comprising:

(i) the anti-4-1BB nanobody as described in item 1, the fusion protein as described in item 2, or the immunoconjugate as described in item 7; and (ii) a pharmaceutically acceptable carrier.

10. A recombinant protein, characterized in that, the recombinant protein comprises:

(i) a sequence of the anti-4-1BB nanobody as described in item 1, or the fusion protein as described in item 2; and (ii) optionally a tag sequence to help expression and/or purification.

11. A protein complex, characterized in that, the complex is formed with 4-1BB protein and anti-4-1BB antibody or antigen-binding fragment thereof through hydrogen bonding and/or hydrophobic interaction;

wherein, the hydrogen bonding comprises more than 4 (preferably more than 5, more preferably more than 6, and most preferably 7) acting sites selected from the following group: Asp at position 118, Leu at position 123, Arg at position 130, Val at position 132, Cys at position 134, Gly at position 135, and Ser at position 137 in the 4-1BB protein;

moreover, the hydrophobic interaction has an action interface constituted with more than 2 (preferably more than 3, more preferably more than 4) sites selected from the following group: Leu at position 123, Val at position 124, Val at position 133, and Pro at position 136 in the 4-1BB protein;

wherein, the amino acid numbering of the 4-1BB protein is based on the numbering of SEQ ID NO: 168.

The present invention also relates to any one of the following first to fifteenth aspects:

In a first aspect of the present invention, there is provided an anti-4-1BB nanobody, the anti-4-1BB nanobody has a VHH chain with an amino acid sequence as set forth in any one of SEQ ID NO: 1-40;

wherein, any amino acid sequence in the above amino acid sequences further comprises a derived sequence that is optionally subjected to an addition, deletion, modification and/or substitution of 1-8 (preferably 1-5, more preferably 1-3) amino acid residues, and is capable of retaining the 4-1BB binding affinity of the 4-1BB nanobody.

In another preferred embodiment, the anti-4-1BB nanobody has a VHH chain with an amino acid sequence as set forth in any one of SEQ ID NO: 3, 35, 37, 38, 39 or 40.

In a second aspect of the present invention, a fusion protein is provided, the fusion protein has a structure as shown in Formula I from the N-terminal to the C-terminal:

Z1-L-Z2 (Formula I)

in the formula,

Z1 represents one or more (preferably 1-2, more preferably 1) VHH chains of the anti-4-1BB nanobody according to the first aspect of the present invention;

Z2 represents an Fc fragment of immunoglobulin;

L represents an optional linker sequence.

In another preferred embodiment, the fusion protein is a dimer, and the dimer is formed by a disulfide bond between Fc fragments in Z2.

In another preferred embodiment, the immunoglobulin is IgG1, IgG2, IgG3 or IgG4; preferably IgG1, IgG2 or IgG4.

In another preferred embodiment, the immunoglobulin is IgG1, or a mutant thereof.

In another preferred embodiment, the L has an amino acid sequence selected from a group consisting of GGGGS, $(GGGGS)_2$, $(GGGGS)_3$, $(GGGGS)_4$, $(GGGGS)_5$, or combination thereof.

In another preferred embodiment, the Z2 has an amino acid sequence as set forth in SEQ ID NO: 167.

In another preferred embodiment, the Z2 has an amino acid sequence identical or substantially identical to the amino acid sequence set forth in SEQ ID NO: 167.

In another preferred embodiment, the term "substantially identical" means that at most 50 (preferably 1-20, more preferably 1-10, more preferably 1-5, most preferably 1-3) amino acids are different, wherein the difference comprises substitution, deletion or addition of amino acids.

In another preferred embodiment, the term "substantially identical" means that the amino acid sequence has a sequence identity of at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the corresponding amino acid sequence.

In another preferred embodiment, in the Formula I of the fusion protein, the Z1 has an amino acid sequence as set forth in any of SEQ ID NO: 1-40, and L is none, and the Z2 has an amino acid sequence as set forth in SEQ ID NO: 167;

wherein, any amino acid sequence in the above amino acid sequences further comprises a derived sequence that is optionally subjected an addition, deletion, modification and/or substitution of 1-8 (preferably 1-5, more preferably 1-3) amino acid residues, and is capable of retaining the 4-1BB binding affinity.

In another preferred embodiment, in the Formula I of the fusion protein, the Z1 has an amino acid sequence as set forth in any of SEQ ID NO: 3, 35, 37, 38, 39 or 40, and L is none, and the Z2 has an amino acid sequence as set forth in SEQ ID NO: 167;

wherein, any amino acid sequence in the above amino acid sequences further comprises a derived sequence that is optionally subjected to an addition, deletion, modification and/or substitution of also includes 1-8 (preferably 1-5, more preferably 1-3) amino acid residues, and is capable of retaining the 4-1BB binding affinity.

In another preferred embodiment, the fusion protein has an amino acid sequence comprising from the N-terminal to the C-terminal: the sequence as set forth in any one of SEQ ID NO: 1-40 and the sequence as set forth in SEQ ID NO: 167.

In another preferred embodiment, the fusion protein has an amino acid sequence comprising from the N-terminal to the C-terminal: the sequence as set forth in any one of SEQ ID NO: 3, 35, 37, 38, 39 or 40, and the sequence as set forth in SEQ ID NO: 167.

In the third aspect of the present invention, there is provided a polynucleotide, the polynucleotide encodes the anti-4-1BB nanobody according to the first aspect of the present invention or the fusion protein according to the second aspect of the present invention.

In another preferred embodiment, the polynucleotide comprises DNA or RNA.

In the fourth aspect of the present invention, there is provided an expression vector, the vector comprises the polynucleotide according to the third aspect of the present invention.

In the fifth aspect of the present invention, there is provided a host cell, the host cell comprises the expression vector according to the fourth aspect of the present invention, or the polynucleotide according to the third aspect of the present invention is integrated into its genome.

In another preferred embodiment, the host cell comprises prokaryotic cell or eukaryotic cell.

In another preferred embodiment, the host cell is selected from a group consisting of *Escherichia coli*, yeast cell, and mammalian cell.

In a sixth aspect of the present invention, there is provided a method for producing an anti-4-1BB nanobody or fusion protein, comprising steps of:

(a) culturing the host cell according to the fifth aspect of the present invention under conditions suitable for producing the anti-4-1BB nanobody or fusion protein, thereby obtaining a culture containing the anti-4-1BB nanobody or fusion protein; and (b) isolating or recovering the anti-4-1BB nanobody or fusion protein from the culture.

In the seventh aspect of the present invention, there is provided an immunoconjugate, the immunoconjugate comprises:

(a) the anti-4-1BB nanobody according to the first aspect of the present invention, or the fusion protein according to the second aspect of the present invention; and (b) a coupling moiety selected from a group consisting of detectable label, drug, toxin, cytokine, radionuclide, or enzyme.

In another preferred embodiment, the coupling moiety is a drug or a toxin.

In another preferred embodiment, the coupling moiety is a detectable label.

In another preferred embodiment, the coupling moiety is selected from: fluorescent or luminescent label, radioactive label, MRI (magnetic resonance imaging) or CT (computer X-ray tomography) contrast agent, or enzyme capable of producing detectable product, radionuclide, biotoxin, cytokine (e.g., IL-2, etc.), antibody, antibody Fc fragment, antibody scFv fragment, gold nanoparticle/nanorod, virus particle, liposome, nanomagnetic particle, drug precursor activating enzyme (e.g., DT-diaphorase (DTD) or biphenylhydrolase-like protein (BPHL)), chemotherapeutic agent (e.g., cisplatin), or nanoparticle in any form, etc.

In another preferred embodiment, the immunoconjugate comprises: a multivalent (e.g., bivalent) form of the anti-4-1BB nanobody as described in the first aspect of the present invention, or the fusion as described in the second aspect of the present invention protein.

In another preferred embodiment, the term "multivalent" means that the immunoconjugate has an amino acid sequence comprising multiple repeats of the anti-4-1BB nanobody as described in the first aspect of the present invention, or the fusion protein described in the second aspect.

In the eighth aspect of the present invention, there is provided a use of the anti-4-1BB nanobody as described in the first aspect of the present invention or the fusion protein as described in the second aspect of the present invention, in the manufacture of (a) a reagent for the detection of 4-1BB molecule; or (b) a medicament for the treatment of a tumor.

In another preferred embodiment, the detection comprises flow detection and cell immunofluorescence detection.

In the ninth aspect of the present invention, there is provided a pharmaceutical composition, comprising:

(i) the anti-4-1BB nanobody as described in the first aspect of the present invention, the fusion protein as described in the second aspect of the present invention, or the immunoconjugate as described in the seventh aspect of the present invention; and (ii) a pharmaceutically acceptable carrier.

In another preferred embodiment, the pharmaceutical composition is in the form of injection.

In another preferred embodiment, the pharmaceutical composition is used to prepare a drug for treating a tumor, and the tumor is selected from a group consisting of gastric cancer, liver cancer, leukemia, kidney tumor, lung cancer, small intestine cancer, bone cancer, prostate cancer, colorectal cancer, breast cancer, colon cancer, cervical cancer, lymphoma cancer, adrenal gland tumor, bladder tumor, melanoma, head and neck cancer, nasopharyngeal cancer, thyroid tumor, tongue cancer, or combination thereof.

In the tenth aspect of the present invention, there is provided one or more uses of the anti-4-1BB nanobody as described in the first aspect of the present invention or the fusion protein as described in the second aspect of the present invention:

(i) use for the detection of human 4-1BB molecule;
(ii) use for flow detection;
(iii) use for cell immunofluorescence detection;
(iv) use for the treatment of a tumor; and
(v) use for tumor diagnosis.

In another preferred embodiment, the use is non-diagnostic and non-therapeutic.

In the eleventh aspect of the present invention, there is provided a recombinant protein, and the recombinant protein comprises:

(i) a sequence of the anti-4-1BB nanobody as described in the first aspect of the present invention, or the fusion protein as described in the second aspect of the present invention; and
(ii) optionally a tag sequence to help expression and/or purification.

In another preferred embodiment, the tag sequence comprises: 6His tag, HA tag, Flag tag, Fc tag, or combination thereof.

In another preferred embodiment, the recombinant protein specifically binds to 4-1BB protein.

In the twelfth aspect of the present invention, there is provided the anti-4-1BB nanobody as described in the first aspect of the present invention, the fusion protein as described in the second aspect of the present invention, or the immunoconjugate as described in the seventh aspect of the present invention, which is used to prepare a medicament, a reagent, a detection plate or a kit;

wherein, the reagent, detection plate or kit is used for: detecting 4-1BB protein in a sample;

wherein, the medicament is used for treating or preventing various blood tumors and solid tumors.

In another preferred embodiment, the tumors comprise: gastric cancer, lymphoma, liver cancer, leukemia, kidney tumor, lung cancer, small intestine cancer, bone cancer, prostate cancer, colorectal cancer, breast cancer, colon cancer, adrenal gland tumor, melanoma, head and neck cancer, nasopharyngeal cancer, thyroid tumor, tongue cancer, or combination thereof.

In a thirteenth aspect of the present invention, there is provided a method for detecting 4-1BB protein in a sample, comprising steps of:

(1) contacting the sample with the anti-4-1BB nanobody as described in the first aspect of the present invention or the fusion protein as described in the second aspect of the present invention;
(2) detecting whether an antigen-antibody complex is formed, wherein the formation of the complex indicates the presence of 4-1BB protein in the sample.

In another preferred embodiment, the detection comprises qualitative detection and quantitative detection.

In the fourteenth aspect of the present invention, there is provided a method for treating a disease, the method comprising: administering the anti-4-1BB nanobody as described in the first aspect of the present invention, the fusion protein as described in the second aspect of the present invention, or the immunoconjugate as described in the seventh aspect of the present invention to a subject in need thereof.

In another preferred embodiment, the subject comprises a mammal.

In another preferred embodiment, the mammal is a human.

In the fifteenth aspect of the present invention, there is provided a protein complex formed with 4-1BB protein and anti-4-1BB antibody or antigen-binding fragment thereof through interaction.

In another preferred embodiment, the interaction comprises hydrogen bonding and hydrophobic interaction.

In another preferred embodiment, the anti-4-1BB antibody is an anti-4-1BB nanobody.

In another preferred embodiment, the anti-4-1BB antibody is the anti-4-1BB nanobody according to the first aspect of the present invention.

In another preferred embodiment, the complex is formed with 4-1BB protein and anti-4-1BB antibody or antigen-binding fragment thereof through hydrogen bonding and/or hydrophobic interaction;

wherein, the hydrogen bonding comprises more than 4 (preferably more than 5, more preferably more than 6, and most preferably 7) acting sites in the 4-1BB protein selected from the following group: Asp at position 118, Leu at position 123, Arg at position 130, Val at position 132, Cys at position 134, Gly at position 135, and Ser at position 137;

moreover, the hydrophobic interaction has an action interface constituted with more than 2 (preferably more than 3, more preferably more than 4) sites in the 4-1BB protein selected from the following group: Leu at position 123, Val at position 124, Val at position 133, and Pro at position 136;

wherein, the amino acid numbering of the 4-1BB protein is based on the numbering of SEQ ID NO: 168.

In another preferred embodiment, the hydrophobic interaction action interface further comprises more than 4 (preferably more than 5, more preferably more than 6, most preferably more than 7 or more than 8) sites in the anti-4-1BB antibody or antigen-binding fragment thereof that are selected from the following group: Val at 32, Ala at position 33, Tyr at position 37, Leu at position 47, Ile at position 52, Tyr at position 97, Tyr at position 102, and Trp at position 115;

wherein, the amino acid numbering of the anti-4-1BB antibody or antigen-binding fragment thereof is based on the numbering of SEQ ID NO: 169 or 39.

In another preferred embodiment, the 4-1BB protein in the complex has an amino acid sequence as set forth in SEQ ID NO: 168.

In another preferred embodiment, the anti-4-1BB nanobody in the complex has an amino acid sequence as set forth in SEQ ID NO: 169 or 39.

In another preferred embodiment, the hydrogen bonding is located at Asp at position 118, Leu at position 123, Arg at position 130, Val at position 132, Cys at position 134, Gly at position 135, and/or Ser at position 137;

wherein, the amino acid numbering is based on the numbering of SEQ ID NO: 168.

In another preferred embodiment, the hydrophobic interaction interface is located at Leu at position 123, Val at position 124, Val at position 133 and/or Pro at position 136 of the 4-1BB protein, and at Val at position 32, Ala at position 33, Tyr at position 37, Leu at position 47, Ile at position 52, Tyr at position 97, Tyr at position 102, and Trp at position 115 of the anti-4-1BB nanobody;

wherein, the amino acid numbering of the 4-1BB protein is based on the numbering of SEQ ID NO: 168, and the amino acid numbering of the VHH chain of the anti-4-1BB nanobody is based on the numbering of SEQ ID NO: 169 or 39.

Terminology

In order that the present disclosure may be more readily understood, certain terms are first defined. As used in this application, unless expressly stated otherwise herein, each of the following terms shall have the meaning given below. Other definitions are set forth throughout the present application.

As used herein, the term "about" can refer to a value or composition within an acceptable error range for a particular value or composition as determined by one of ordinary skill in the art, which will depend in part on how the value or composition is measured or determined.

As used herein, the terms "give" and "administrate" are used interchangeably and refer to that the product of the present invention is physically introduced into a subject using any of a variety of methods and delivery systems known to those skilled in the art, including intravenous, intramuscular, subcutaneous, intraperitoneal, spinal or other parenteral routes of administration, for example by injection or infusion.

Nanobody of the Present Invention

As used herein, the terms "nanobody of the present invention", "anti-4-1BB nanobody of the present invention", "4-1BB nanobody of the present invention" are used interchangeably, and all refer to a nanobody capable of specifically recognizing and binding to 4-1BB (including human 4-1BB). Particularly preferred is a nanobody having VHH chain with an amino acid sequence as set forth in any one of SEQ ID NO: 1-40, more preferably a nanobody having VHH chain with an amino acid sequence as set forth in any one of SEQ ID NO: 3, 35, 37, 38, 39 or 40.

As used herein, the terms "single-domain antibody (VHH)" and "nanobody" have the same meaning and refer to a nanobody (VHH) consisting of only one heavy chain variable region constructed by cloning an antibody heavy chain variable region, which is the smallest antigen-binding fragment with complete function. Usually, after obtaining the antibody that naturally lacks the light chain and heavy chain constant region 1 (CH1), the antibody heavy chain variable region is cloned to construct a nanobody (VHH) consisting of only one heavy chain variable region.

As used herein, the term "antibody" or "immunoglobulin" is a heterotetrameric glycoprotein of about 150,000 Daltons with identical structural feature, consisting of two identical light chains (L) and two identical heavy chains (H). Each light chain is linked to a heavy chain by one covalent disulfide bond, while the number of disulfide bonds varies between heavy chains of different immunoglobulin isotypes. Each heavy chain and light chain also has regularly spaced intrachain disulfide bonds. Each heavy chain has a variable region (VH) at one end followed by multiple constant regions. Each light chain has a variable region (VL) at one end and a constant region at the other end; the constant region of light chain is opposite to the first constant region of heavy chain, and the variable region of light chain is opposite to the variable region of heavy chain. Specific amino acid residues form the interface between the variable regions of the light and heavy chains.

As used herein, the term "variable" means that certain portions of antibody variable regions differ in sequence, which contribute to the binding and specificity of each particular antibody for its particular antigen. However, the variability is not evenly distributed throughout antibody variable domains. It is concentrated in three segments called complementarity determining regions (CDRs) or hypervariable regions in the light chain and heavy chain variable regions. The more conserved portions of the variable domains are called framework regions (FRs). The variable regions of native heavy and light chains each contain four FR regions that are in a roughly-folded configuration and connected by three CDRs that form joining loops, which in some cases may form a partially folded structure. The CDRs in each chain are brought into close proximity by the FR regions and together with the CDRs of the other chain form the antigen-binding site of the antibody (see Kabat et al., NIH Publ. No. 91-3242, Vol. I, pp. 647-669 (1991)). The constant regions are not directly involved in the binding of antibody to antigen, but they exhibit different effector functions, for example being involved in the antibody-dependent cytotoxicity of antibody.

As known to those skilled in the art, immunoconjugate and fusion expression product comprise: a conjugate by binding a drug, toxin, cytokine, radionuclide, enzyme and other diagnostic or therapeutic molecule combined to the antibody or fragment thereof of the present invention. The present invention further comprises a cell surface label or antigen capable of binding to the anti-4-1BB protein antibody or fragment thereof.

As used herein, the terms "heavy chain variable region" and "VH" are used interchangeably.

As used herein, the terms "variable region" and "complementarity determining region (CDR)" are used interchangeably.

In a preferred embodiment of the present invention, the heavy chain variable region of the antibody comprises three complementarity determining regions: CDR1, CDR2, and CDR3.

In a preferred embodiment of the present invention, the heavy chain of the antibody comprises the above-mentioned heavy chain variable region and heavy chain constant region.

In the present invention, the terms "antibody of the present invention", "protein of the present invention", or "polypeptide of the present invention" are used interchangeably, and all refer to a polypeptide that specifically binds to 4-1BB protein, for example, a protein or peptide with the heavy chain variable region, which may or may not comprise a starting methionine.

The present invention further provides an additional protein or fusion expression product that comprises the antibody of the present invention. Specifically, the present invention comprises any protein or protein conjugate and fusion expression product (i.e., immunoconjugate and fusion expression product) having a heavy chain variable region, as long as the variable region is identical or at least 90% homologous, preferably at least 95% homologous, to the heavy chain of the antibody of the present invention.

In general, the antigen-binding properties of an antibody can be described by three specific regions located in the heavy chain variable region, called the variable region (CDR), which is separated into four framework regions (FRs), the four FRs have relatively conservative amino acid sequences and do not directly participate in the binding reaction. These CDRs form a ring structure, and the 13 sheets formed by the FRs therebetween are close to each other in the spatial structure. The CDRs on the heavy chain and the corresponding CDRs on the light chain constitute the antigen-binding site of the antibody. By comparing the amino acid sequences of antibodies of the same type, the amino acids constituting the FR or CDR regions can be determined. Nanobody also has 4 framework regions (frameworks), of which the 1st, 3rd and 4th framework regions (framework region 1, framework region 3 and framework region 4) have high homology with human antibody and are less necessary to be modified during the humanization process; it is preferable to modify the 2nd framework region, namely framework region 2 (framework 2).

The variable regions of the heavy chain of the antibody of the present invention are of particular interest because at least some of them are involved in binding antigen. Therefore, the present invention comprises those molecules having antibody heavy chain variable regions with CDRs, as long as the CDRs are more than 90% (preferably more than 95%, and most preferably more than 98%) homologous to the CDRs identified herein.

The present invention comprises not only intact antibody, but also antibody fragment with immunological activity or fusion protein formed by antibody and other sequences. Accordingly, the present invention further comprises fragment, derivative and analog of the antibody.

As used herein, the terms "fragment", "derivative" and "analogue" refer to a polypeptide that substantially retains the same biological function or activity of the antibody of the present invention. The polypeptide fragment, derivative or analog of the present invention may be (i) a polypeptide having one or more substituted conservative or non-conservative amino acid residues (preferably conservative amino acid residues), and such substituted amino acid residues may or may not be encoded by genetic code, or (ii) a polypeptide having a substituent group in one or more amino acid residues, or (iii) a polypeptide formed by fusing a mature polypeptide to another compound (e.g., a compound that extends the half-life of the polypeptide, for example, polyethylene glycol), or (iv) a polypeptide formed by fusing an additional amino acid sequence to a polypeptide sequence (e.g., a fusion protein formed by a leader sequence or a secretory sequence or a sequence or proprotein sequence for purifying the polypeptide, or by a 6His tag). In light of the teachings herein, such fragment, derivative and analog are within the purview of those skilled in the art.

The antibody of the present invention refers to a polypeptide that has 4-1BB protein binding activity and comprises the above-mentioned CDR region. The term further comprises a variant form of polypeptide that has the same function as the antibody of the present invention and comprises the above CDR region. These variations include (but are not limited to): deletion, insertion and/or substitution of one or more (usually 1-50, preferably 1-30, more preferably 1-20, and most preferably 1-10) amino acids, and addition of one or several (usually within 20, preferably within 10, more preferably within 5) amino acids at the C-terminal and/or N-terminal. For example, in the art, substitution with amino acids having close or similar properties generally does not change the function of protein. As another example, addition of one or several amino acids at the C-terminus and/or N-terminus usually does not change the function of protein. The term also comprises an active fragment and active derivative of the antibody of the present invention.

Variants of the polypeptide include: homologous sequence, conservative variant, allelic variant, natural mutant, induced mutant, protein encoded by a DNA capable of hybridizing to the DNA of the antibody of the present invention under highly or lowly stringent conditions, and polypeptide or protein obtained by using the antiserum against the antibody of the present invention.

The present invention further provides other polypeptides, such as fusion proteins comprising single domain antibodies or fragments thereof. In addition to substantially full-length polypeptides, the present invention further comprises fragments of the single domain antibodies of the present invention. Typically, the fragment has at least about 50 contiguous amino acids, preferably at least about 50 contiguous amino acids, more preferably at least about 80 contiguous amino acids, and most preferably at least about 100 contiguous amino acids of the antibody of the present invention.

In the present invention, "conservative variant of the antibody of the present invention" refers to a polypeptide formed by substitution of at most 10, preferably at most 8, more preferably at most 5, and most preferably at most 3 amino acid sequences with amino acids with similar or closer properties as compared with the amino acid sequence of the antibody of the present invention. These conservative variant polypeptides are preferably produced by amino acid substitutions according to Table A.

TABLE A

| Original residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention further provides a polynucleotide molecule encoding the above-mentioned antibody or fragment thereof or fusion protein thereof. The polynucleotide of the present invention may be in the form of DNA or RNA. The form of DNA comprises cDNA, genomic DNA or synthetic DNA. The DNA can be single-stranded or double-stranded. The DNA can be either a coding strand or a non-coding strand.

The polynucleotide encoding the mature polypeptide of the present invention comprises: a coding sequence that encodes only the mature polypeptide; a coding sequence for the mature polypeptide and various additional coding sequences; a coding sequence for the mature polypeptide (and optional additional coding sequences) and non-coding sequences.

The term "polynucleotide encoding polypeptide" may include a polynucleotide encoding the polypeptide, or may also include an additional coding and/or non-coding sequence.

The present invention further relates to a polynucleotide that hybridizes to the above-mentioned sequence and has at least 50%, preferably at least 70%, more preferably at least 80% identity between the two sequences. The present invention particularly relates to a polynucleotide which is hybridizable under stringent conditions to the polynucleotide of the present invention. In the present invention, "stringent conditions" refer to: (1) hybridization and elution at lower ionic strength and higher temperature, for example, 0.2×SSC, 0.1% SDS, 60° C.; or (2) hybridization in the presence of a denaturing agent, for example, 50% (v/v) formamide, 0.1% calf serum/0.1% Ficoll, 42° C., etc.; or (3) hybridization that occurs only when the identity between two sequences is at least 90%, preferably more than 95%. Moreover, the polypeptide encoded by the hybridizable polynucleotide has the same biological function and activity as the mature polypeptide.

The full-length nucleotide sequence of the antibody of the present invention or its fragment can usually be obtained by PCR amplification, recombination or artificial synthesis. A feasible method is to use artificial synthesis to synthesize related sequences, especially when the fragment length is short. Usually, a fragment with very long sequence is obtained by synthesizing multiple small fragments and then ligating them. In addition, a fusion protein may also be formed by fusing the coding sequence of heavy chain with an expression tag (e.g., 6His).

Once a relevant sequence is obtained, a recombinant method can be used to obtain the relevant sequences in large quantity. Usually, it is cloned into a vector, then transformed into a cell, and then the relevant sequence is isolated from the proliferated host cell by conventional methods. The biomolecules (nucleic acid, protein, etc.) involved in the present invention include biomolecules in isolated form.

At present, the DNA sequence encoding the protein of the present invention (or its fragment, or its derivative) can be obtained completely through chemical synthesis. The DNA sequence can then be introduced into various existing DNA molecules (e.g., vectors) and cells known in the art. In addition, a mutation can also be introduced into the protein sequence of the present invention by chemical synthesis.

The present invention also relates to a vector comprising the above-mentioned appropriate DNA sequence and appropriate promoter or control sequence. These vectors can be used to transform appropriate host cells so that they express the protein.

The host cell may be a prokaryotic cell, such as bacterial cell; or lower eukaryotic cell, such as yeast cell; or a higher eukaryotic cell, such as a mammalian cell. Representative examples are: *Escherichia coli, Streptomyces*; bacterial cell such as *Salmonella typhimurium*; fungal cell such as yeast; insect cell such as *Drosophila* S2 or Sf9; animal cell such as CHO, COS7, 293 cell, etc.

Transformation of host cells with recombinant DNA can be performed using conventional techniques well known to those skilled in the art. When the host is a prokaryotic organism such as *Escherichia coli*, competent cells capable of taking up DNA can be harvested after the exponential growth phase and treated with $CaCl_2$ using procedures well known in the art. Another way is to use $MgCl_2$. The transformation can also be performed by electroporation, if desired. When the host is a eukaryotic organism, the following DNA transfection methods can be used: calcium phosphate co-precipitation method, conventional mechanical methods such as microinjection, electroporation, liposome packaging, etc.

The obtained transformant can be cultured by conventional methods to express the polypeptide encoded by the gene of the present invention. The medium used in the culture can be selected from various conventional media according to the host cells as used. The culture is carried out under conditions suitable for the growth of the host cell. After the host cell has grown to an appropriate cell density, the selected promoter is induced by an appropriate method (e.g., temperature shift or chemical induction), and the cells are cultured for an additional period of time.

The recombinant polypeptide in the above method can be expressed inside the cell, or on the cell membrane, or secreted outside the cell. The recombinant protein can be isolated and purified by various separation methods by taking advantage of its physical, chemical and other properties, if desired. These methods are well known to those skilled in the art. Examples of these methods include, but are not limited to: conventional renaturation treatment, treatment with protein precipitating agent (salting out method), centrifugation, osmotic disruption, supertreatment, ultracentrifugation, molecular sieve chromatography (gel filtration), adsorption chromatography, ion exchange chromatography, high performance liquid chromatography (HPLC) and various other liquid chromatography techniques and combinations of these methods.

The antibody of the present invention can be used alone, or combined or conjugated with a detectable label (for diagnostic purposes), a therapeutic agent, a PK (protein kinase) modifying moiety, or a combination of any of these substances.

The detectable label for diagnostic purposes includes, but is not limited to, fluorescent or luminescent label, radioactive label, MRI (magnetic resonance imaging) or CT (computed tomography) contrast agent, or enzyme capable of producing a detectable product.

The therapeutic agent that can be combined or conjugated with the antibody of the present invention includes, but is not limited to: 1. radionuclide; 2. biological toxicity; 3. cytokine such as IL-2, etc.; 4. gold nanoparticle/nanorod; 5. virus; 6. liposome; 7. nanomagnetic particle; 8. prodrug-activating enzyme (e.g., DT-diaphorase (DTD) or biphenyl-hydrolase-like protein (BPHL)); 9. chemotherapeutic agent (for example, cisplatin) or any form of nanoparticle, etc.

Fusion Protein of the Present Invention

As described herein, the "fusion protein of the present invention" refers to a fusion protein having both the anti-4-1BB nanobody described in the first aspect of the present invention and an Fc fragment of an immunoglobulin.

In the present invention, there is provided a fusion protein, the nanobody fusion protein has a structure as shown in Formula I from the N-terminal to the C-terminal:

$$Z1\text{-}L\text{-}Z2 \quad \text{(Formula I)}$$

in the Formula,

Z1 represents one or more VHH chains of the anti-4-1BB nanobody according to the first aspect of the present invention;

Z2 represents an Fc fragment of an immunoglobulin;

L represents an optional linker sequence.

Preferably, the immunoglobulin can be IgG1, IgG2, IgG3 or IgG4, etc. (preferably IgG1, IgG2 or IgG4), or a different mutant type of IgG1.

In one embodiment, the fusion protein is a dimer, and the dimer is formed by a disulfide bond between Fc fragments in Z2.

In one embodiment, the L has an amino acid sequence selected from a group consisting of GGGGS, $(GGGGS)_2$, $(GGGGS)_3$, $(GGGGS)_4$, $(GGGGS)_5$, or combination thereof.

In a preferred embodiment, the Z2 has an amino acid sequence as set forth in SEQ ID NO: 167.

In another embodiment, the Z2 has an amino acid sequence identical or substantially identical to the amino acid sequence set forth in SEQ ID NO: 167.

Preferably, the term "substantially identical" means that at most 50 (preferably 1-20, more preferably 1-10, more preferably 1-5, most preferably 1-3) amino acids are different, wherein the differences comprise substitution, deletion or addition of amino acids.

Preferably, the term "substantially identical" means that the amino acid sequence has a sequence identity of at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the corresponding amino acid sequence.

In a preferred embodiment of the present invention, the amino acid sequence of the fusion protein comprises from the N-terminal to the C-terminal: the sequence set forth in any of SEQ ID NO: 1-40 and the sequence set forth in SEQ ID NO: 167;

wherein, any amino acid sequence in the above amino acid sequences further comprises a derived sequence that is optionally subjected to addition, deletion, modification and/or substitution of 1-8 (preferably 1-5, more preferably 1-3) amino acid residues, and is capable of retaining 4-1 BB binding affinity.

The fusion protein of the present invention has the advantages of high dual-target binding affinity and strong specificity, thereby further enhancing the anti-tumor immune function.

Pharmaceutical Composition

The present invention also provides a composition. Preferably, the composition is a pharmaceutical composition, which comprises the above-mentioned antibody or its active fragment or its fusion protein, and a pharmaceutically acceptable carrier. Generally, these materials can be formulated in a non-toxic, inert and pharmaceutically acceptable aqueous carrier medium, wherein the pH is usually about 5-8, preferably about 6-8, although the pH value can be changed according to the nature of the substances formulated and the conditions to be treated. The prepared pharmaceutical composition can be administered by conventional routes, including (but not limited to): intratumoral, intraperitoneal, intravenous, or topical administration.

The pharmaceutical composition of the present invention can be directly used for binding 4-1BB protein molecules, and thus can be used for treating a tumor. In addition, an additional therapeutic agent may also be used concomitantly.

The pharmaceutical composition of the present invention comprises a safe and effective amount (e.g., 0.001-99 wt %, preferably 0.01-90 wt %, more preferably 0.1-80 wt %) of the above-mentioned single-domain antibody (or its conjugate) of the present invention and a pharmaceutical acceptable carrier or excipient. Such carrier includes, but is not limited to: saline, buffer, dextrose, water, glycerol, ethanol, and combination thereof. The pharmaceutical formulation should match the mode of administration. The pharmaceutical composition of the present invention can be prepared in the form of injection, for example, by conventional methods using physiological saline or aqueous solution containing glucose and other adjuvants. The pharmaceutical composition such as injection or solution is preferably produced under sterile conditions. The active ingredient is administered in a therapeutically effective amount, for example about 10 μg/kg body weight to about 50 mg/kg body weight per day. In addition, the polypeptide of the present invention can also be used with an additional therapeutic agent.

When using the pharmaceutical composition, a safe and effective amount of the immunoconjugate is administered to a mammal, wherein the safe and effective amount is usually at least about 10 μg/kg body weight, and in most cases no more than about 50 mg/kg body weight; preferably, the dosage is about 10 μg/kg body weight to about 10 mg/kg body weight. Nevertheless, factors such as the route of administration and the health status of the patient should also be considered for the specific dosage, which are within the skill of skilled physicians.

Labeled Nanobody

In a preferred embodiment of the present invention, the nanobody has a detectable label. More preferably, the label is selected from a group consisting of isotope, colloidal gold label, colored label or fluorescent label.

Colloidal gold labeling can be performed using methods known to those skilled in the art. In a preferred embodiment of the present invention, the anti-4-1BB nanobody is labeled with colloidal gold to obtain a colloidal gold-labeled nanobody.

The anti-4-1BB nanobody of the present invention has good specificity and high titer.

Detection Method

The present invention also relates to a method for detecting 4-1BB protein. The method comprises steps roughly as follows: obtaining a cell and/or tissue sample; dissolving the sample in a medium; detecting the level of 4-1BB protein in the dissolved sample.

In the detection method of the present invention, the sample used is not particularly limited, and a representative example is a cell-containing sample present in a cell preservation solution.

Kit

The present invention also provides a kit comprising the antibody (or fragment thereof) or fusion protein or detection plate of the present invention. In a preferred embodiment of the present invention, the kit further comprises a container, an instruction manual, a buffer and so on.

The present invention also provides a detection kit for detecting the level of 4-1BB, which comprises an antibody capable of recognizing 4-1BB protein, a lysis medium for dissolving sample, general reagents and buffers required for detection, such as various buffers, detection labels, detection substrates, etc. The test kit may be an in vitro diagnostic device.

USES

As mentioned above, the nanobody of the present invention has a wide range of biological and clinical application values, and its uses involves the diagnosis and treatment of diseases related to 4-1BB, basic medical research, biological research and other fields. A preferred use is for clinical diagnosis and targeted therapy against 4-1BB.

Beneficial Effects of the Present Invention

The present invention achieves any one or more of the following technical effects:

1) The nanobody of the present invention has a small molecular weight.
2) The nanobody of the present invention can highly specifically bind to human 4-1BB protein, and at the same time cross-bind to cynomolgus monkey protein.
3) The nanobody of the present invention needs external cross-linking to exert activation function, and thus has excellent activity and safety.
4) The nanobody of the present invention does not block the binding of 4-1BB ligand to 4-1BB in the natural state.
5) As an anti-4-1BB agonistic molecule, Urelumab has clinical hepatotoxicity due to its super activation activity. An important advantage of the antibody of the present invention is that it is different from Urelumab and Utomilumab in site for binding to 4-1BB, and its activation activity is between those of Urelumab and Utomilumab.

Figure 1A:
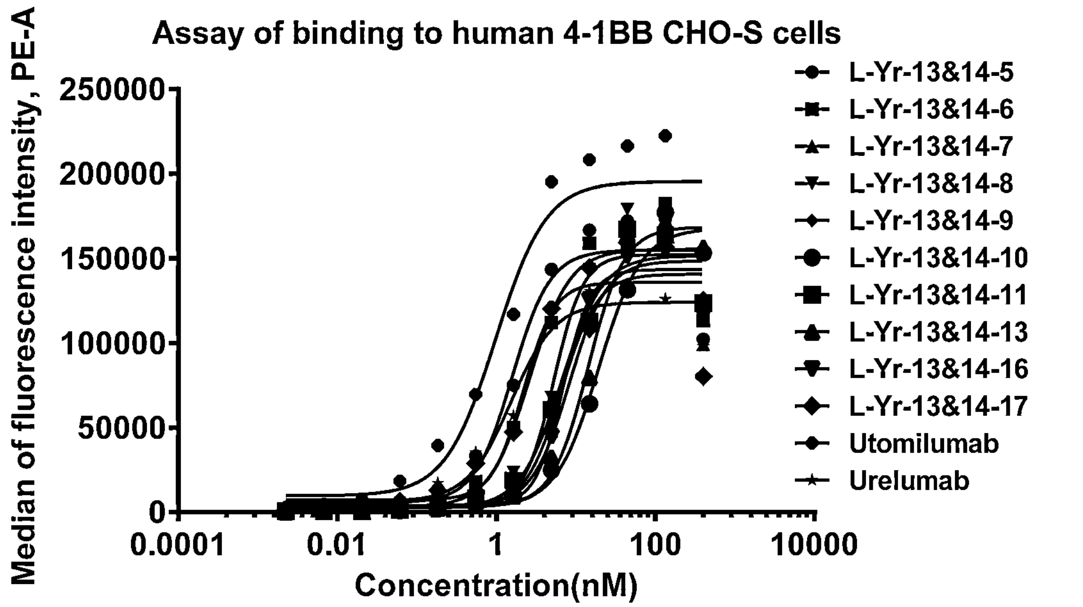
FIG. 1A shows the detection results of the first batch of 4-1BB antibodies of the present invention in binding to CHO cells stably expressing human 4-1BB.

In the present invention, the involved anti-4-1BB nanobodies and the sequence numbers of their CDRs are shown in Table B below.

TABLE B

| Sequence numbers corresponding to nanobodies of the present invention (SEQ ID NO:) | | | | |
|---|---|---|---|---|
| Antibody name | VHH | CDR1 | CDR2 | CDR3 |
| A-Na-16 | 1 | 41 | 81 | 121 |
| A-Na-18 | 2 | 42 | 82 | 122 |
| A-Na-19 | 3 | 43 | 83 | 123 |
| A-Ye-02 | 4 | 44 | 84 | 124 |
| A-Ye-03 | 5 | 45 | 85 | 125 |
| A-Ye-04 | 6 | 46 | 86 | 126 |
| A-Ye-05 | 7 | 47 | 87 | 127 |
| A-Ye-10 | 8 | 48 | 88 | 128 |
| A-Ye-13 | 9 | 49 | 89 | 129 |
| A-Ye-14 | 10 | 50 | 90 | 130 |
| A-Ye-15 | 11 | 51 | 91 | 131 |
| A-Ye-18 | 12 | 52 | 92 | 132 |
| A-Ye-19 | 13 | 53 | 93 | 133 |
| A-Ye-21 | 14 | 54 | 94 | 134 |
| A-Ye-22 | 15 | 55 | 95 | 135 |
| A-Ye-23 | 16 | 56 | 96 | 136 |
| A-Ye-25 | 17 | 57 | 97 | 137 |
| A-Ye-27 | 18 | 58 | 98 | 138 |
| A-Ye-30 | 19 | 59 | 99 | 139 |
| A-Ye-33 | 20 | 60 | 100 | 140 |
| A-Ye-20 | 21 | 61 | 101 | 141 |
| A-Ye-35 | 22 | 62 | 102 | 142 |
| L-Yr-13&14-01 | 23 | 63 | 103 | 143 |
| L-Yr-13&14-02 | 24 | 64 | 104 | 144 |
| L-Yr-13&14-03 | 25 | 65 | 105 | 145 |
| L-Yr-13&14-05 | 26 | 66 | 106 | 146 |
| L-Yr-13&14-06 | 27 | 67 | 107 | 147 |
| L-Yr-13&14-07 | 28 | 68 | 108 | 148 |
| L-Yr-13&14-08 | 29 | 69 | 109 | 149 |
| L-Yr-13&14-09 | 30 | 70 | 110 | 150 |
| L-Yr-13&14-10 | 31 | 71 | 111 | 151 |
| L-Yr-13&14-11 | 32 | 72 | 112 | 152 |
| L-Yr-13&14-12 | 33 | 73 | 113 | 153 |
| L-Yr-13&14-13 | 34 | 74 | 114 | 154 |
| L-Yr-13&14-16 | 35 | 75 | 115 | 155 |
| L-Yr-13&14-17 | 36 | 76 | 116 | 156 |
| Hu-A-NA-19-1 | 37 | 77 | 117 | 157 |
| Hu-A-NA-19-2 | 38 | 78 | 118 | 158 |
| HZ-L-Yr-13&14-16-1 | 39 | 79 | 119 | 159 |
| HZ-L-Yr-13&14-16-2 | 40 | 80 | 120 | 160 |

Wherein, the CDRs of each nanobody are defined by the IMGT numbering system.

TABLE C

Sequences involved in the present invention

| SEQ ID NO: | Amino acid sequence |
|---|---|
| 1 | QVQLVESGGGLVPPGESLRLSCAASGAIFRINTGAWYRQAPG KQRELVASLTTYGKTTYADFVKGRFTISRDDARNTVSLQMN SLKPEDTAIYYCHIGPEPRYGYWGQGTQVTVSS |
| 2 | QVQLVESGGGLVPPGESLRLSCAASGAIFRINTGAWYRQAPG KQRELVASLTTYGKTTYADFVKGRFTISRDDAENTVSLQMN SLKPEDTAIYYCHIGPEPRYGYWGQGTQVTVSS |
| 3 | QVQLVESGGGLVPPGESLRLSCAASGAIFRINTGAWYRQAPG KQRELVASLTTYGKTTYADFVKGRFTISRDDAKNTVYLQMN SLKPEDTAIYYCHIGPEPRYGYWGQGTQVTVSS |
| 4 | QVQLQESGGGLVQVGGSLRLSCAASGFTFDDYAIGWFRQAP GKEREGVLCISSSGGSTYYADSVKGRFTISRDNAKNTVYLQ MTNLKPEDTAVYLCGAPRDCSLYTGDDYWGQGTQVTVSS |
| 5 | QVQLQESGGGLVQAGGSLRLSCAASGFTLDYYAIGWFRQAP GKEREGVLCISSSGETTYYSDSVKGRFTISRDNAKNKVYLQM NSLKPEDTAVYYCGAELLGSGEGCYVWSRDGSYWGQGTQV TVSS |
| 6 | QVQLQESGGGLVPPGESLRLSCAASGAIFRINTGAWYRQAPG KQRELVASLTTYGKTTYADFVKGRFTISRDDAKNTVSLQMN SLKPEDTAIYYCHIGPEPRYGYWGQGTQVTVSS |
| 7 | QVQLQESGGGLVQVGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGQGTQVTVSS |
| 8 | QVQLQESGGGLVEPGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGPGTQVTVSS |
| 9 | EVQLQESGGGLVQAGGSLRLSCAASGFTFDDYAIGWFRQAP GKEREGVLCISSSGGSTYYADSVKGRFTISRDNAKNTVYLQ MTNLKPEDTAVYLCGAPRDCSYYTGDDYWGQGTQVTVSS |
| 10 | QVQLQESGGGLVQPGGSLRLSCAASGFSLGLYAIGWFRQAP GKEREWVSCIMSSDSSAYYADSVKGRFTVSRDNAKNTVYLQ MNRLKPEDTAVYYCAAPQSDCFHYSENDYWGQGTQVTVSS |
| 11 | QVQLQESGGGLVQPGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGQGTQVTVSS |
| 12 | QVQLQESGGGLVQAGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGQGTQVTVSS |
| 13 | QVQLQESGGGLVQAGGSLRLSCAASGFSLGLYAIGWFRQAP GKEREWVSCIMSSDSSAYYADSVKGRFTVSRDNAKNTVYLQ MNRLKPEDTAVYYCAAPQSDCFHYSENDYWGQGTQVTVSS |
| 14 | QVQLQESGGGLVQPGGSLRLSCAASGFSLDYYAIGWFRQAP GKEREWVSCIMSSDSSAYYADSVKGRFTISRDNAKNLVYLR MNSLKPEDTAVYYCTAPRSDCFHYGENDYWGQGTQVTVSS |
| 15 | QVQLQESGGGLVQAGGSLRLSCAASGFSLDYYAIGWFRQAP GKEREWVSCITASDSSAYYADSVKGRFTISRDNAKNTVYLR MNSLKPEDTAVYYCAAPRSDCFHYGENDYWGQGTQVTVSS |
| 16 | QVQLQESGGGLVQPGGSLRLSCAASGFSLGLYAIAWFRQAP GKEREWVSCIEKSDSSAYYADSVKGRFTVSRDNAKNTVDLQ MNRLSPEDTAVYYCAAPQSDCFHYKENDYWGQGTQVTVSS |
| 17 | QVQLQESGGGLVQVGGSLRLSCAASGFTFDDYAIGWFRQAP GKEREGVLCISSSGGSTYYADSLKGRFTISRDNAKNTVYLQM TNLKPEDTAVYLCGAPRDCSLYTGDDYWGQGTQVTVSS |
| 18 | QVQLQESGGGLVQPGGSLRLSCAASGFSLGLYAIGWFRQAP GKEREWVSCIMSSDSSAYYADSVKGRFTVSRDNAKNTVYLQ MTNLKPEDTAVYLCGAPRDCSRYSSDDYWGQGTQVTVSS |
| 19 | QVQLQESGGALVQAGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGQGTQVTVSS |

TABLE C-continued

Sequences involved in the present invention

| SEQ ID NO: | Amino acid sequence |
|---|---|
| 20 | QVQLQESGGGLVQVGGSLRLSCAASGFTFDDYAIGWFRQAP GKEREGVLCISSSGGSTYYADSVKGRFTISRDNAKNTVYLQ MTNLKPEDTAVYLCGAPRDCSLYTGDDYWGPGTQVTVSS |
| 21 | QVQLQESGGGLVQAGGSLRLSCAASGFTFDDYAIGWFRQAP GKEREGVLCISSSGGSTYYADSVKGRFTISRDNAKNTVYLQ MTNLKPEDTAVYLCGAPRDCSYYTSDDYWGQGTQVTVSS |
| 22 | QVQLQESGGALVQPGGSLRLSCAASGFTFDDYAIGWFRQAP GKEREGVLCISSSGGSTYYADSVKGRFTISRDNAKNTVYLQ MTNLKPEDTAVYLCGAPRDCSRYSSDDYWGQGTQVTVSS |
| 23 | QVQLQESGGGLVQAGGSLRLSCAASGSFNAMGWWRQAPG KQREFVAIITRDGSTNLADSVKGRFTISSDNAKNTWFLQMNS LKPEDTAVYYCSASDYGSSLYYWGQGTQVTVSS |
| 24 | QVQLQESGGGLVQAGGSLRLSCAASGGTFSITAMGWYRQAP GQQRELVAAIASGDGATNYADFVKGRFTISRDNAKNTMFLQ MNSLKPEDSAVYYCYARTGYGSSWPMGHEYDYWGQGTQV TVSS |
| 25 | QVQLQESGGGLVQPGESLRLSCDSGRIFSYNFMGWYRQAPG KQRELVASITWGGTIKYADSVKGRFTISRHDAENTVYLQMN SLKSEDTAVYYCHAATDTGVIYWGQGTQVTVSS |
| 26 | QVQLQESGGGLVQAGGSLRLSCAASGRTLSGYVMGWFRQA SGKERELVAAISSGGSTYYEDSVKGRFTISRDNAKNTMYLQ MNSLKPEDTAVYYCAADPRRLTGLYDYWGQGTQVTVSS |
| 27 | QVQLQESGGGLVEAGGSLRLSCAASGSIFSINVMGWYRQAP GKQRELVAVITSDYSTNYADSVKGRFTISRDNAKNTVYLQM NSLKPEDTAVYHCAATGYGSSPWYWGQGTQVTVSS |
| 28 | QVQLQESGGGLVQAGDSLRLSCAASGSTFGITAMGWYRQPP GKQRELVAAIIMSDGDTNYQDSVKGRFTISRDNAKNTMYLQ MNSLKLEDTAVYYCYARTGYGSGRLMGHEYDYWGQGTQV TVSS |
| 29 | QVQLQESGGGLVQPGGSLRLSCAASGSTFSISAMGWYRQPP GKQRELVALIIMSDGDTNYQDSVKGRFTISRDNANNTMYLQ MNSLKLEDTAVYYCYARTGYGSGRLMGHEYDYWGQGTQV TVSS |
| 30 | QVQLQESGGGLVQAGGSLKLSCAASGSTFSISAMGWYRQAP GKQRELVAAIVIGDGDTNYADSVKGRFTISRDNAKNTMYLQ MNSLKPEDTAVYYCYARTGYGSSWLMGHEYDYWGQGTQV TVSS |
| 31 | QVQLQESGGGLVQAGGSLRLSCAASGSTFSITAMGWYRQAP GQQRELVAAIASGDGATNYADFVKGRFTISRDNAKNTMFLQ MNSLKPEDSAVYYCYARTGYGSSWLMGHEYDYWGQGTQV TVSS |
| 32 | QVQLQESGGGLVQAGDSLRLSCAASGSTFSITAMGWYRQPP GKQRELVAAIIMSDGDTNYQDSVKGRFTISRDNAKNTMYLQ MNSLKLEDTAVYYCYARTGYGSGRLMGHEYDYWGQGTQV TVSS |
| 33 | QVQLQESGGGLVQAGDSLRLSCAASGSTFSITAMGWYRQPP GKQRELVAAIIMSDGDTNYQDSVKGRFTISRDNAKNTMYLQ MNSLKPEDTAVYYCYARTGYGSGWLEGHEYDYWGQGTQV TVSS |
| 34 | QVQLQESGGGLVQAGDSLRLSCAASGSTFSITAMGWYRQPP GKQRELVASIITGDGDTNYADSVKGRFTISRDNAKNTMYLQ MNSLKPEDTAVYYCYARTGYGSSWLMGHEYDYWGQGTQV TVSS |
| 35 | QVQLQESGGGLVQAGDSLRLSCAASGSTFSIVAMGWYRQAP GKQRELVASIITGDGDTNYADSVKGRFTISRDNAKNTMYLQ MNSLKPEDTAVYYCYARTGYGSSWLMGHEYDYWGQGTQV TVSS |

TABLE C-continued

| Sequences involved in the present invention | |
|---|---|
| SEQ ID NO: | Amino acid sequence |
| 36 | QVQLQESGGGLVQAGGSLRLSCAASRSIFSSYVMAWYRQAP GKERELVALIRYGGSTDYADSVKGRFTISRDNSKNTLILQMN SLKPEDTAMYYCAASKSAYIFDDRDYWGQGTQVTVSS |
| 37 | EVQLVESGGGLVKPGGSLRLSCAASGAIFRINTGAWYRQAP GKQRELVASLTTYGKTTYADFVKGRFTISRDDSKNTLYLQM NSLKTEDTAVYYCHIGPEPRYGYWGQGTLVTVSS |
| 38 | EVQLVESGGGLVKPGGSLRLSCAASGAIFRINTGAWYRQAP GKGLELVASLTTYGKTTYADFVKGRFTISRDDSKNTLYLQM NSLKTEDTAVYYCHIGPEPRYGYWGQGTLVTVSS |
| 39 | QVQLVESGGGVVQPGRSLRLSCAASGSTFSIVAMGWYRQAP GKQRELVASIITGDGDTNYADSVKGRFTISRDNSKNTMYLQ MNSLKPEDTAVYYCYARTGYGSSWLMGHEYDYWGQGTQV TVSS |
| 40 | QVQLVESGGGVVQPGRSLRLSCAASGSTFSIVAMGWYRQAP GKGLELVASIITGDGDTNYADSVKGRFTISRDNSKNTMYLQ MNSLRAEDTAVYYCYARTGYGSSWLMGHEYDYWGQGTQV TVSS |
| 41 | AASGAIFRINTGA |
| 42 | AASGAIFRINTGA |
| 43 | AASGAIFRINTGA |
| 44 | AASGFTFDDYAIG |
| 45 | AASGFTLDYYAIG |
| 46 | AASGAIFRINTGA |
| 47 | AASGFTFDDYAIG |
| 48 | AASGFTFDDYAIG |
| 49 | AASGFTFDDYAIG |
| 50 | AASGFSLGLYAIG |
| 51 | AASGFTFDDYAIG |
| 52 | AASGFTFDDYAIG |
| 53 | AASGFSLGLYAIG |
| 54 | AASGFSLDYYAIG |
| 55 | AASGFSLDYYAIG |
| 56 | AASGFSLGLYAIA |
| 57 | AASGFTFDDYAIG |
| 58 | AASGFSLGLYAIG |
| 59 | AASGFTFDDYAIG |
| 60 | AASGFTFDDYAIG |
| 61 | AASGFTFDDYAIG |
| 62 | AASGFTFDDYAIG |
| 63 | AASGSFNAMG |
| 64 | AASGGTFSITAMG |
| 65 | DSGRIFSYNFMG |
| 66 | AASGRTLSGYVMG |
| 67 | AASGSIFSINVMG |

TABLE C-continued

| Sequences involved in the present invention | |
|---|---|
| SEQ ID NO: | Amino acid sequence |
| 68 | AASGSTFGITAMG |
| 69 | AASGSTFSISAMG |
| 70 | AASGSTFSISAMG |
| 71 | AASGSTFSITAMG |
| 72 | AASGSTFSITAMG |
| 73 | AASGSTFSITAMG |
| 74 | AASGSTFSITAMG |
| 75 | AASGSTFSIVAMG |
| 76 | AASRSIFSSYVMA |
| 77 | AASGAIFRINTGA |
| 78 | AASGAIFRINTGA |
| 79 | AASGSTFSIVAMG |
| 80 | AASGSTFSIVAMG |
| 81 | SLTTYGKTTYADFVKG |
| 82 | SLTTYGKTTYADFVKG |
| 83 | SLTTYGKTTYADFVKG |
| 84 | CISSSGGSTYYADSVKG |
| 85 | CISSSGETTYYSDSVKG |
| 86 | SLTTYGKTTYADFVKG |
| 87 | CISSSGGSTYYADSVKG |
| 88 | CISSSGGSTYYADSVKG |
| 89 | CISSSGGSTYYADSVKG |
| 90 | CIMSSDSSAYYADSVKG |
| 91 | CISSSGGSTYYADSVKG |
| 92 | CISSSGGSTYYADSVKG |
| 93 | CIMSSDSSAYYADSVKG |
| 94 | CIMSSDSSAYYADSVKG |
| 95 | CITASDSSAYYADSVKG |
| 96 | CIEKSDSSAYYADSVKG |
| 97 | CISSSGGSTYYADSLKG |
| 98 | CIMSSDSSAYYADSVKG |
| 99 | CISSSGGSTYYADSVKG |
| 100 | CISSSGGSTYYADSVKG |
| 101 | CISSSGGSTYYADSVKG |
| 102 | CISSSGGSTYYADSVKG |
| 103 | IITRDGSTNLADSVKG |
| 104 | AIASGDGATNYADFVKG |
| 105 | SITWGGTIKYADSVKG |

TABLE C-continued

| Sequences involved in the present invention | |
|---|---|
| SEQ ID NO: | Amino acid sequence |
| 106 | AISSGGSTYYEDSVKG |
| 107 | VITSDYSTNYADSVKG |
| 108 | AIIMSDGDTNYQDSVKG |
| 109 | LIIMSDGDTNYQDSVKG |
| 110 | AIVIGDGDTNYADSVKG |
| 111 | AIASGDGATNYADFVKG |
| 112 | AIIMSDGDTNYQDSVKG |
| 113 | AIIMSDGDTNYQDSVKG |
| 114 | SIITGDGDTNYADSVKG |
| 115 | SIITGDGDTNYADSVKG |
| 116 | LIRYGGSTDYADSVKG |
| 117 | SLTTYGKTTYADFVKG |
| 118 | SLTTYGKTTYADFVKG |
| 119 | SIITGDGDTNYADSVKG |
| 120 | SIITGDGDTNYADSVKG |
| 121 | HIGPEPRYGY |
| 122 | HIGPEPRYGY |
| 123 | HIGPEPRYGY |
| 124 | GAPRDCSLYTGDDY |
| 125 | GAELLGSGEGCYVWSRDGSY |
| 126 | HIGPEPRYGY |
| 127 | GAPRDCSRYSSDDY |
| 128 | GAPRDCSRYSSDDY |
| 129 | GAPRDCSYYTGDDY |
| 130 | AAPQSDCFHYSENDY |
| 131 | GAPRDCSRYSSDDY |
| 132 | GAPRDCSRYSSDDY |
| 133 | AAPQSDCFHYSENDY |
| 134 | TAPRSDCFHYGENDY |
| 135 | AAPRSDCFHYGENDY |
| 136 | AAPQSDCFHYKENDY |
| 137 | GAPRDCSLYTGDDY |
| 138 | GAPRDCSRYSSDDY |
| 139 | GAPRDCSRYSSDDY |
| 140 | GAPRDCSLYTGDDY |
| 141 | GAPRDCSYYTSDDY |
| 142 | GAPRDCSRYSSDDY |
| 143 | SASDYGSSLYY |

TABLE C-continued

| Sequences involved in the present invention | |
|---|---|
| SEQ ID NO: | Amino acid sequence |
| 144 | YARTGYGSSWPMGHEYDY |
| 145 | HAATDTGVIY |
| 146 | AADPRRLTGLYDY |
| 147 | AATGYGSSPWY |
| 148 | YARTGYGSGRLMGHEYDY |
| 149 | YARTGYGSGRLMGHEYDY |
| 150 | YARTGYGSSWLMGHEYDY |
| 151 | YARTGYGSSWLMGHEYDY |
| 152 | YARTGYGSGRLMGHEYDY |
| 153 | YARTGYGSGWLEGHEYDY |
| 154 | YARTGYGSSWLMGHEYDY |
| 155 | YARTGYGSSWLMGHEYDY |
| 156 | AASKSAYIFDDRDY |
| 157 | HIGPEPRYGY |
| 158 | HIGPEPRYGY |
| 159 | YARTGYGSSWLMGHEYDY |
| 160 | YARTGYGSSWLMGHEYDY |
| 161 | GTCCTGGCTGCTCTTCTACAAGG |
| 162 | GGTACGTGCTGTTGAACTGTTCC |
| 163 | CTAGTGCGGCCGCCTGGAGACGGTGACCTGGGT |
| 164 | CGCGGATCCCAGGTGCAGCTGCAGGAGTCTGGRGGAGG |
| 165 | ATTTTTACTGCTGTTTTATTCGCAGCATCCTCCGCATTAGC TAAAAGAGAGGCTGAAGCACAGGTGCAGCTGCAGGAGTC TGGRGGAGG |
| 166 | AGTTGTCAGTTCCTGTGCCCCCCCTCCTCCCGCGCCACCTC CGCCCGCACCTCCGCCACCACTGGAGACGGTGACCTGGGT |
| 167 (Fc fragment of human IgG1) | THTCPPCPAPEAAGGPSVFLFPPKPKDTLMISRTPEVTCVVVD VSHEDPEVKFNWYVDGVEVHNAKTKPREEQYNSTYRVVSV LTVLHQDWLNGKEYKCKVSNKALPAPIEKTISKAKGQPREP QVYTLPPSREEMTKNQVSLTCLVKGFYPSDIAVEWESNGQPE NNYKTTPPVLDSDGSFFLYSKLTVDKSRWQQGNVFSCSVMH EALHNHYTQKSLSLSPG |
| 168 (human 4-1BB protein) | QDPCSNCPAGTFCDNNRNQICSPCPPNSFSSAGGQRTCDICRQ CKGVFRTRKECSSTSNAECDCTPGFHCLGAGCSMCEQDCKQ GQELTKKGCKDCCFGTFNDQKRGICRPWTNCSLDGKSVLVN GTKERDVVCGPSPLG |
| 169 (Amino acid sequence of anti-4-1BB antibody in crystal complex) | QVQLVESGGGVVQPGRSLRLSCAASGSTFSIVAMGWYRQAP GKQRELVASIITGDGDTNYADSVKGRFTISRDNSKNTMYLQ MNSLKPEDTAVYYCYARTGYGSSWLMGHEYDYWGQGTQV TVSSLG |
| 170 (Framework region 1) | EVQLVESGGGLVKPGGSLRLSC |
| 171 (Framework region 2) | WYRQAPGKQRELVA |

TABLE C-continued

Sequences involved in the present invention

| SEQ ID NO: | Amino acid sequence |
|---|---|
| 172 (Framework region 2) | WYRQAPGKGLELVA |
| 173 (Framework region 3) | RFTISRDDSKNTLYLQMNSLKTEDTAVYYC |
| 174 (Framework region 4) | WGQGTLVTVSS |

Notes:
In Table C, SEQ ID NO: 41-160 are CDR sequences, in which some sequences may be the same, and different numbers are used for the convenience of expression.

SPECIFIC MODELS FOR CARRYING OUT THE PRESENT INVENTION

The present invention is further illustrated in conjunction with specific examples below. It should be understood that these examples are only used to illustrate the present invention and are not intended to limit the scope of the present invention. The experimental methods without giving specific conditions in the following examples are usually carried out according to conventional conditions, such as the conditions described in Sambrook et al., Molecular cloning: Laboratory Manual (New York: Cold Spring Harbor Laboratory Press, 1989), or according to the conditions recommended by the manufacturer. Percentages and parts are by weight unless otherwise indicated.

Example 1: Construction of Nanobody Library 1.1 Animal Immunization 1 mg of human 4-1BB antigen (purchased from AcroBiosystems) was mixed with an equal volume of Freund's adjuvant, and used to immunize 2 alpacas (Llama), once a week, and immunization was performed 4 times in total to stimulate B cells to express antigen-specific nanobody. After the 4 times of immunization, 50 ml of alpaca peripheral blood was extracted, and lymphocytes were separated by lymphocyte separation medium. Total RNA was extracted using RNA extraction reagent Trizol (purchased from Invitrogen). Alpaca total cDNA was obtained by reverse transcription using a cDNA synthesis kit (purchased from Invitrogen).

1.2 Amplification of Nanobody Gene

In the first round of PCR, IgG2 and IgG3 sequences were amplified from the cDNA:

TABLE 1

First-round PCR primers

| Name | Sequence (5' to 3') | SEQ ID NO: |
|---|---|---|
| Upstream primer | GTCCTGGCTGCTCTTCTACAAGG | 161 |
| Downstream primer | GGTACGTGCTGTTGAACTGTTCC | 162 |

The first round PCR products were subjected to agarose gel electrophoresis, and the fragment at 750 bp recovered by cutting the gel was used for the second round of VHH sequence amplification. The primers for the second round of PCR amplification were as follows:

TABLE 2

Second-round PCR primers

| Name | Sequence (5' to 3') | SEQ ID NO: |
|---|---|---|
| Upstream primer | CTAGTGCGGCCGCCTGGAGACGGTGACCTGGGT | 163 |
| Downstream primer | CGCGGATCCCAGGTGCAGCTGCAGGAGTCTGGRGGAGG | 164 |

The second-round PCR product was used as a template to perform the third-round PCR, so that a homology arm was added to the VHH gene. The primers for the third-round PCR amplification were as follows:

TABLE 3

Third-round PCR primers

| Name | Sequence (5' to 3') | SEQ ID NO: |
|---|---|---|
| Upstream primer | ATTTTTACTGCTGTTTTATTCGCAGCATCCTCCGCATTAGCTAAAAGAGAGGCTGAAGCACAGGTGCAGCTGCAGGAGTCTGGRGGAGG | 163 |
| Downstream primer | AGTTGTCAGTTCCTGTGCCCCCCCTCCTCCCGCGCCACCTCCGCCCGCACCTCCGCCACCACTGGAGACGGTGACCTGGGT | 164 |

The target fragment was recovered using a PCR purification kit (purchased from QIAGEN).

1.3 Library Construction

The linearized yeast display vector and the third-round PCR product were mixed and electrotransformed into *Saccharomyces cerevisiae* (ATCC® 20828) to construct anti-4-1BB nanobody libraries from two alpacas.

Example 2: Screening of 4-1BB Nanobodies 2.1 Biotinylation Labeling of Human 4-1BB Protein An appropriate volume of double-distilled water was taken to dissolve human 4-1BB protein (purchased from AcroBiosystems), and biotin was dissolved according to the product instructions of biotin labeling kit (purchased from Thermo), mixed with the protein solution, and incubated at 4° C. for 2 hours. The excess biotin was removed by using a desalting column (purchased from Thermo), in which the operations of desalting column pretreatment and sample collection were all referred to the steps described in the product manual.

2.2 MACS (Magnetic-Activated Cell Sorting) Enrichment of Yeast Capable of Specifically Binding to 4-1BB The VHH library constructed in Example 1 was inoculated on SD-CAA expansion medium (1 L of SD-CAA expansion medium contained 6.7 g of YNB, 5 g of casamino acids, 13.62 g of $Na_2HPO_4 \cdot 12H_2O$, 7.44 g of $NaH_2PO_4$, and 2% glucose), and cultured at 30° C., 225 rpm overnight. An appropriate amount of yeast cells was taken, centrifuged at 3000 rpm×5 min to remove medium, and the yeast cells were resuspended with SD-CAA induction medium, and induced overnight. The library concentration after induction was measured, and an appropriate amount of the yeast cells were taken and centrifuged to remove the medium. The yeast cells were resuspended in 50 ml of washing buffer (PBS+0.5% BSA+2 mM EDTA), and centrifuged to remove the supernatant. The yeast cells were resuspended in 10 ml of washing buffer.

Biotin-labeled 4-1BB protein (with a final concentration of 100 mM) were added, incubated at room temperature for 30 min, the yeast cells were collected by centrifugation, and the yeast cells were washed 3 times with 50 ml of washing buffer. The yeast cells were resuspended with 5 ml of washing buffer, added with 200 μl of SA magnetic beads (purchased from Miltenyi), and incubated upside-down for 10 min. The mixture of yeast cells and magnetic beads was washed 3 times with washing buffer, and the mixture was added to an LS column (purchased from Miltenyi). The LS column was placed on a magnetic stand and washed with washing buffer to remove non-specifically bound yeast cells. The column was taken out from the magnetic stand, and added with washing buffer to elute the yeast cells. The eluted yeast cells were centrifuged and transferred to 200 ml of SD-CAA expansion medium to perform amplification.

2.3 Flow Cytometric Sorting to Obtain High-Affinity Yeast Cells

The yeast cells enriched by MACS were inoculated in SD-CAA expansion medium and cultured overnight at 30° C. and 225 rpm in a shake flask. The yeast cells were resuspended with SD-CAA induction medium (1 L of SD-CAA induction medium contained 6.7 g of YNB, 5 g of casamino acids, 13.62 g of $Na_2HPO_4 \cdot 12H_2O$, 7.44 g of $NaH_2PO_4$, as well as 2% galactose, 2% raffinose and 0.1% glucose) and induced overnight. The 1:200 diluted anti-c-Myc murine antibody (purchased from Thermo) and 100 nM biotin-labeled 4-1BB antigen were added, and incubated at room temperature for 10 min. PBS was added to wash the yeast cells 3 times, the 1:500 diluted goat anti-mouse IgG (H+L) Alexa Fluor Plus 488 (purchased from Invitrogen) and streptavidin APC-conjugated fluorescent antibody (purchased from Invitrogen) were added, and incubated at 4° C. in the dark for 15 min. 2 ml of PBS was added to resuspend the cells, and BD FACS Arial instrument was used to sort and obtain the yeast cells with high binding ability to 4-1BB antigen.

2.4 Acquisition of Gene of 4-1BB Nanobody Candidate Molecule

The yeast cells with high binding ability to 4-1BB antigen obtained by MACS and FACS enrichment was cultured overnight in SD-CAA amplification medium at 30° C. and 225 rpm, and the plasmid was extracted with a yeast plasmid extraction kit (purchased from Tiangen). The plasmid was electrotransformed into Top10 competent cells (purchased from Tiangen), coated on an ampicillin-resistant plate, and cultured overnight at 37° C. Single clone was picked and sequenced to obtain the VHH gene sequence.

Example 3: Construction and Expression Purification of Heavy Chain Antibody Fusion Protein 3.1 Construction of Antibody Gene into pCDNA3.1 Expression Vector The VHH gene sequence obtained in Example 2 was ligated to the Fc fragment of human IgG1 (LALA mutation), and the linearized pCDNA3.1 vector was subjected to double digestion with homologous recombinase (purchased from Vazyme) and EcoR I/Not I, and the procedures were performed according to the product's instructions. The homologous recombination product was transformed into Top10 competent cells, coated on an ampicillin-resistant plate, and cultured at 37° C. overnight, and single clone was picked and sequenced.

3.2 Cell Transfection

ExpiCHO™ expression system kit (purchased from Thermo) was used to transfer the plasmid into Expi-CHO cells. The transfection method was carried out according to the product instructions. After the cells were cultured for 5 days, the supernatant was collected and the target protein was purified by the sorting method using protein A magnetic beads (purchased from Nanjing Jinsirui Biotechnology Co., Ltd.). The magnetic beads were resuspended with an appropriate volume of binding buffer (PBS+0.1% Tween 20, pH 7.4) (1-4 times the volume of magnetic beads), added to the sample to be purified, and incubated at room temperature for 1 hour with gentle shaking. The sample was placed on a magnetic stand (purchased from Suzhou Beaver Biomedical Engineering Co., Ltd.), the supernatant was discarded, and the magnetic beads were washed 3 times with binding buffer. Elution buffer (0.1M sodium citrate, pH 3.2) was added according to 3-5 times the volume of the magnetic beads, shaken at room temperature for 5-10 min, then it was placed back on the magnetic stand, the elution buffer was collected and transferred to a collection tube added with neutralization buffer solution (1M Tris, pH 8.54), and mixed well. The purified 4-1BB antibody fusion protein sample was used in Example 4 to Example 7 below.

Example 4: 4-1BB Antibody Fusion Protein Affinity Determination

ForteBio affinity determination was performed according to the existing method (Estep, P et al., Solution-based measurement of high-throughput antibody-antigen affinity and epitope classification, MAbs, 2013.5(2):p. 270-8). Briefly, the sensor was equilibrated offline for 30 min in the assay buffer, then the baseline was established by detection online for 60 s, and the purified antibody obtained as described above was loaded onto the AHQ sensor online. Then, the sensor was put into 100 nM 4-1BB antigen to act for 5 minutes, and the sensor was transferred to PBS and dissociated for 5 minutes. Analysis of kinetics was performed using a 1:1 binding model.

The experimental results were shown in Table 4 below.

TABLE 4

| Affinities of candidate molecules | | | | |
|---|---|---|---|---|
| Name | $K_D$(M) | Kon | Koff | SEQ ID NO: (VHH chain) |
| A-Na-16 | 2.08E−08 | 2.12E+05 | 4.40E−03 | 1 |
| A-Na-18 | 1.75E−08 | 2.38E+05 | 4.18E−03 | 2 |
| A-Na-19 | 1.51E−08 | 2.47E+05 | 3.72E−03 | 3 |
| A-Ye-02 | 4.66E−08 | 7.53E+04 | 3.51E−03 | 4 |
| A-Ye-03 | 2.83E−08 | 4.95E+04 | 1.40E−03 | 5 |
| A-Ye-04 | 2.22E−07 | 7.00E+04 | 1.56E−02 | 6 |
| A-Ye-05 | 1.56E−08 | 2.11E+05 | 3.29E−03 | 7 |
| A-Ye-10 | 1.85E−08 | 2.06E+05 | 3.82E−03 | 8 |
| A-Ye-13 | 1.19E−08 | 3.10E+05 | 3.68E−03 | 9 |
| A-Ye-14 | 1.45E−08 | 2.76E+05 | 4.01E−03 | 10 |
| A-Ye-15 | 1.82E−08 | 1.92E+05 | 3.50E−03 | 11 |
| A-Ye-18 | 1.66E−08 | 2.11E+05 | 3.49E−03 | 12 |
| A-Ye-19 | 1.30E−08 | 3.02E+05 | 3.93E−03 | 13 |
| A-Ye-21 | 2.30E−08 | 2.40E+05 | 5.51E−03 | 14 |
| A-Ye-22 | 2.26E−08 | 2.45E+05 | 5.52E−03 | 15 |
| A-Ye-23 | 2.34E−08 | 2.09E+05 | 4.88E−03 | 16 |
| A-Ye-25 | 1.35E−08 | 2.07E+05 | 2.78E−03 | 17 |
| A-Ye-27 | 7.55E−09 | 1.58E+05 | 1.19E−03 | 18 |
| A-Ye-30 | 1.73E−08 | 2.03E+05 | 3.51E−03 | 19 |
| A-Ye-33 | 1.49E−08 | 2.07E+05 | 3.08E−03 | 20 |
| A-Ye-20 | 2.68E−08 | 2.05E+05 | 5.48E−03 | 21 |
| A-Ye-35 | 1.84E−08 | 1.85E+05 | 3.40E−03 | 22 |
| L-Yr-13&14-01 | 1.95E−08 | 1.38E+05 | 4.44E−03 | 23 |
| L-Yr-13&14-02 | 4.47E−08 | 7.14E+04 | 3.09E−03 | 24 |
| L-Yr-13&14-03 | 1.91E−08 | 6.48E+04 | 2.67E−03 | 25 |
| L-Yr-13&14-05 | 3.35E−08 | 1.21E+05 | 4.12E−03 | 26 |
| L-Yr-13&14-06 | 2.06E−08 | 1.34E+05 | 1.92E−03 | 27 |
| L-Yr-13&14-07 | 1.43E−08 | 1.34E+05 | 1.92E−03 | 28 |
| L-Yr-13&14-08 | 2.05E−08 | 1.06E+05 | 2.16E−03 | 29 |
| L-Yr-13&14-09 | 2.10E−08 | 1.17E+05 | 2.46E−03 | 30 |
| L-Yr-13&14-10 | 4.60E−08 | 1.07E+05 | 4.93E−03 | 31 |
| L-Yr-13&14-11 | 2.16E−08 | 1.31E+05 | 2.83E−03 | 32 |
| L-Yr-13&14-12 | 3.08E−08 | 8.04E+05 | 2.47E−02 | 33 |
| L-Yr-13&14-13 | 2.32E−08 | 1.14E+05 | 2.64E−03 | 34 |
| L-Yr-13&14-16 | 1.96E−08 | 1.14E+05 | 2.24E−03 | 35 |
| L-Yr-13&14-17 | 2.51E−08 | 1.46E+05 | 3.65E−03 | 36 |

The results showed that the monovalent affinities of the anti-4-1BB molecules of the present invention were at the level of 1E-08, which met the requirements for the development of agonistic molecules.

Example 5: Binding of 4-1BB Antibody Fusion Protein to Human 4-1BB CHO-S Cells CHO cells overexpressing human 4-1BB (CHO-h4-1BB cells) were generated by transfection of pCHO1.0 vector (purchased from Invitrogen) encoding human 4-1BB cDNA cloned into MCS (multiple cloning site). The cell density of the expanded CHO-h4-1BB cells was adjusted to $2\times10^6$ cells/ml, added at 100 μl/well to a 96-well flow plate, and centrifuged for later use. The purified 4-1BB antibody was diluted with PBS by 3-fold dilution starting from 400 nM for a total of 12 points. The above-mentioned diluted sample was added at 100 μl/well to the above-mentioned 96-well flow plate with cells, incubated at 4° C. for 30 min, and washed twice with PBS. Goat F(ab')2 anti-human IgG-Fc (PE) (purchased from Abcam) diluted 100 times with PBS was added at 100 μl/well, incubated at 4° C. for 30 min, and washed twice with PBS. The cells resuspended with PBS was added at 100 μl/well, and detected on CytoFlex (Bechman) flow cytometer, and the corresponding MFI was calculated.

Figure 1B:
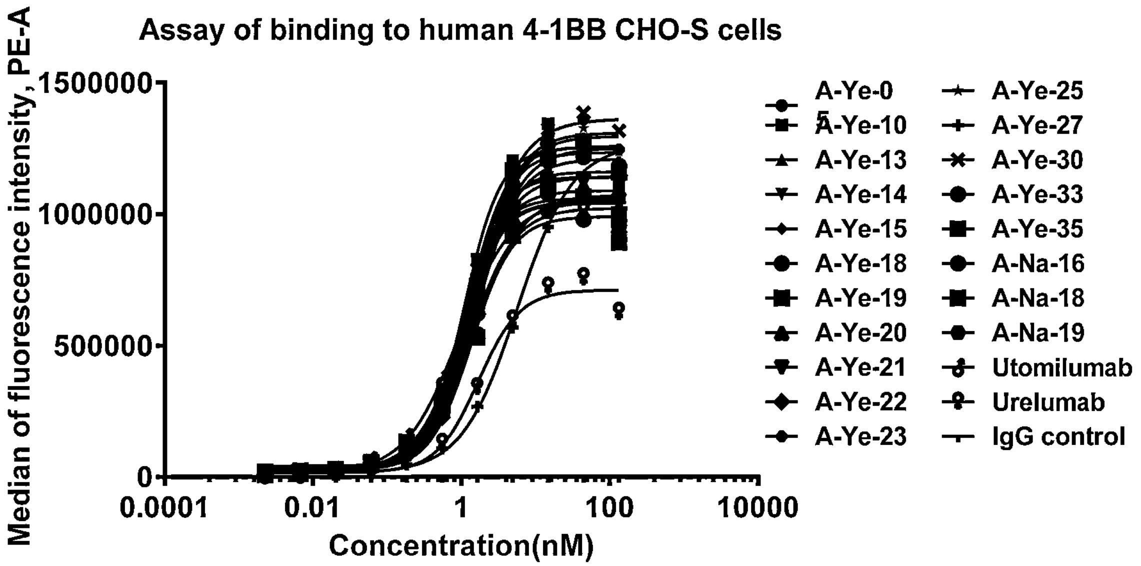
FIG. 1B shows the detection results of the second batch of 4-1BB antibodies of the present invention in binding to CHO cells stably expressing human 4-1BB.

The experimental results were shown in FIG. 1A and FIG. 1B.

The results showed that all the purified samples of the present invention had the activity of binding to CHO-h4-1BB cells, and the activity of some purified samples was similar to that of the control antibody Urelumab (US20090068192).

Example 6: Binding of 4-1BB Antibody Fusion Protein to Cynomolgus Monkey 4-1BB Protein Cynomolgus monkey 4-1BB-his protein (purchased from ACRO) was dissolved according to the instructions, diluted to 1 μg/ml with ELISA coating solution (purchased from Shanghai Sangon), coated on ELISA plate at 100 μl/well, allowed to stand overnight at 4° C., washed with PBST for 3 times, and blocked with 5% BSA (purchased from Shanghai Sangon) at room temperature for 1 hour. The coating solution was discarded, 4-1BB antibody serially diluted with 1% BSA by 3-fold dilution starting from 200 nM for a total of 12 points was added at 100 μl/well, and incubated at room temperature for 2 hours. Washing was performed with PBST three times, goat anti-human IgG-Fc-HRP (purchased from abcam) diluted with 1% BSA was added at 100 μl/well, and incubated at room temperature for 1 hour. Washing was performed 3 times with PBST, ELISA chromogenic solution (purchased from Solarbio) was added at 100 μl/well and reacted for 3 minutes at room temperature, ELISA stop solution (purchased from Solarbio) was added at 50 μl/well, and the absorbance value at 450 nm was read.

Figure 2A:
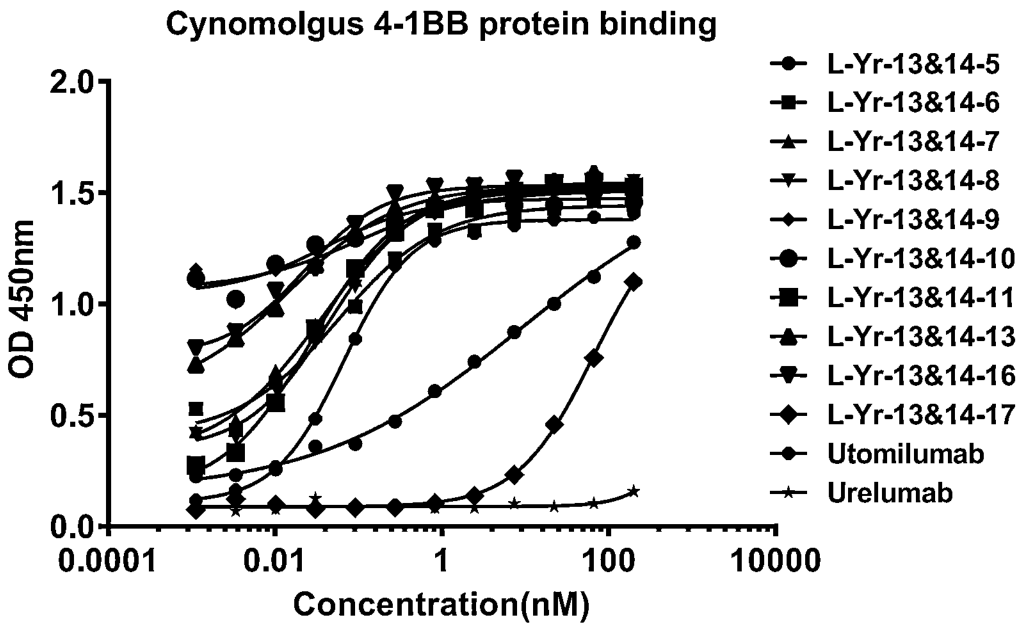
FIG. 2A shows the detection results of the first batch of 4-1BB antibodies of the present invention in binding to cynomolgus monkey 4-1BB protein.
Figure 2B:
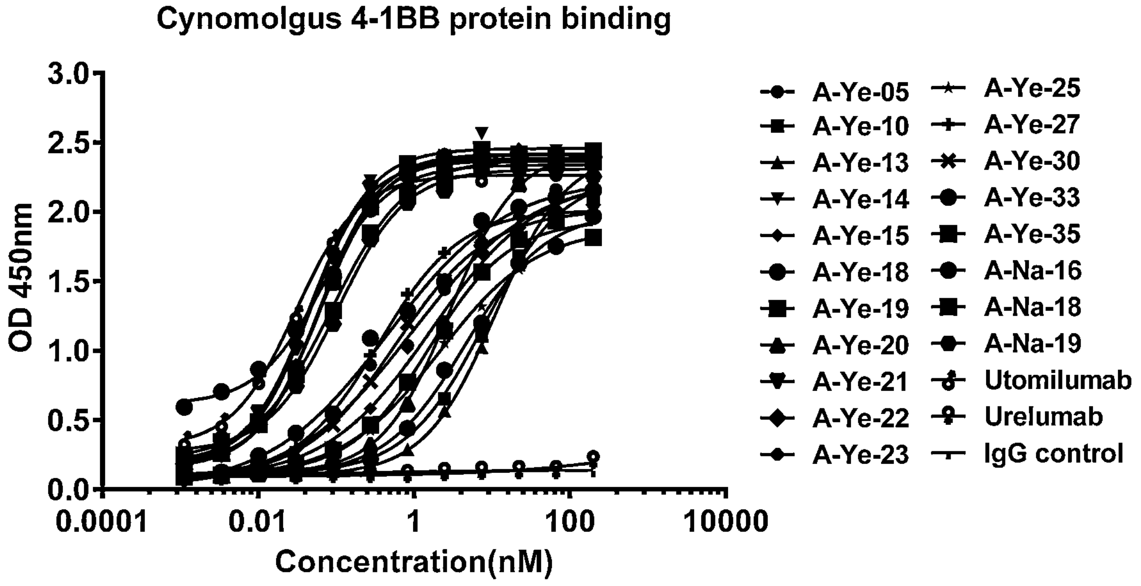
FIG. 2B shows the detection results of the second batch of 4-1BB antibodies of the present invention in binding to cynomolgus monkey 4-1BB protein.

The experimental results were shown in FIG. 2A and FIG. 2B, some purified samples of the present invention (e.g., L-Yr-13&14-16 and A-Na-19) and the control antibody Utomilumab had good binding activity to cynomolgus monkey 4-1BB protein, while the control antibody Urelumab (US20090068192) had weaker binding activity to cynomolgus monkey 4-1BB protein.

Example 7: Determination of Activation of Primary T Cells by 4-1BB Antibody Fusion Protein OKT-3 antibody (purchased from Biolegend) was diluted to 1 μg/ml with sterile PBS (purchased from Hyclone), and coated on a 96-well cell culture flat bottom plate (purchased from Thermo) at 50 μl/well, and anti-4-1BB antibody serially diluted with PBS was added at 50 μl/well at the same time, and incubated at 37° C. for 2 hours. Frozen human PBMCs (purchased from Shanghai Saili) were resuscitated, T cells were isolated with human T cell isolation and purification kit (purchased from Stemcell), the T cells were resuspended with X-VIVO15 medium (purchased from LONZA), and adjusted to have a cell density of $0.5\times10^6$ cells/ml for later use. After the antibody coating was completed, the coating solution was discarded, washing was performed twice with PBS, the PBS was discarded, and the above T cell suspension was added at 200 μl/well, incubated at 37° C., 5% $CO_2$ for 5 days, and the supernatant was collected to detect IFN-γ content.

Figure 3A:
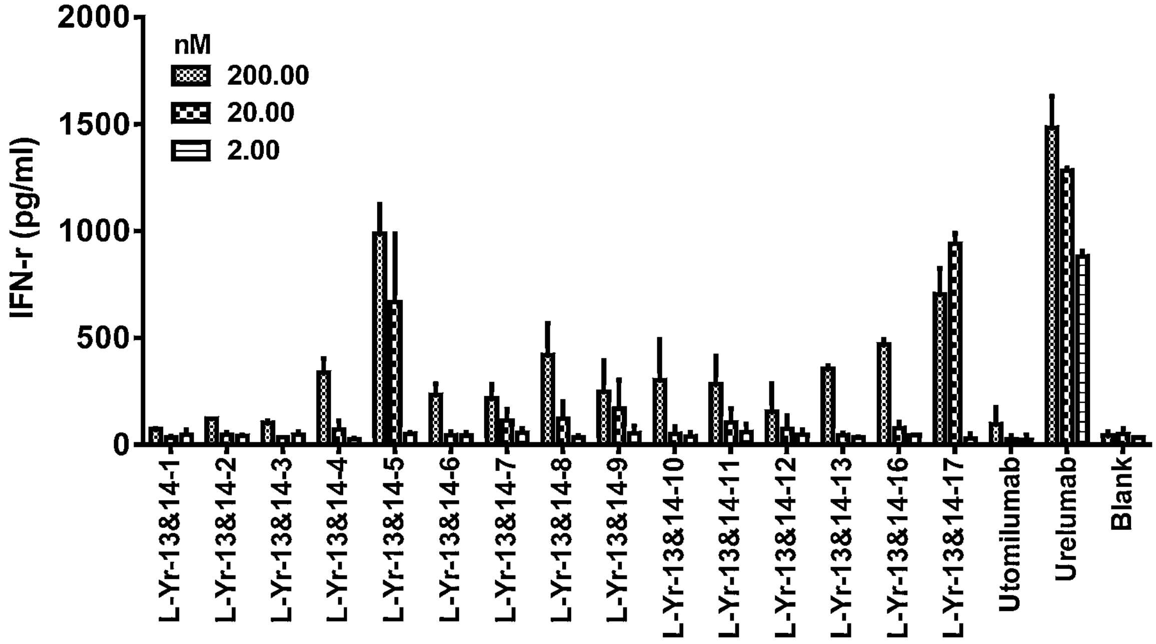
FIG. 3A shows the detection results of the first batch of 4-1BB antibodies of the present invention in activating primary T cells to produce IFN-γ.
Figure 3B:
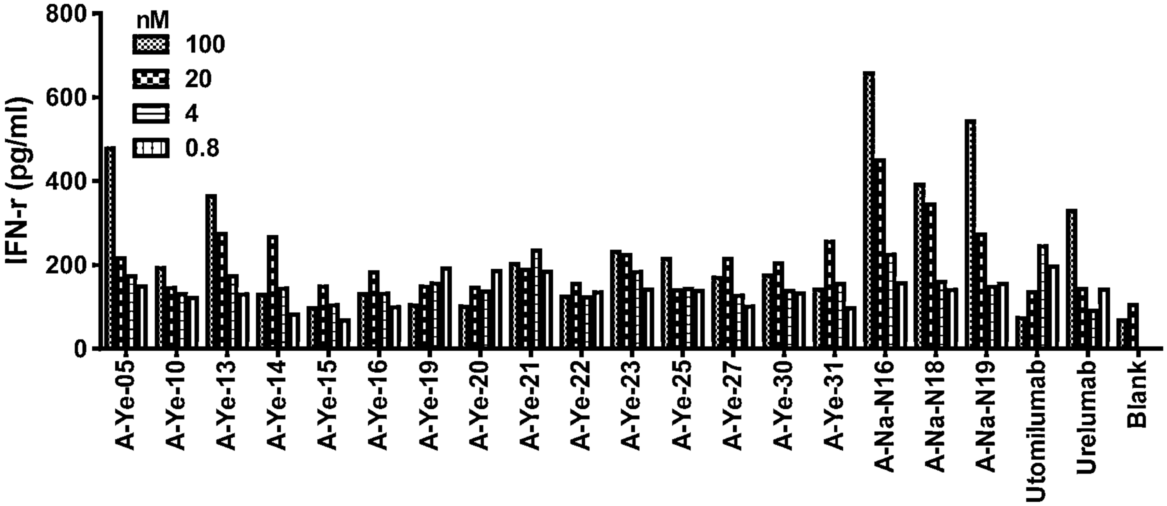
FIG. 3B shows the detection results of the second batch of 4-1BB antibodies of the present invention in activating primary T cells to produce IFN-γ.

The experimental results were shown in FIG. 3A and FIG. 3B, some purified samples of the present invention could activate human primary T cells to secrete IFN-γ, some samples (e.g., A-Na-16, A-Na-18, A-Na-19) had an activity comparable to that of the control antibody Urelumab (US20090068192), and some samples (e.g., L-Yr-13&14-16, L-Yr-13&14-17) had an activity between those of Urelumab and Utomiumab.

Example 8: Humanization and Expression of 4-1BB Antibody

In order to reduce the immunogenicity of monoclonal antibodies in human, L-Yr-13&14-16 and A-Na-19 antibodies were humanized. The humanization method was performed by the VHH humanized general framework transplantation method, and at the same time, by mutating some amino acids of antibody framework 2 (framework 2) according to the method reported in the literature (Vincke, C., et al., General strategy for humanizing camelid single-domain antibodies and identifying universal humanized nanobody scaffolds. J Biol Chem 284 (5): 3273-3284). The sequences SEQ ID NOs: 39-40 and SEQ ID NOs: 37-38 were respectively obtained.

In this study, IMGT (http://www.imgt.org) was used to evaluate the humanization level of the humanized sequences of L-Yr-13&14-16 and A-Na-19 antibodies, and the results were shown in Table 5.

TABLE 5

L-Yr-13&14-16 and A-Na-19 humanization sequences and human homology (comparison of VHH sequences)

| No. | Germ line | Homology | SEQ ID NO: |
|---|---|---|---|
| L-Yr-13&14-16 | IGHV3-30*01 | 76.3% | 35 |
| HZ-L-Yr-13&14-16-1 | IGHV3-30*01 | 80.4% | 39 |
| HZ-L-Yr-13&14-16-2 | IGHV3-30*01 | 84.5% | 40 |
| A-Na-19 | IGHV3-30*01 | 69.4% | 3 |
| Hu-A-NA-19-1 | IGHV3-15*06 | 76.5% | 37 |
| Hu-A-NA-19-2 | IGHV3-15*06 | 78.6% | 38 |

Figure 4A:
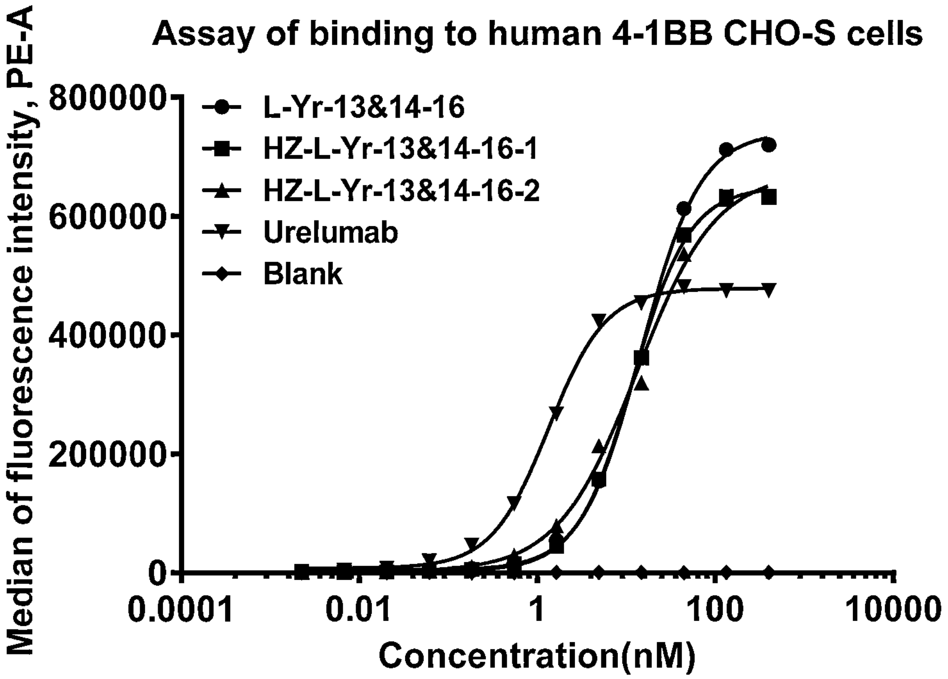
FIG. 4A shows the detection results of the genetically engineered progeny molecules of L-Yr-13&14-16 molecule of the present invention in binding to CHO cells stably expressing human 4-1BB.
Figure 4B:
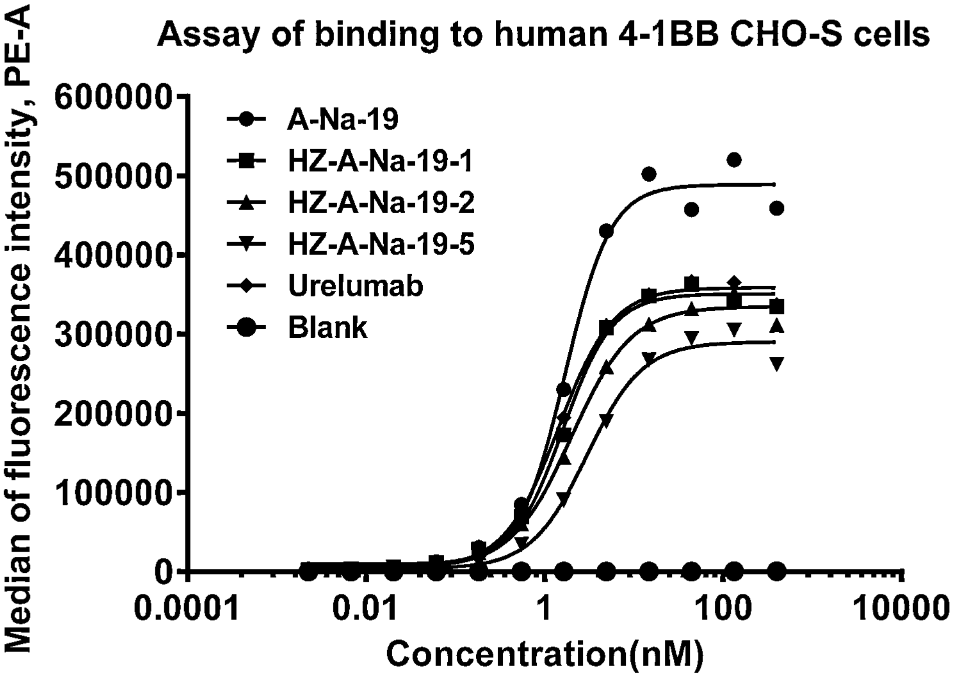
FIG. 4B shows the detection results of the genetically engineered progeny molecules of A-Na-19 molecule of the present invention in binding to CHO cells stably expressing human 4-1BB.

Protein construction and expression purification methods were the same as in Example 3. The purified genetically engineered antibodies were tested for binding to human 4-1BB CHO-S cells, and the detection method was the same as in Example 4. The results were shown in FIG. 4A and FIG. 4B, the genetically engineered antibodies maintained the activity of binding to human 4-1BB CHO-S cells.

Figure 5A:
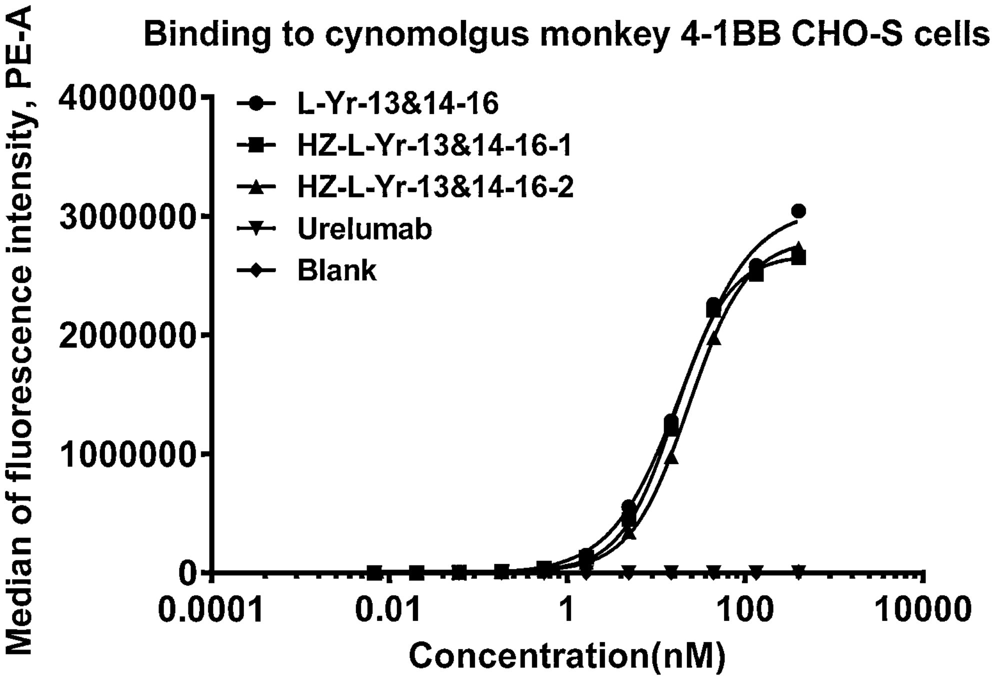
FIG. 5A shows the detection results of the genetically engineered progeny molecules of L-Yr-13&14-16 molecule of the present invention in binding to CHO cells stably expressing cynomolgus monkey 4-1BB.
Figure 5B:
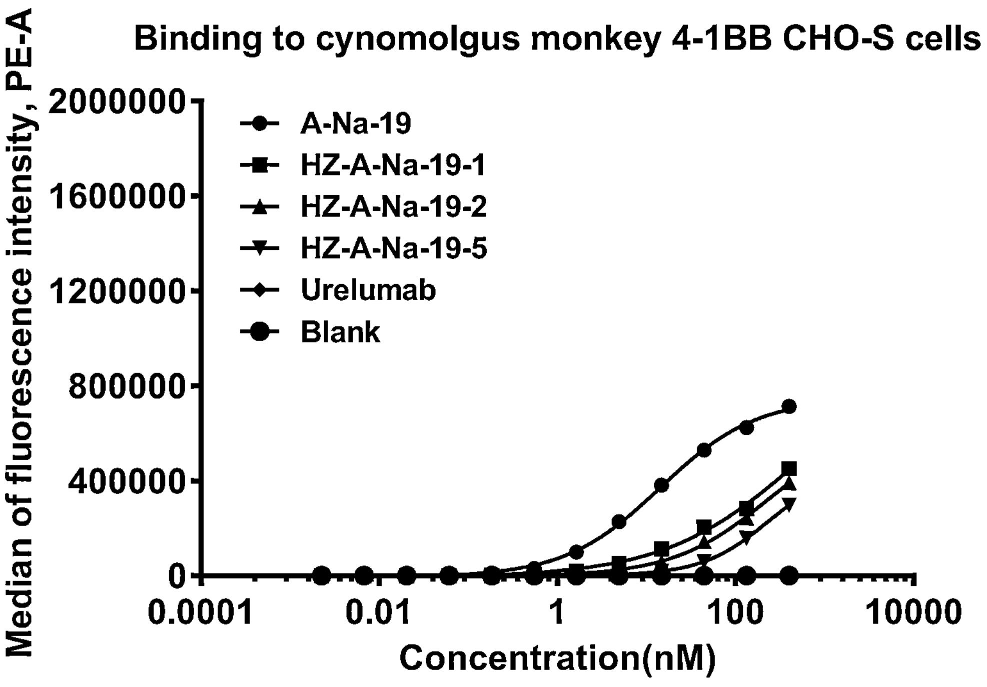
FIG. 5B shows the detection results of the genetically engineered progeny molecules of A-Na-19 molecule of the present invention in binding to CHO cells stably expressing cynomolgus monkey 4-1BB.

The purified genetically engineered antibodies were tested for binding to cynomolgus monkey 4-1BB CHO-S cells. The results were shown in FIG. 5A and FIG. 5B. The results showed that the genetically engineered HZ-L-Yr-13&14-16 antibody maintained the binding activity to cynomolgus monkey 4-1BB CHO-S cells, while the genetically engineered A-Na-19 antibodies HZ-A-Na-19-1 and HZ-A-Na-19-2 had a significantly decreased binding activity to cynomolgus monkey 4-1BB CHO-S cells.

Figure 6A:
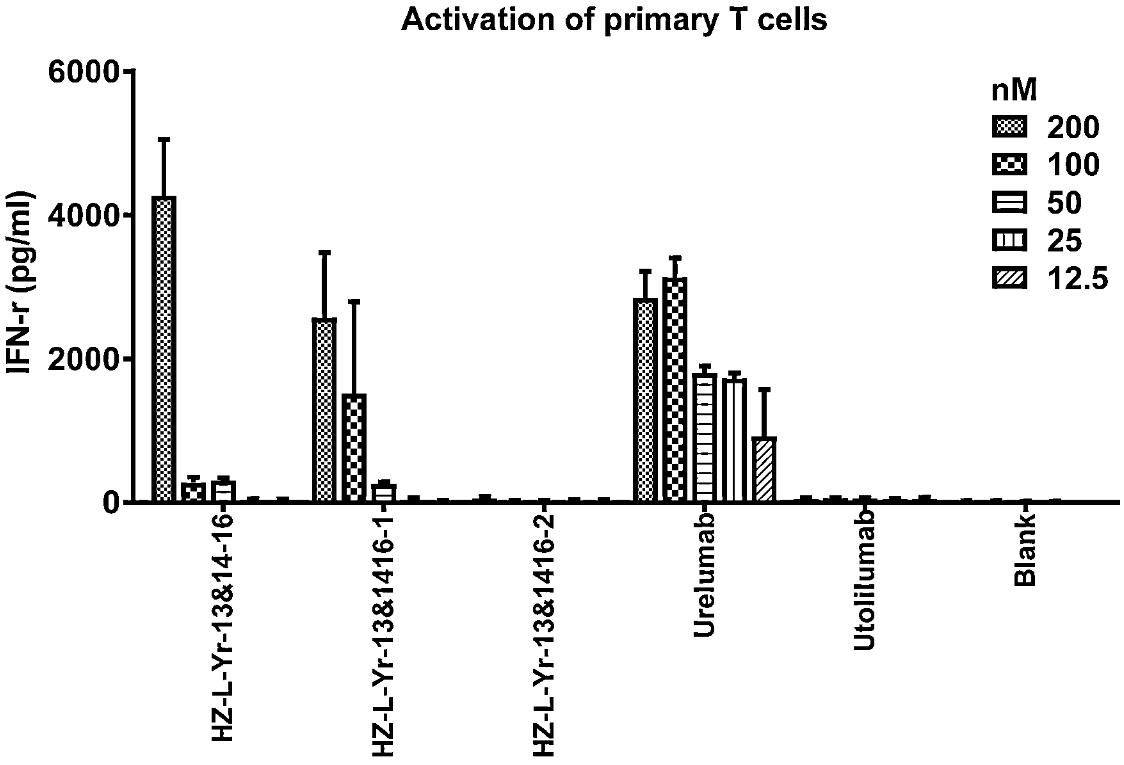
FIG. 6A shows the detection results of the genetically engineered progeny molecules of L-Yr-13&14-16 molecule of the present invention in activating primary T cells to produce IFN-γ.
Figure 6B:
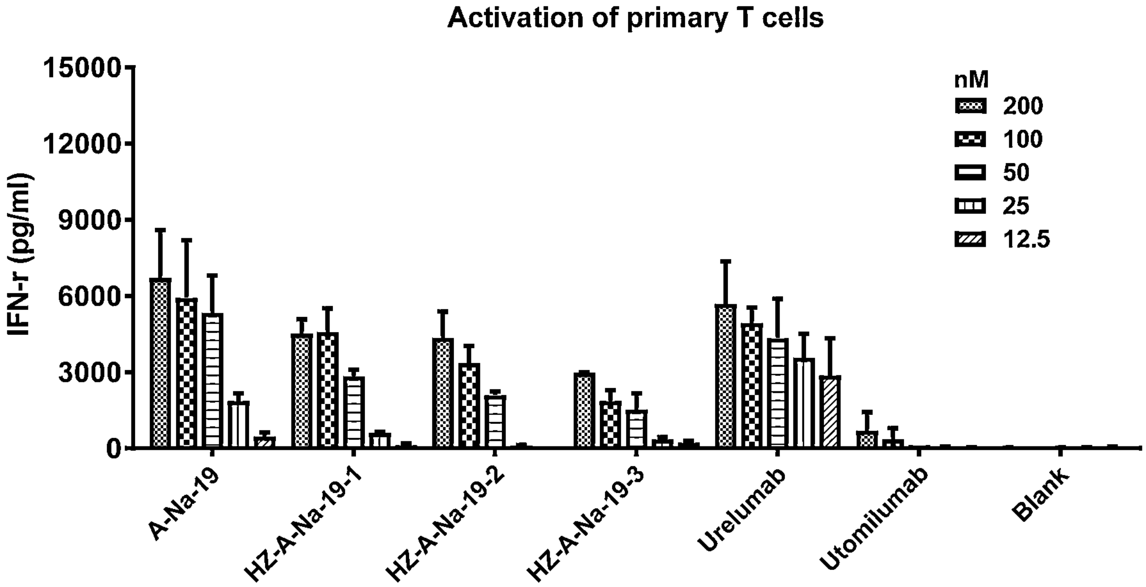
FIG. 6B shows the detection results of the genetically engineered progeny molecules of A-Na-19 molecule of the present invention in activating primary T cells to produce IFN-γ.

The purified genetically engineered antibodies were tested for activation of primary T cells, and the detection method was the same as in Example 7. The results were shown in FIG. 6A and FIG. 6B. The results showed that the genetically engineered HZ-L-Yr-13&14-16-1 and HZ-A-Na-19-1 maintained the activity of activating primary T cells.

Example 9: 4-1BB Ligand Blocking Test

The expanded CHO-h4-1BB cells were adjusted to have a cell density of $2\times10^6$ cells/ml, added to a 96-well flow plate at 100 μl/well, and centrifuged for later use. The purified 4-1BB antibody was diluted to 400 nM with PBS, and the above-mentioned diluted sample was added at 50 μl/well to the above-mentioned 96-well flow plate with cells, and incubated at 4° C. for 30 min. Biotin-4-1BB ligand protein (purchased from ACRO) diluted to 1 μg/ml with PBS was added at 50 μl/well, and incubated at 4° C. for 30 min. Washing was performed twice with PBS, SAPE (purchased from Thermo) diluted 200 times with PBS was added at 100 μl/well, incubated at 4° C. for 30 min, and washed twice with PBS. PBS was added at 100 μl/well to resuspend the cells, the detection was carried out on CytoFlex (Bechman) flow cytometer and the corresponding MFI was calculated.

Figure 7A:
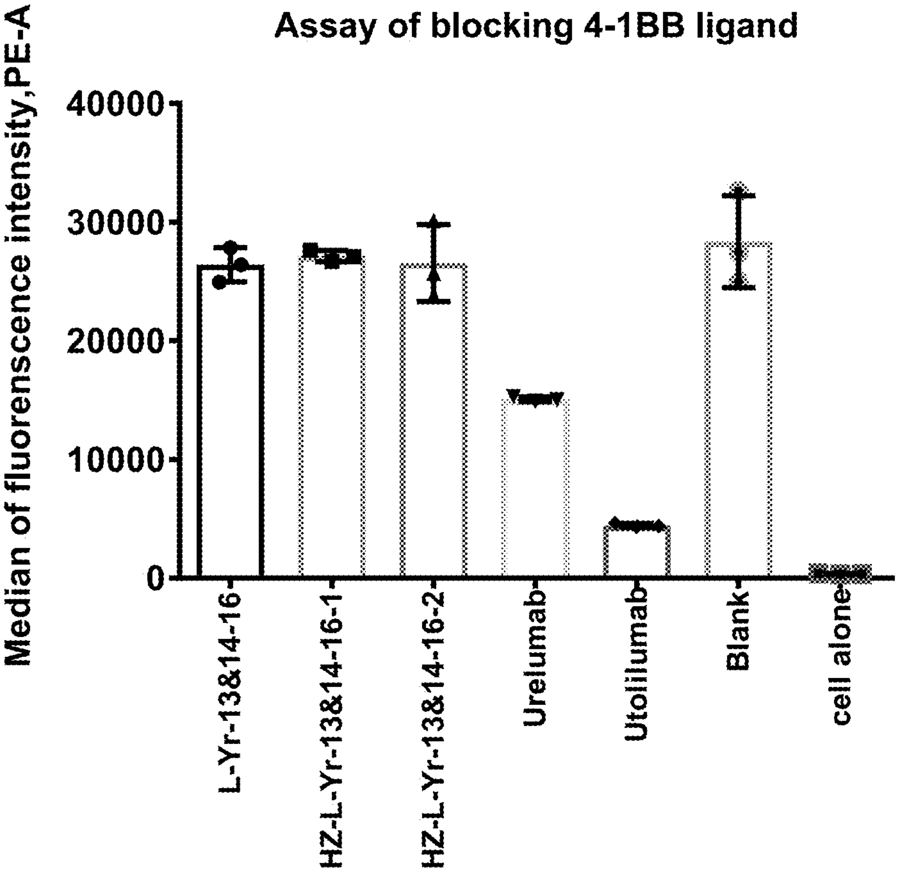
FIG. 7A shows the detection results of the genetically engineered progeny molecules of L-Yr-13&14-16 molecule of the present invention in blocking the binding of 4-1BB ligand to 4-1BB.

The results were shown in FIG. 7A. The results showed that the genetically engineered 4-1BB antibody HZ-L-Yr-13&14-16-1 had no ligand blocking activity, the control antibody Utomilumab (US20120237498) had ligand blocking activity, and Urelumab had partial blocking activity.

Example 10: Binding Detection of Antibodies and TNFRSF Members

Human 4-1BB-his, GITR-his, OX40-his, CD40-his proteins (purchased from ACRO) were dissolved according to the instructions, diluted to 1 μg/ml with ELISA coating solution (purchased from Shanghai Sangon), coated on ELISA plate at 100 allowed to stand overnight at 4° C., and washed for 3 times with PBST, 5% BSA (purchased from Shanghai Sangon) was added at 200 μl/well to block for 1 hour at room temperature. The coating solution was discarded, 4-1BB antibody diluted with 1% BSA was added at 100 μl/well, 200 nM in three replicate wells, and incubated at room temperature for 2 hours. Washing was performed with PBST for 3 times, and goat anti-human IgG-Fc-HRP (purchased from abcam) diluted with 1% BSA was added at 100 μl/well, and incubated at room temperature for 1 hour. Washing was performed 3 times with PBST, ELISA chromogenic solution (purchased from Solarbio) was added at 100 μl/well to react at room temperature for 3 minutes, ELISA stop solution (purchased from Solarbio) was added at 50 and the absorbance value at 450 nm was read.

Figure 7B:
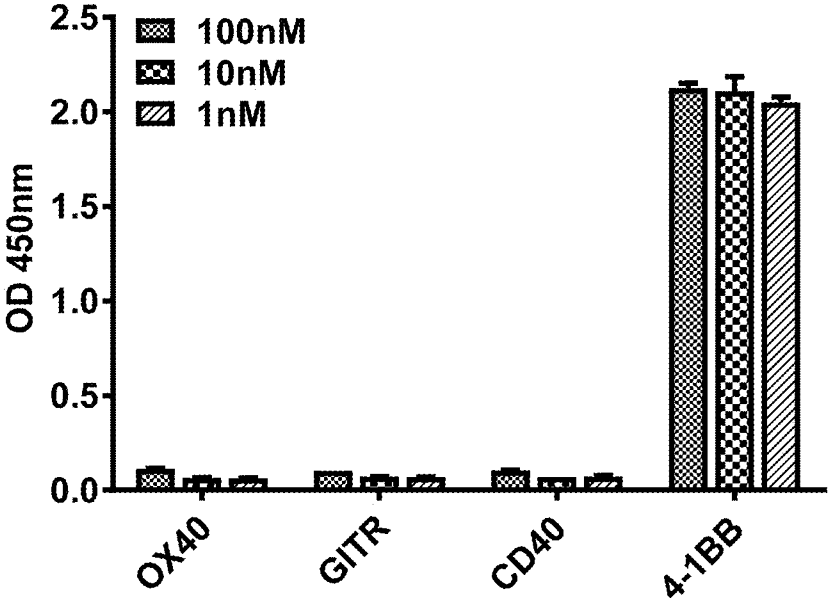
FIG. 7B shows the detection results of the binding of L-Yr-13&14-16-1 molecule of the present invention to TNFRSF members.

The results were shown in FIG. 7B. The results showed that the HZ-L-Yr-13&14-16-1 antibody only bound to 4-1BB protein, and did not bind to other members of tumor necrosis factor receptor superfamily. It showed that the antibody of the present invention had good specificity, would not activate other members of the tumor necrosis factor receptor superfamily in vivo, thereby avoiding potential side effects.

Example 11: Identification of Crystal Structure of the Complex of 4-1BB and VHH Segment In order to further explore the binding mode of the 4-1BB nanobody of the present invention to its antigen protein, in this example, L-Yr-13&14-16-1 was selected to carry out the crystallization experiment of antigen complex.

Wherein, in order to promote the formation of crystal, after optimization, the amino acid sequence of anti-4-1BB antibody in the final crystal complex was a sequence (SEQ ID NO: 169) formed by adding Leu and Gly at the C-terminal of the VHH chain sequence (i.e., SEQ ID NO: 39) of L-Yr-13&14-16-1. It should be noted that the Leu and Gly residues added at the C-terminal were only routine technical operations to facilitate crystallization, and would not affect the binding mode of nanobody L-Yr-13&14-16-1 to human 4-1BB protein.

Figure 8:
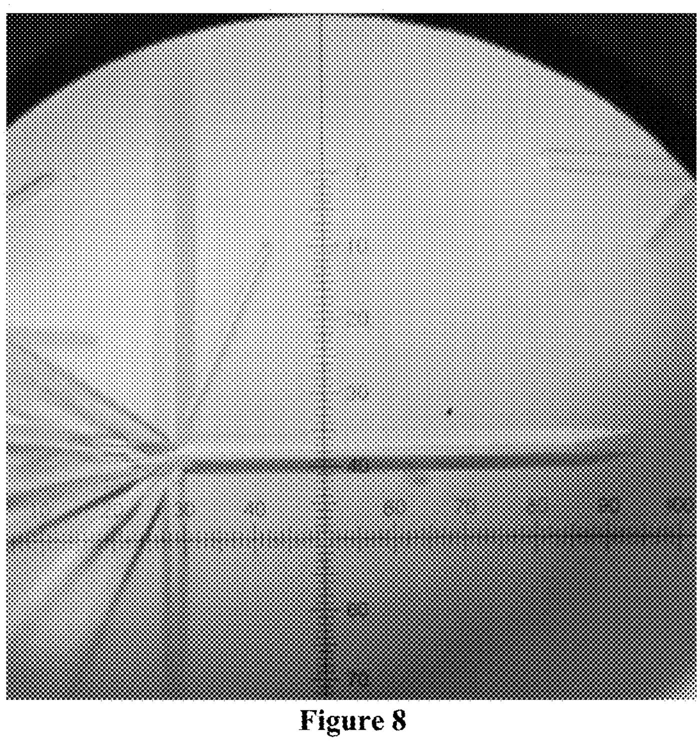
FIG. 8 shows the schematic diagram of the crystal of 4-1BB-VHH complex of the present invention.

In this experiment, the X-ray diffraction method was used to identify the crystal structure of the complex of 4-1BB and VHH segment. Both human 4-1BB protein (SEQ ID NO: 168) and anti-4-1BB VHH protein (SEQ ID NO: 169) were expressed by HEK293 system. The 4-1BB was mixed with VHH at a molar ratio of 1:1 to prepare the complex sample for crystallization. The complex (8.5 mg/mL) was mixed with crystallization reagent at a ratio of 1:1 and crystallized at 18° C. Crystals were observed after four days in the JBK kit culture conditions, and the crystal morphology was shown in FIG. 8.

Single crystals were selected for X-ray diffraction experiment at Shanghai Light Source and diffraction data with a resolution of 3.14 Å were obtained. Data processing was carried out by using XDS software. The molecular replacement method was used to identify the crystal phase using the structures of 4-1BB (PDB ID: 6mgp) and VHH (PDB ID: 4xtl) as models. Crystal structure refinement was performed using Refmac5. COOT was used for model checking, manual reconstruction, and structural validation. The complex crystal belonged to the P41212 space group, and its unit-cell parameters were: a=106.85 Å, b=106.85 Å, c=146.41 Å, α=90.00°, β=90.00°, γ=90.00°. The statistics of specific crystal data were shown in Table 6.

TABLE 6

Statistics of crystal data of 4-1BB-VHH complex

| | |
|---|---|
| Resolution (Å) | 47.79-3.14 (3.36-3.14) |
| Space group | P41212 |
| Unit cell | |
| a (Å) | 106.85 |
| b (Å) | 106.85 |
| c (Å) | 146.41 |
| α, β, γ (°) | 90.00, 90.00, 90.00 |
| $R_{merge}$ (total/outer layer) | 0.156 (1.195) |
| $R_{working}$, $R_{free}$ | 0.204/0.242 |
| $CC_{1/2}$ (total/outer layer) | 0.998 (0.894) |
| I/σ(I) (total/outer layer) | 16.1 (2.6) |
| Integrity (total/outer layer) (%) | 99.9 (98.8) |
| Redundancy | 12.9 (12.8) |
| Rpim (total/outer layer) (%) | 0.047 (0.359) |
| RMSD bond length (Ang.) | 0.012 |
| RMSD bond angle (deg.) | 2.466 |

Figure 9:
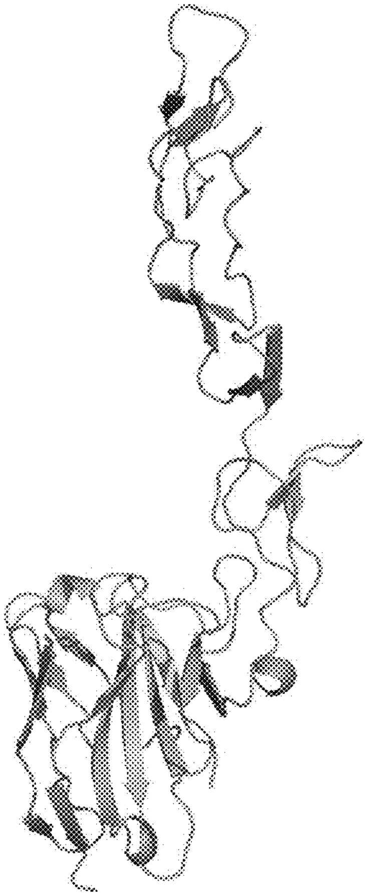
FIG. 9 shows the crystal structure of the 4-1BB-VHH complex of the present invention. Among them, green represents 4-1BB protein; and blue represents the VHH chain of anti-4-1BB nanobody.
Figure 10:
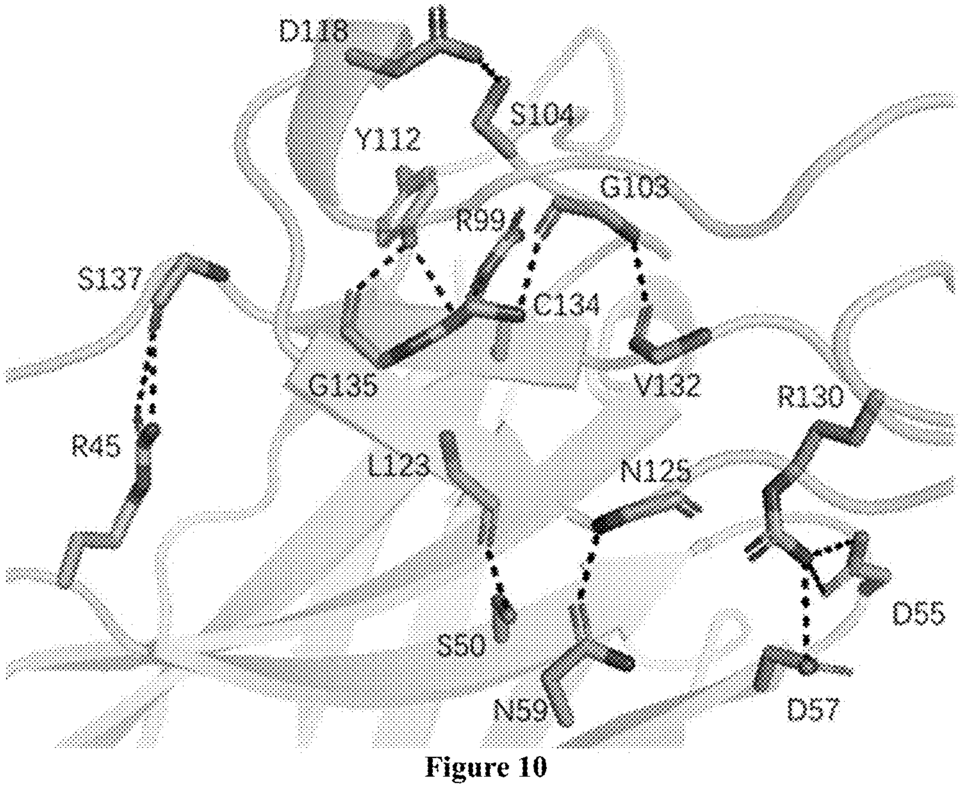
FIG. 10 shows the hydrogen bonding interaction interface in the crystal structure of the 4-1BB-VHH complex of the present invention. Among them, green represents 4-1BB protein; and blue represents the VHH chain of anti-4-1BB nanobody.
Figure 11:
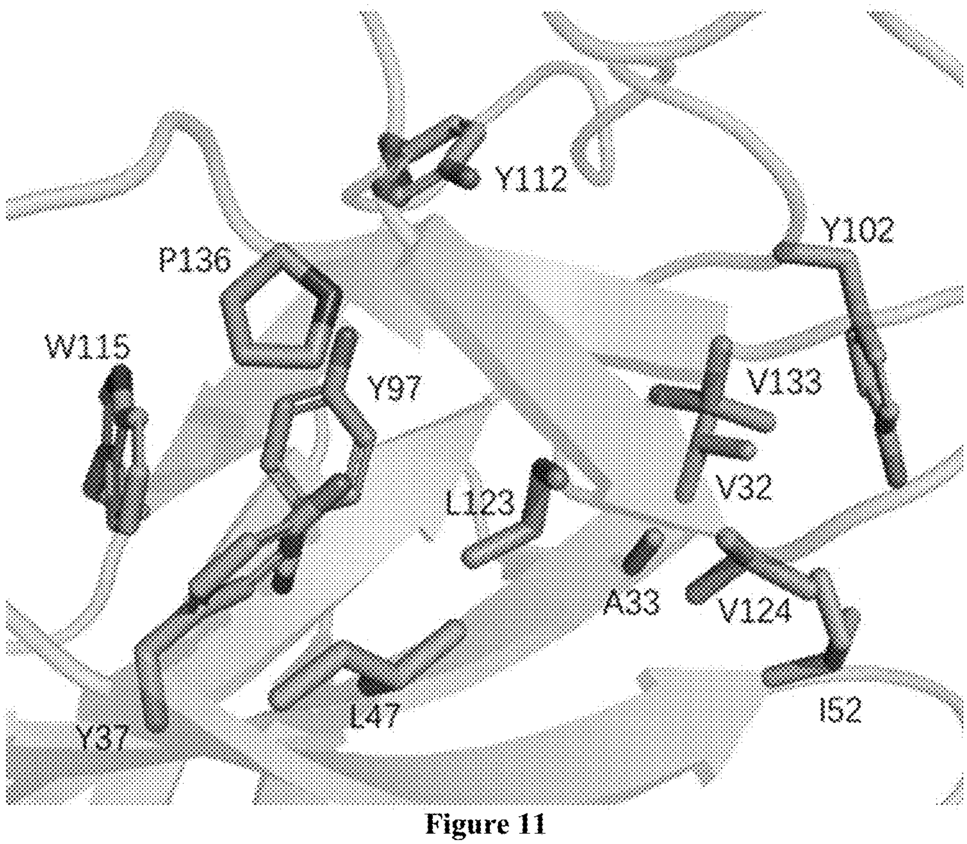
FIG. 11 shows the hydrophobic interaction interface in the crystal structure of the 4-1BB-VHH complex of the present invention. Among them, green represents 4-1BB protein; and blue represents the VHH chain of anti-4-1BB nanobody.

The crystal structure of the 4-1BB-VHH complex obtained after structural analysis was shown in FIG. 9. Epitope analysis showed that the main hydrogen bonding between 4-1BB and VHH was concentrated on amino acids such as Asp118, Leu123, Arg130, Val132, Cys134, Gly135 and Ser137 of 4-1BB (FIG. 10). In addition, Leu123, Val124, Val133 and Pro136 of 4-1BB and Val32, Ala33, Tyr37, Leu47, Ile52, Tyr97, Tyr102 and Trp115 of VHH constituted a hydrophobic interaction interface (FIG. 11).

The binding site between Urelumab and 4-1BB was located at the N-terminal of 4-1BB, and the amino acids of 4-1BB mainly involved in the binding included Pro27, Asn40, Asn42, and Gln43; Utomilumab mainly bound to the CRD3 (Cysteine rich domain) and CRD4 of 4-1BB, the amino acids of 4-1BB mainly involved in the binding included Arg66, Gly96, Ser100, Cys102, Lys114, Arg130 and Arg134 (Chin S M, Kimberlin C R, Roe-Zurz Z, et al. Structure of the 4-1BB/4-1BBL complex and distinct binding and functional properties of utomilumab and urelumab. Nat Commun 2018; 9:4679.). In addition, theoretically, the binding epitope of Utomilumab had a competitive relationship with the 4-1BB ligand in space, so it would have a certain blocking effect on the binding of 4-1BB to its ligand.

Although specific embodiments of the present invention have been described in detail, those skilled in the art will understand that based on all the teachings that have been disclosed, various modifications and substitutions can be made to those details, and these changes are all within the scope of the present invention. The full scope of the present invention is given by the appended claims and any equivalents thereof

What is claimed is:

1. An anti-4-1BB single-domain antibody, comprising a heavy chain variable region, the heavy chain variable region comprising CDR1 to CDR3, wherein CDR1 has an amino acid sequence selected from SEQ ID NOs: 41-80, CDR2 has an amino acid sequence selected from SEQ ID NOs: 81-120, and CDR3 has an amino acid sequence selected from SEQ ID NOs: 121-160;

or, the amino acid sequences of CDR1 to CDR3 are shown in any one of the following items 1-40:

| Item No. | CDR1's SEQ ID NO: | CDR2's SEQ ID NO: | CDR3's SEQ ID NO: |
|---|---|---|---|
| 1 | 41 | 81 | 121 |
| 2 | 42 | 82 | 122 |
| 3 | 43 | 83 | 123 |
| 4 | 44 | 84 | 124 |
| 5 | 45 | 85 | 125 |
| 6 | 46 | 86 | 126 |
| 7 | 47 | 87 | 127 |
| 8 | 48 | 88 | 128 |
| 9 | 49 | 89 | 129 |
| 10 | 50 | 90 | 130 |
| 11 | 51 | 91 | 131 |
| 12 | 52 | 92 | 132 |
| 13 | 53 | 93 | 133 |
| 14 | 54 | 94 | 134 |
| 15 | 55 | 95 | 135 |
| 16 | 56 | 96 | 136 |
| 17 | 57 | 97 | 137 |
| 18 | 58 | 98 | 138 |
| 19 | 59 | 99 | 139 |
| 20 | 60 | 100 | 140 |
| 21 | 61 | 101 | 141 |
| 22 | 62 | 102 | 142 |
| 23 | 63 | 103 | 143 |
| 24 | 64 | 104 | 144 |
| 25 | 65 | 105 | 145 |
| 26 | 66 | 106 | 146 |
| 27 | 67 | 107 | 147 |
| 28 | 68 | 108 | 148 |
| 29 | 69 | 109 | 149 |
| 30 | 70 | 110 | 150 |
| 31 | 71 | 111 | 151 |
| 32 | 72 | 112 | 152 |
| 33 | 73 | 113 | 153 |
| 34 | 74 | 114 | 154 |
| 35 | 75 | 115 | 155 |
| 36 | 76 | 116 | 156 |
| 37 | 77 | 117 | 157 |
| 38 | 78 | 118 | 158 |
| 39 | 79 | 119 | 159 |
| 40 | 80 | 120 | 160. |

2. The anti-4-1BB single-domain antibody according to claim 1, characterized by one or more of the following:

(1) any one, two, three or all 4 of its 4 framework regions are humanized;

(2) the second framework region is humanized;

(3) the second framework region is humanized; and the first, third or forth framework region is also humanized;

(4) the anti-4-1BB single-domain antibody has an identity of greater than or equal to 75%, greater than or equal to 76%, greater than or equal to 77%, greater than or equal to 78%, greater than or equal to 79%, or greater than or equal to 80% to that of human; or (5) in the anti-4-1BB single-domain antibody, the framework region 1 has an amino acid sequence as set forth in SEQ ID NO: 170, the framework region 2 has an amino acid sequence as set forth in SEQ ID NO: 171 or SEQ ID NO: 172, the framework region 3 has an amino acid sequence as set forth in SEQ ID NO: 173, and the framework region 4 has an amino acid sequence as set forth in SEQ ID NO: 174.

3. The anti-4-1BB single-domain antibody according to claim 1, which has a $K_D$ less than E-07, less than 5E-08, less than 4E-08, less than 3E-08, or less than 2E-08 with 4-1BB antigen; and has a $K_D$ higher than 4.55E-09; wherein the $K_D$ is measured by a biolayer interferometry.

4. The anti-4-1BB single-domain antibody according to claim 1, which has a binding site to 4-1BB antigen that is different from that of urelumab and utomilumab.

5. The anti-4-1BB single-domain antibody according to claim 1, which specifically binds to human 4-1BB and simultaneously cross-binds to cynomolgus monkey 4-1BB.

6. The anti-4-1BB single-domain antibody according to claim 1, which does not block the binding of 4-1BB ligand to 4-1BB in a natural state.

7. The anti-4-1BB single-domain antibody according to claim 1, which has an amino acid sequence as set forth in any one of SEQ ID NOs: 1-40.

8. A kit, which comprises the anti-4-1BB single-domain antibody according to claim 1;

the kit further comprises a second antibody capable of specifically binding to the single-domain antibody or to the fusion protein; and the second antibody further comprises a detectable label.

9. A fusion protein, which comprises the anti-4-1BB single-domain antibody according to claim 1, and an Fc fragment of human IgG or a heavy chain constant region of human IgG.

10. The fusion protein according to claim 9, wherein, according to the EU numbering system, the Fc fragment of human IgG or the heavy chain constant region of human IgG comprises a L234A mutation and a L235A mutation; or the Fc fragment of IgG further comprises a G237A mutation.

11. The fusion protein according to claim 9, wherein, the Fc fragment of human IgG is an Fc fragment of human IgG1; or the heavy chain constant region of human IgG is a heavy chain constant region of human IgG1.

12. The fusion protein according to claim 9, wherein, the Fc fragment of human IgG is an Fc fragment of human IgG1 comprising a L234A mutation and a L235A mutation;

the Fc fragment of human IgG is an Fc fragment of human IgG1 comprising a L234A mutation, a L235A mutation and a G237A mutation; or the Fc fragment of human IgG1 has an amino acid sequence as set forth in SEQ ID NO: 167.

13. The fusion protein according to claim 9, wherein, the Fc fragment of human IgG or the constant region of human IgG is ligated directly or through a linker fragment to the C-terminus of the anti-4-1BB single-domain antibody.

14. A conjugate, which comprises an antibody moiety and a coupling moiety, wherein the antibody moiety is the anti-4-1BB single-domain antibody according to claim 1, and the coupling moiety is a detectable label.

15. A pharmaceutical composition, which comprises the anti-4-1BB single-domain antibody according to claim 1; and a pharmaceutically acceptable excipient.

16. A method for treating and/or reducing the likelihood a malignant tumor or autoimmune disease, comprising a step of administering an effective amount of the anti-4-1BB single-domain antibody according to claim 1 to a subject in need thereof.

17. The method according to claim 16, wherein, the malignant tumor is selected from the group consisting of rectal cancer, colon cancer, lung cancer, breast cancer, melanoma, liver cancer, gastric cancer, renal cell carcinoma, ovarian cancer, esophageal cancer and head and neck cancer; or the autoimmune disease is selected from the group consisting of autoimmune encephalomyelitis, lupus-like syndrome and collagen-induced arthritis.

18. An anti-4-1BB nanobody, where, the anti-4-1BB nanobody has a VHH chain with an amino acid sequence as set forth in any one of SEQ ID NOs: 1-40;

or has an amino acid sequence which is a derived sequence of any one of the above amino acid sequence and is subjected to an addition, deletion, modification and/or substitution of 1-8 amino acid residues, and is capable of retaining the 4-1BB binding affinity of the 4-1BB nanobody.

19. A recombinant protein, wherein the recombinant protein comprises:

(i) a sequence of the anti-4-1BB nanobody according to claim 18; and (ii) optionally a tag sequences to help expression and/or purification.

20. A fusion protein, characterized in that the fusion protein has a structure as shown in Formula I from the N-terminus to the C-terminus:

Z1-L-Z2 (Formula I)

in the Formula,

Z1 represents one or more VHH chains of the anti-4-1BB nanobody according to claim 18;

Z2 represents an Fc fragment of immunoglobulin;

L represents an optional linker sequence.

21. An immunoconjugate, where the immunoconjugate comprises:

(i) the anti-4-1BB nanobody according to claim 18; and (ii) a coupling moiety selected from a group consisting of a detectable label, drug, toxin, cytokine, radionuclide, or enzyme.

22. A pharmaceutical composition, comprising:

(i) the anti-4-1BB nanobody according to claim 18; and (ii) a pharmaceutically acceptable carrier.

23. A method for treating a tumor, comprising a step of administering an effective amount of the anti-4-1BB nanobody according to a claim 18 to a subject in need thereof.

* * * * *